US009610340B2

(12) United States Patent
Biemans et al.

(10) Patent No.: US 9,610,340 B2
(45) Date of Patent: Apr. 4, 2017

(54) **VACCINE COMPRISING *STREPTOCOCCUS PNEUMONIAE* CAPSULAR POLYSACCHARIDE CONJUGATES**

(75) Inventors: Ralph Leon Biemans, Rixensart (BE); Nathalie Marie-Josephe Garçon, Rixensart (BE); Philippe Vincent Hermand, Rixensart (BE); Jan Poolman, Haarlem (BE); Marcelle Paulette Van Mechelen, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 629 days.

(21) Appl. No.: 12/665,350

(22) PCT Filed: Jun. 24, 2008

(86) PCT No.: PCT/EP2008/057999
§ 371 (c)(1),
(2), (4) Date: Dec. 18, 2009

(87) PCT Pub. No.: WO2009/000826
PCT Pub. Date: Dec. 31, 2008

(65) Prior Publication Data
US 2010/0209450 A1 Aug. 19, 2010

(30) Foreign Application Priority Data

Jun. 26, 2007 (GB) .................................. 0712420.9
Jun. 26, 2007 (GB) .................................. 0712428.2
Jun. 26, 2007 (GB) .................................. 0712435.7

(51) Int. Cl.
*A61K 39/09* (2006.01)
*A61K 47/48* (2006.01)
*A61K 39/00* (2006.01)
*A61K 39/116* (2006.01)

(52) U.S. Cl.
CPC ............ *A61K 39/092* (2013.01); *A61K 39/09* (2013.01); *A61K 47/4833* (2013.01); *A61K 39/116* (2013.01); *A61K 2039/55* (2013.01); *A61K 2039/55555* (2013.01); *A61K 2039/55566* (2013.01); *A61K 2039/6037* (2013.01); *A61K 2039/6068* (2013.01); *A61K 2039/70* (2013.01)

(58) Field of Classification Search
None
See application file for complete search history.

(56) References Cited

U.S. PATENT DOCUMENTS

| 5,695,768 | A | 12/1997 | Malcolm |
| 5,785,973 | A | 7/1998 | Bixler et al. |
| 5,965,714 | A | 10/1999 | Ryall |
| 6,582,706 | B1 | 6/2003 | Johnson et al. |
| 6,656,472 | B1 | 12/2003 | Chong et al. |
| 8,808,708 | B2 | 8/2014 | Hausdorf et al. |
| 2003/0099672 | A1 | 5/2003 | Schultz |
| 2003/0147922 | A1* | 8/2003 | Capiau et al. ............. 424/244.1 |
| 2004/0191834 | A1 | 9/2004 | Laferriere et al. |
| 2005/0214329 | A1 | 9/2005 | Laferriere |
| 2006/0228380 | A1* | 10/2006 | Hausdorff et al. ......... 424/244.1 |
| 2009/0010959 | A1 | 1/2009 | Biemans et al. |
| 2009/0017059 | A1 | 1/2009 | Biemans et al. |
| 2009/0017072 | A1* | 1/2009 | Biemans et al. ........... 424/244.1 |
| 2009/0041802 | A1 | 2/2009 | Biemans et al. |
| 2010/0034847 | A1* | 2/2010 | Borkowski ............. 424/196.11 |
| 2010/2007492 | | 3/2010 | Biemans et al. |
| 2010/0239604 | A1 | 9/2010 | Biemans et al. |
| 2015/0190521 | A1 | 7/2015 | Biemans et al. |
| 2015/0265702 | A1 | 9/2015 | Biemans et al. |

FOREIGN PATENT DOCUMENTS

| EP | 0497525 | 8/1992 |
| EP | 0594610 | 5/1994 |
| WO | 9006951 | 6/1990 |
| WO | 9508348 | 3/1995 |
| WO | 9629094 | 9/1996 |
| WO | 9851339 | 11/1998 |
| WO | 9915205 | 4/1999 |
| WO | 0010598 | 3/2000 |
| WO | 0037105 | 6/2000 |
| WO | 0056358 | 9/2000 |
| WO | 0056359 | 9/2000 |

(Continued)

OTHER PUBLICATIONS

Sigurdardottir, S.T., et al., *Immune Response to Octavalent Diphtheria- and Tetanus-Conjugated Pneumococcal Vaccines Is Serotype- and Carrier-Specific: The Choice for a Mixed Carrier Vaccine*, Pediatric Infectious Disease Journal, vol. 21, No. 6, pp. 548-554 (2002).
Dagan, R., et al., *Tolerability and Immunogenicity of an Eleven Valent Mixed Carrier Streptococcus pnuemoniae Capsular Polysaccharide-Diphtheria Toxoid or Tetanus Protein Conjugate Vaccine in Finnish and Israeli Infants*, Pediatric Infectious Disease Journal, vol. 23, No. 2, pp. 91-98 (2004).
International Search Report for PCT/EP2008/057999, Priority for U.S. Appl. No. 12/665,350, filed Dec. 18, 2009, Published Aug. 19, 2010 as US 2010/0209450.
International Search Report for PCT/EP2008/057997, Priority for U.S. Appl. No. 12/665,247, filed Dec. 17, 2009, Published Sep. 23, 2010 as US 2010/0239604.
International Search Report for PCT/EP2006/069974, Priority for U.S. Appl. No. 12/097,303, filed Jun. 13, 2008, Published Jan. 8, 2009 as US 2009/0010959, Now Abandoned. (Parent of Co-related case, U.S. Appl. No. 14/729,408).

(Continued)

*Primary Examiner* — S. Devi
(74) *Attorney, Agent, or Firm* — Barbara J. Carter

(57) ABSTRACT

The present invention is in the field of pneumococcal capsular saccharide conjugate vaccines. Specifically, a multivalent *Streptococcus pneumoniae* immunogenic composition is provided with various conjugated capsular saccharides from different *S. pneumoniae* serotypes conjugated to 2 or more different carrier proteins, where the composition comprises serotype 19F capsular saccharide conjugated to diphtheria toxoid (DT) or CRM197, optionally wherein 19F is the only saccharide in the composition conjugated to diphtheria toxoid (DT) or CRM197.

16 Claims, 11 Drawing Sheets

(56) References Cited

FOREIGN PATENT DOCUMENTS

| WO | 0056360 | 9/2000 |
|---|---|---|
| WO | 0200249 | 1/2002 |
| WO | 0222167 | 3/2002 |
| WO | 02080965 | 10/2002 |
| WO | WO 03/028760 | 4/2003 |
| WO | WO 03/051392 | 6/2003 |
| WO | 2005033148 | 4/2005 |
| WO | 2005102384 | 11/2005 |
| WO | 2005105140 | 11/2005 |
| WO | 2006110381 | 10/2006 |
| WO | 2007068907 | 6/2007 |
| WO | WO 2007/071707 | 6/2007 |
| WO | WO 2007/071710 A2 * | 6/2007 |
| WO | WO 2007071711 A2 * | 6/2007 |

OTHER PUBLICATIONS

International Search Report for PCT/EP2006/069977, Priority for U.S. Appl. No. 12/097,631, filed Jun. 16, 2008, Published Jan. 15, 2009 as US 2009/0017059, Now Abandoned. (Parent of Co-related Case, U.S. Appl. No. 14/987,770).

International Search Report for PCT/EP2006/069979, Priority for U.S. Appl. No. 12/097,611, filed Jun. 16, 2008, Published Jan. 15, 2009 as US 2009/0017072, Now Abandoned. (Parent of Co-related Case, U.S. Appl. No. 14/452,312).

Penn, et al., Antibody Responses in Adult Volunteers to Pneumococcal Polysaccharide Types 19F and 19A Administered Singly and in Combination, Infect & Immun 36(3): 1261-1262 (1982).

Chu, et al., Further Studies on the Immunogenicity of Haemophilus influenzae Type b and Pneumococcal Type 6A Polysaccharide-Protein Conjugates, Infect & Immun 40(1): 245-256 (1983).

Peeters, et al., Comparison of four bifunctional reagents for coupling peptides to proteins and the effect of the three moieties on the immunogenicity of the conjugates, J Immunol Methods 120: 133-143 (1989).

Lagergard, et al., Synthesis and immunological properties of conjugates composed of group B *Streptococcus* type III capsular polysaccharide covalently bound to tetanus toxoid, Infect & Immun 58(3): 687-694 (1990).

Lee, et al., Virulence, Immunity, and Vaccine Related to *Streptococcus pneumoniae*, Crit Rev in Microbiol 18(2): 89-114 (1991).

Peeters, et al., Effect of Carrier Priming on Immunogenicity of Saccharide-Protein Conjugate Vaccines, Infect & Immun 59(10): 3504-3510 (1991).

Mitchell, et al., Quantification of Proteinuria: A Re-evaluation of the Protein/Creatinine Ration for Elderly Subjects, Age & Aging 22(6): 443-449 (1993).

Bartoloni, et al., Immunogenicity of meningococcal B polysaccharide conjugated to tetanus toxoid or CRM197 via adipic acid dihydrazide, Vaccine 13(5): 463-470 (1995).

Butler, et al., Serotype Distribution of *Streptococcus pneumoniae* Infections among Preschool Children in the United States. 1978-1994: Implications for Development of a Conjugate Vaccine, J Infect Dis 171: 885-889 (1995).

Kuo, et al., Characterization of a recombinant pneumolysin and its use as a protein carrier for pneumococcal type 18C conjugate vaccines, Infect & Immun 63(7): 2706-2713 (1995).

Laferriere, et al., The synthesis of *Streptococcus pneumoniae* polysaccharide-tetanus toxoid conjugates and the effect of chain length on immunogenicity, Vaccine 15(2): 179-186 (1997).

Michon, et al., Multivalent pneumococcal capsular polysaccharide conjugate vaccines employing genetically detoxified pneumolysin as a carrier protein, Vaccine 16(18): 1732-1741 (1998).

Rennels, et al., Safety and Immunogenicity of Heptavalent Pneumococcal Vaccine Conjugated to CRM197 in United States Infants, Pediatrics 101(4): 604-611 (1998).

Ahman, et al., Dose dependency of antibody response in infants and children to pneumococcal polysaccharides conjugated to tetanus toxoid, Vaccine 17: 2726-2732 (1999).

Anttila, et al., Differences in the avidity of antibodies evoked by four different pneumococcal conjugate vaccines in early childhood, Vaccine 17: 1970-1977 (1999).

Lindberg, Glycoprotein conjugate vaccines, Vaccine 17(Suppl 2): S28-S36 (1999).

Yu, et al., Immunity to Cross-Reactive Serotypes Induced by Pneumococcal Conjugate Vaccines in Infants, J Infect Dis 180(5): 1569-1576 (1999).

Crouch, E.C., Surfactant protein-D and pulmonary host defense, Respiratory Research 1:93-108 (2000).

Hausdorff, et al., Which Pneumococcal Serogroups Cause the Most Invasive Disease: Implications for Conjugate Vaccine Formulation and Use, Part I, Clin Infect Dis 30(1): 100-121 (2000).

Shafer, et al., Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides, Vaccine 18(13): 1273-1281 (2000).

Adamou, et al., Identification and Characterization of a Novel Family of Pneumococcal Proteins That Are Protective against Sepsis, Infect & Immun 69(2): 949-958 (2001).

Eskola, et al., Efficacy of Pneumococcal Conjugate Vaccine Against Acute Otitis Media, N Engl J Med 344(6): 403-409 (2001).

Shen, et al., Group B *Streptococcus* Capsular Polysaccharide-Cholera Toxin B Subunit Conjugate Vaccines Prepared by Different Methods for Intranasal Immunization, Infect & Immun 69(1): 297-306 (2001).

Wuorimaa, et al., Tolerability and immunogenicity of an 11-valent pneumococcal conjugate vaccine in adults, Vaccine 19: 1863-1869 (2001).

Flamaing, et al., *Streptococcus pneumoniae bacteraemia* in Belgium: differential characteristics in children and the elderly population and implications for vaccine use, J Antimicrob Chemother 50: 43-50 (2002).

Biagini, et al., Method for Simultaneous Measurement of Antibodies to 23 Pneumococcal Capsular Polysaccharides, Clin Diag Lab Immunol 10(5): 744-750 (2003).

Jakobsen, et al., Pneumococcal Serotype 19F Conjugate Vaccine Induces Cross-Protective Immunity to Serotype 19A in a Murine Pneumococcal Pneumonia Model, Infect & Immun 71(5): 2956-2959 (2003).

McEllistrem, et al., Epidemiology of Acute Otitis Media Caused by *Streptococcus pneumoniae* Before and After Licensure of the 7-Valent Pneumococcal Protein Conjugate Vaccine, J Infect Dis 188(11): 1679-1684 (2003).

Peeters, et al., Preparation of Polysaccharide-Conjugate Vaccines, Methods in Molecular Med 87: 153-174 (2003).

Clarke, Serotypes and Sequence Types of Pneumococci Causing Invasive Disease in Scotland Prior to the Introduction of Pneumococcal Conjugate Polysaccharide Vaccines, J Clin Microbiol 42(10): 4449-4452 (2004).

Dagan, et al., Reduction of Antibody Response to an 11-Valent Pneumococcal Vaccine Coadministered with a Vaccine Containing Acellular Pertussis Components, Infect & Immun 72(9): 5383-5391 (2004).

Decker, et al., Combination Vaccines, Vaccines, 4th Ed., Chapter 29, pp. 825-861 (2004).

Kaplan, et al., Decrease of Invasive Pneumococcal Infections in Children Among 8 Children's Hospitals in the United States After the Introduction of the 7-Valent Pneumococcal Conjugate Vaccine, Pediatrics 113(3): 443-449 (2004).

Nurkka, et al, Immunogenicity and Safety of the Eleven Valent Pneumococcal Polysaccharide-Protein D Conjugate Vaccine in Infants, Pediatr Infect Dis J, 23(11): 1008-1014 (2004).

Lexau et al., Changing Epidemiology of Invasive Pneumococcal Disease Among Older Adults in the Era of Pediatric Pneumococcal Conjugate Vaccine, JAMA 294(16): 2043-2051 (2005).

McChlery, et al., Clonal analysis of invasive pneumococcal isolates in Scotland and coverage of serotypes by the licensed conjugate polysaccharide pneumococcal vaccine: possible implications for UK vaccine policy, Eur J Clin Microbiol Infect Dis 24: 262-267 (2005).

(56) References Cited

OTHER PUBLICATIONS

Moore, Epidemiology of invasive pneumococcal disease in adults, Centers for Disease Control and Prevention, U.S. Department of Human Health and Services, http://www.fda.gov/ohrms/dockets/ac/05/slides/5-4188s2_3.ppt> pp. 6-8 (2005).

Beall, et al., Pre- and Postvaccination Clonal Compositions of Invasive Pneumococcal Serotypes for Isolates Collected in the United States in 1999, 2001 and 2002, J Clin Microbiol 44(3): 999-1017 (2006).

Prymula, et al., Pneumococcal capsular polysaccharides conjugated to protein D for prevention of acute otitis media caused by both *Streptococcus pneumoniae* and non-typable Haemophilus influenzae: a randomised double-blind efficacy study, Lancet 367: 740-748 (2006).

Whitney, et al., Effectiveness of seven-valent pneumococcal conjugate vaccine against invasive pneumococcal disease: a matched case-control study, LANCET 368: 1495-1502 (2006).

Henckaerts, et al., Validation of a routine opsonophagocytosis assay to predict invasive pneumococcal disease efficacy of conjugate vaccine in children, Vaccine 25(13): 2518-2527 (2007).

Prymula and Schuerman, 10-valent pneumococcal nontypeable Haemophilus influenzae PD conjugate vaccine: Synflorix, Expert Rev Vaccines 8(11): 1479-1500 (2009).

Schuerman, et al., Prevention of otitis media: Now a reality? Vaccine 27: 5748-5754 (2009).

Poolman, et al., Impact of the Conjugation Method on the Immunogenicity of *Streptococcus pneumoniae* Serotype 19F Polysaccharide in Conjugate Vaccines, Clin & Vaccine Immunol 18(2): 327-336 (2011).

De Wals, et al., Invasive pneumococcal diseases in birth cohorts vaccinated with PCV-7 and/or PhiD-CV in the province of Quebec, Canada, Vaccine 30: 1-5 (2012).

Sobanjo, et al., Merck Research Laboratories, North Wales, PA, USA, University of Tampere Medical School, Tampere, Finland, MD Research, Canton, OH, Pediatric Medical Associates, Rydal, PA, USA (2011)—Abstract.

\* cited by examiner

```
                           SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
tccatgacgt tcctgacgtt                                                     20

<210> SEQ ID NO 2
<211> LENGTH: 18
<212> TYPE: DNA
<213> ORGANISM: artificial sequence
<220> FEATURE:
<223> OTHER INFORMATION: oligonucleotide

<400> SEQUENCE: 2
tctcccagcg tgcgccat                                                       18

<210> SEQ ID NO 3
<211> LENGTH: 30
<212> TYPE: DNA
<213> ORGANISM: artificial sequence
<220> FEATURE:
<223> OTHER INFORMATION: oligonucleotide

<400> SEQUENCE: 3
accgatgacg tcgccggtga cggcaccacg                                          30

<210> SEQ ID NO 4
<211> LENGTH: 24
<212> TYPE: DNA
<213> ORGANISM: artificial sequence
<220> FEATURE:
<223> OTHER INFORMATION: oligonucleotide

<400> SEQUENCE: 4
tcgtcgtttt gtcgttttgt cgtt                                                24

<210> SEQ ID NO 5
<211> LENGTH: 20
<212> TYPE: DNA
<213> ORGANISM: artificial sequence
<220> FEATURE:
<223> OTHER INFORMATION: oligonucleotide

<400> SEQUENCE: 5
tccatgacgt tcctgatgct                                                     20

<210> SEQ ID NO 6
<211> LENGTH: 22
<212> TYPE: DNA
<213> ORGANISM: artificial sequence
<220> FEATURE:
<223> OTHER INFORMATION: oligonucleotide

<400> SEQUENCE: 6
tcgacgtttt cggcgcgcgc cg                                                  22
```

```
<210> SEQ ID NO 7
<211> LENGTH: 6
<212> TYPE: PRT
<213> ORGANISM: artificial sequence
<220> FEATURE:
<223> OTHER INFORMATION: S. pneumoniae polyhistidine triad protein (Pht)
      family histidine triad motif
<220> FEATURE:
<221> NAME/KEY: MISC_FEATURE
<222> LOCATION: (2)..(3)
<223> OTHER INFORMATION: X is any amino acid other than His
<220> FEATURE:
<221> NAME/KEY: MISC_FEATURE
<222> LOCATION: (5)..(5)
<223> OTHER INFORMATION: X is any amino acid other than His

<400> SEQUENCE: 7

His Xaa Xaa His Xaa His
1               5

<210> SEQ ID NO 8
<211> LENGTH: 4
<212> TYPE: PRT
<213> ORGANISM: unknown
<220> FEATURE:
<223> OTHER INFORMATION: S. pneumoniae protein having a Type II Signal
      sequence Motif
<220> FEATURE:
<221> NAME/KEY: MISC_FEATURE
<222> LOCATION: (2)..(3)
<223> OTHER INFORMATION: X is any amino acid

<400> SEQUENCE: 8

Leu Xaa Xaa Cys
1

<210> SEQ ID NO 9
<211> LENGTH: 5
<212> TYPE: PRT
<213> ORGANISM: unknown
<220> FEATURE:
<223> OTHER INFORMATION: S. pneumoniae  surface protein Cell Wall
      Anchored motif
<220> FEATURE:
<221> NAME/KEY: MISC_FEATURE
<222> LOCATION: (3)..(3)
<223> OTHER INFORMATION: X is any amino acid

<400> SEQUENCE: 9

Leu Pro Xaa Thr Gly
1               5
```

VACCINE COMPRISING *STREPTOCOCCUS PNEUMONIAE* CAPSULAR POLYSACCHARIDE CONJUGATES

This application is filed pursuant to 35 U.S.C. §371 as a United States National Phase Application of International Patent Application Serial No. PCT/EP2008/057999 filed Jun. 24, 2008, which claims priority to Great Britain Application No. 0712420.9 filed in the United Kingdom on Jun. 26, 2007, Great Britain Application No. 0712428.2 filed in the United Kingdom on Jun. 26, 2007, and Great Britain Application No. 0712435.7 filed in the United Kingdom on Jun. 26, 2007, the contents of which are incorporated herein by reference.

SEQUENCE LISTING

This application contains sequences, listed in an electronic Sequence Listing and filed on Feb. 28, 2012, the contents and sequences of which are hereby incorporated by reference herein.

FIELD OF THE INVENTION

The present invention relates to an improved *Streptococcus pneumoniae* vaccine.

BACKGROUND OF THE INVENTION

Children less than 2 years of age do not mount an immune response to most polysaccharide vaccines, so it has been necessary to render the polysaccharides immunogenic by chemical conjugation to a protein carrier. Coupling the polysaccharide, a T-independent antigen, to a protein, a T-dependent antigen, confers upon the polysaccharide the properties of T dependency including isotype switching, affinity maturation, and memory induction.

However, there can be issues with repeat administration of polysaccharide-protein conjugates, or the combination of polysaccharide-protein conjugates to form multivalent vaccines. For example, it has been reported that a *Haemophilus influenzae* type b polysaccharide (PRP) vaccine using tetanus toxoid (TT) as the protein carrier was tested in a dosage-range with simultaneous immunization with (free) TT and a pneumococcal polysaccharide-TT conjugate vaccine following a standard infant schedule. As the dosage of the pneumococcal vaccine was increased, the immune response to the PRP polysaccharide portion of the Hib conjugate vaccine was decreased, indicating immune interference of the polysaccharide, possibly via the use of the same carrier protein (Dagan et al., Infect Immun. (1998); 66: 2093-2098)

The effect of the carrier-protein dosage on the humoral response to the protein itself has also proven to be multifaceted. In human infants it was reported that increasing the dosage of a tetravalent tetanus toxoid conjugate resulted in a decreased response to the tetanus carrier (Dagan et al. supra). Classical analysis of these effects of combination vaccines have been described as carrier induced epitopic suppression, which is not fully understood, but believed to result from an excess amount of carrier protein (Fattom, Vaccine 17: 126 (1999)). This appears to result in competition for Th-cells, by the B-cells to the carrier protein, and B-cells to the polysaccharide. If the B-cells to the carrier protein predominate, there are not enough Th-cells available to provide the necessary help for the B-cells specific to the polysaccharide. However, the observed immunological effects have been inconsistent, with the total amount of carrier protein in some instances increasing the immune response, and in other cases diminishing the immune response.

Hence there remain technical difficulties in combining multiple polysaccharide conjugates into a single, efficacious, vaccine formulation.

*Streptococcus pneumoniae* is a Gram-positive bacterium responsible for considerable morbidity and mortality (particularly in the young and aged), causing invasive diseases such as pneumonia, bacteraemia and meningitis, and diseases associated with colonisation, such as acute Otitis media. The rate of pneumococcal pneumonia in the US for persons over 60 years of age is estimated to be 3 to 8 per 100,000. In 20% of cases this leads to bacteraemia, and other manifestations such as meningitis, with a mortality rate close to 30% even with antibiotic treatment.

Pneumococcus is encapsulated with a chemically linked polysaccharide which confers serotype specificity. There are 90 known serotypes of pneumococci, and the capsule is the principle virulence determinant for pneumococci, as the capsule not only protects the inner surface of the bacteria from complement, but is itself poorly immunogenic. Polysaccharides are T-independent antigens, and can not be processed or presented on MHC molecules to interact with T-cells. They can however, stimulate the immune system through an alternate mechanism which involves cross-linking of surface receptors on B cells.

It was shown in several experiments that protection against invasive pneumococci disease is correlated most strongly with antibody specific for the capsule, and the protection is serotype specific.

*Streptococcus pneumoniae* is the most common cause of invasive bacterial disease and Otitis media in infants and young children. Likewise, the elderly mount poor responses to pneumococcal vaccines [Roghmann et al., (1987), J. Gerontol. 42:265-270], hence the increased incidence of bacterial pneumonia in this population [Verghese and Berk, (1983) Medicine (Baltimore) 62:271-285].

The major clinical syndromes caused by *S. pneumoniae* are widely recognized and discussed in all standard medical textbooks (Fedson D S, Muscher D M. In: Plotkin S A, Orenstein W A, editors. Vaccines. 4rth edition. PhiladelphiaWB Saunders Co, 2004a: 529-588). For instance, Invasive pneumococcal disease (IPD) is defined as any infection in which *S. pneumoniae* is isolated from the blood or another normally sterile site (Musher D M. *Streptococcus pneumoniae*. In Mandell G L, Bennett J E, Dolin R (eds). Principles and Practice of Infectious diseases (5th ed). New York, Churchill Livingstone, 2001, p2128-2147). Chronic obstructive pulmonary disease (COPD) is recognised as encompassing several conditions (airflow obstruction, chronic bronchitis, bronchiolitis or small airways disease and emphysema) that often coexist. Patients suffer exacerbations of their condition that are usually associated with increased breathlessness, and often have increased cough that may be productive of mucus or purulent sputum (Wilson, Eur Respir J 2001 17:995-1007). COPD is defined physiologically by the presence of irreversible or partially reversible airway obstruction in patients with chronic bronchitis and/or emphysema (Standards for the diagnosis and care of patients with chronic obstructive pulmonary disease. American Thoracic Society. Am J Respir Crit Care Med. 1995 November; 152(5 Pt 2):577-121). Exacerbations of COPD are often caused by bacterial (e.g. pneumococcal) infection (Sethi S, Murphy T F. Bacterial infection in chronic obstructive pulmonary disease in 2000: a state-of-the-art review. Clin Microbiol Rev. 2001 April; 14(2):336-63).

It is thus an object of the present invention to develop an improved formulation of a multiple serotype *Streptococcus pneumoniae* polysaccharide conjugate vaccine.

DESCRIPTION OF THE INVENTION

Figure 1:
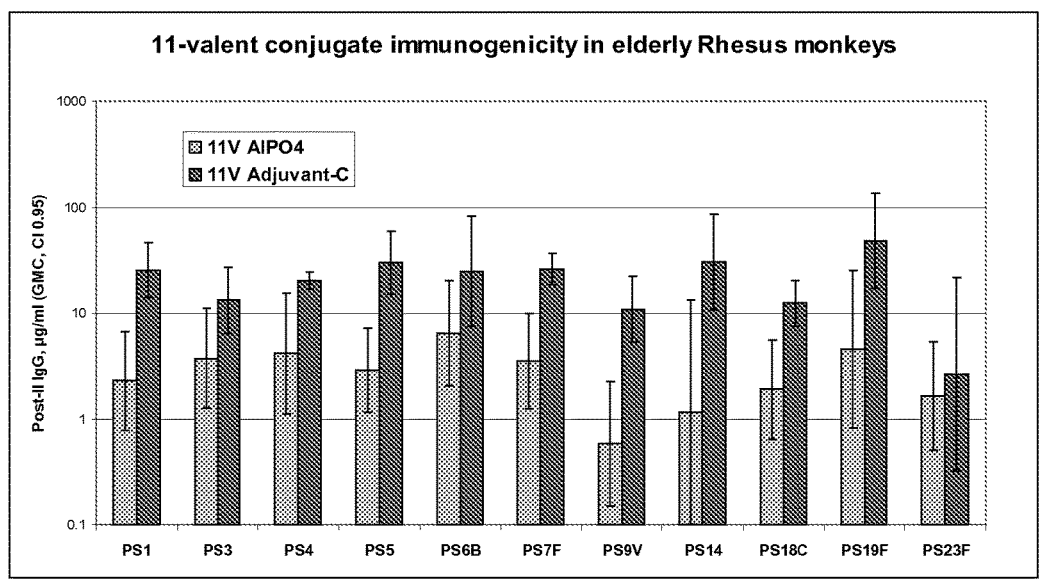
FIG. 1 Conjugate immunogenicity in elderly Rhesus monkeys (post-II anti-PS IgG levels) Bar chart showing 11 valent conjugate immunogenicity in elderly Rhesus monkeys. The lighter bars represent the GMC after two inoculations with 11 valent conjugate in aluminium phosphate adjuvant. The darker bars represent the GMC after two inoculations with 11 valent conjugate in adjuvant C.

The present invention provides an improved *Streptococcus pneumoniae* vaccine comprising 10 or more (e.g. 11, 12, 13, 14, or 15 or more) capsular saccharides from different *S. pneumoniae* serotypes conjugated to 2 or more carrier proteins, wherein the vaccine comprises serotype 19F capsular saccharide conjugated to diphtheria toxoid or CRM197, and 2-8 *S. pneumoniae* capsular saccharides selected from different serotypes conjugated to protein D.

For the purposes of this invention, "immunizing a human host against exacerbations of COPD" or "treatment or prevention of exacerbations of COPD" or "reduction in severity of COPD exacerbations" refers to a reduction in incidence or rate of COPD exacerbations (for instance a reduction in rate of 0.1, 0.5, 1, 2, 5, 10, 20% or more) or a reduction in severity of COPD exacerbations as defined above, for instance within a patient group immunized with the compositions or vaccines of the invention.

Typically the *Streptococcus pneumoniae* vaccine of the present invention will comprise capsular saccharide antigens (preferably conjugated), wherein the saccharides are derived from at least ten serotypes of *S. pneumoniae*. The number of *S. pneumoniae* capsular saccharides can range from 10 different serotypes (or "v", valences) to 23 different serotypes (23v). In one embodiment there are 10, 11, 12, 13, 14 or 15 different serotypes. In another embodiment of the invention, the vaccine may comprise conjugated *S. pneumoniae* saccharides and unconjugated *S. pneumoniae* saccharides. Preferably, the total number of saccharide serotypes is less than or equal to 23. For example, the invention may comprise 10 conjugated serotypes and 13 unconjugated saccharides. In a similar manner, the vaccine may comprise 11, 12, 13, 14, 15 or 16 conjugated saccharides and 12, 11, 10, 9, 8 or 7, respectively, unconjugated saccharides.

The term "selected from different serotypes" means that the capsular saccharides conjugated to protein D are from *S. pneumoniae* serotypes other than 19F.

The immunogenic composition of the invention contains 2-8, 2-7, 2-6, 2-5, 3-5, 4-5, 2-4, 2-3, 3-4 or 2, 3, 4, 5, 6, 7 or 8 capsular saccharide conjugates in which protein D is the carrier protein. For example, saccharide from serotype 1, 3, 4, 5, 6A, 6B, 7F, 9V, 14, 18C, 19A, 19F, 22F or 23F is conjugated to protein D. For example, 2-8, 2-7, 2-6, 2-5, 3-5, 4-5, 2-4, 2-3, 3-4 or 2, 3, 4, 5, 6, 7 or 8 saccharides selected from serotype 1, 3, 4, 5, 6A, 6B, 7F, 9V, 14, 18C, 19A, 19F, 22F and 23F are conjugated to protein D.

In an embodiment, saccharides from at least serotypes 1 and 3, 1 and 4, 1 and 5, 1 and 6A, 1 and 6B, 1 and 7, 1 and 9V, 1 and 14, 1 and 22F, 1 and 23F, 3 and 4, 3 and 5, 3 and 6A, 3 and 6B, 3 and 7F, 3 and 9V, 3 and 14, 3 and 22F, 3 and 23F, 4 and 5, 4 and 6A, 4 and 6B, 4 and 7F, 4 and 9V, 4 and 14, 4 and 22F, 4 and 23F, 5 and 6A, 5 and 6B, 5 and 7F, 5 and 9V, 5 and 14, 5 and 22F, 5 and 23F, 6A and 6B, 6A and 7F, 6A and 9V, 6A and 14, 6A and 22F, 6A and 23F, 6B and 7F, 6B and 9V, 6B and 14, 6B and 22F, 6B and 23F, 7F and 9V, 7F and 14, 7F and 22F, 7F and 23F, 9V and 14, 9V and 22F, 9V and 23F, 14 and 22F, 14 and 23F or 22F and 23F are conjugated to protein D.

In an embodiment, saccharides from at least serotypes 1, 3 and 4; 1, 3 and 5; 1, 3 and 6A; 1, 3 and 6B; 1, 3 and 7F; 1, 3 and 9V; 1, 3 and 14; 3, 4 and 7F; 3, 4 and 5; 3, 4 and 7F; 3, 4 and 9V; 3, 4 and 14; 4, 5 and 7F; 4, 5 and 9V; 4, 5, and 14; 5, 7F and 9V; 5, 7F and 14; 7F, 9V and 14; 1, 3, 4 and 5; 3, 4, 5 and 7F; 4, 5, 7F and 9V; 4, 5, 7F and 14; 4, 5, 9V and 14; 4, 7F, 9V and 14; 5, 7F, 9V and 14; or 4, 5, 7F, 9V and 14 are conjugated to protein D.

In an embodiment, half or a minority of the capsular saccharide conjugates present in the immunogenic composition of the invention contain protein D as carrier protein. For example, in a 10 valent S. pneumoniae vaccine, 2, 3, 4 or 5 of the capsular saccharides from different serotypes are conjugated to protein D. For example, in a 11 valent S. pneumoniae vaccine, 2, 3, 4 or 5 of the capsular saccharides from different serotypes are conjugated to protein D. For example, in a 12 valent S. pneumoniae vaccine, 2, 3, 4, 5 or 6 of the capsular saccharides from different serotypes are conjugated to protein D. For example, in a 13 valent S. pneumoniae vaccine, 2, 3, 4, 5 or 6 of the capsular saccharides from different serotypes are conjugated to protein D. For example, in a 14 valent S. pneumoniae vaccine, 2, 3, 4, 5, 6 or 7 of the capsular saccharides from different serotypes are conjugated to protein D. For example, in a 15 valent S. pneumoniae vaccine, 2, 3, 4, 5, 6 or 7 of the capsular saccharides from different serotypes are conjugated to protein D. For example, in a 16 valent S. pneumoniae vaccine, 2, 3, 4, 5, 6, 7 or 8 of the capsular saccharides from different serotypes are conjugated to protein D. For example, in a 17 valent S. pneumoniae vaccine, 2, 3, 4, 5, 6, 7 or 8 of the capsular saccharides from different serotypes are conjugated to protein D. For example, in a 18 valent S. pneumoniae vaccine, 2, 3, 4, 5, 6, 7, 8 or 9 of the capsular saccharides from different serotypes are conjugated to protein D. For example, in a 19 valent S. pneumoniae vaccine, 2, 3, 4, 5, 6, 7, 8 or 9 of the capsular saccharides from different serotypes are conjugated to protein D. Optionally, the serotypes conjugated to protein D are selected from the groups described above.

In one embodiment the multivalent pneumococcal vaccine of the invention will be selected from the following serotypes 1, 2, 3, 4, 5, 6B, 7F, 8, 9N, 9V, 10A, 11A, 12F, 14, 15, 17F, 18C, 19A, 19F, 20, 22F, 23F and 33F, although it is appreciated that one or two other serotypes could be substituted depending on the age of the recipient receiving the vaccine and the geographical location where the vaccine will be administered, e.g. serotype 6A may be included on the list. For example, a 10-valent vaccine may comprise polysaccharides from serotypes 1, 4, 5, 6B, 7F, 9V, 14, 18C, 19F and 23F. An 11-valent vaccine may also include saccharides from serotype 3. A 12 or 13-valent paediatric (infant) vaccine may also include the 10 or 11 valent formulation supplemented with serotypes 6A and 19A, or 6A and 22F, or 19A and 22F, or 6A and 15, or 19A and 15, or 22F and 15, whereas a 13-valent elderly vaccine may include the 11 valent formulation supplemented with serotypes 19A and 22F, 8 and 12F, or 8 and 15, or 8 and 19A, or 8 and 22F, or 12F and 15, or 12F and 19A, or 12F and 22F, or 15 and 19A, or 15 and 22F. A 14 valent paediatric vaccine may include the 10 valent formulation described above supplemented with serotypes 3, 6A, 19A and 22F; serotypes 6A, 8, 19A and 22F; serotypes 6A, 12F, 19A and 22F; serotypes 6A, 15, 19A and 22F; serotypes 3, 8, 19A and 22F; serotypes 3, 12F, 19A and 22F; serotypes 3, 15, 19A and 22F; serotypes 3, 6A, 8 and 22F; serotypes 3, 6A, 12F and 22F; or serotypes 3, 6A, 15 and 22F.

The composition in one embodiment includes capsular saccharides derived from serotypes 1, 4, 5, 6B, 7F, 9V, 14, 18C, 19F and 23F (preferably conjugated). In a further embodiment of the invention at least 11 saccharide antigens (preferably conjugated) are included, for example capsular saccharides derived from serotypes 1, 3, 4, 5, 6B, 7F, 9V, 14, 18C, 19F and 23F. In a further embodiment of the invention, at least 12 or 13 saccharide antigens are included, for example a vaccine may comprise capsular saccharides derived from serotypes 1, 3, 4, 5, 6A, 6B, 7F, 9V, 14, 18C, 19A, 19F and 23F or capsular saccharides derived from serotypes 1, 3, 4, 5, 6B, 7F, 9V, 14, 18C, 19A, 19F, 22F and 23F, although further saccharide antigens, for example 23 valent (such as serotypes 1, 2, 3, 4, 5, 6B, 7F, 8, 9N, 9V, 10A, 11A, 12F, 14, 15, 17F, 18C, 19A, 19F, 20, 22F, 23F and 33F), are also contemplated by the invention.

The immunogenic composition of the present invention comprises protein D (PD) from *Haemophilus influenzae* (see e.g. EP 0594610 FIG. 9). *Haemophilus influenzae* is a key causative organism of otitis media, and the present inventors have shown that including this protein in a *Streptococcus pneumoniae* vaccine will provide a level of protection against *Haemophilus influenzae* related otitis media (Pyrmula et al Lancet 367; 740-748 (2006)). In one aspect, PD is present as a carrier protein for one or more of the saccharides. In another aspect, protein D could be present in the vaccine composition as a free protein. In a further aspect, protein D is present both as a carrier protein and as free protein. Protein D may be used as a full length protein or as a fragment (WO0056360). In a further aspect, protein D is present as a carrier protein for the majority of the saccharides, for example 6, 7, 8, 9 or more of the saccharides may be conjugated to protein D. In this aspect, protein D may also be present as free protein.

The vaccine of the present invention comprises two or more different types of carrier protein. Each type of carrier protein may act as carrier for more than one saccharide, which saccharides may be the same or different. For example, serotypes 3 and 4 may be conjugated to the same carrier protein, either to the same molecule of carrier protein or to different molecules of the same carrier protein. In one embodiment, two or more different saccharides may be conjugated to the same carrier protein, either to the same molecule of carrier protein or to different molecules of the same carrier protein.

Each *Streptococcus pneumoniae* capsular saccharide may be conjugated to a carrier protein independently selected from the group consisting of TT, DT, CRM197, fragment C of TT, PhtD, PhtDE fusions (particularly those described in WO 01/98334 and WO 03/54007), detoxified pneumolysin and protein D, other than saccharide from serotype 19F which is always conjugated to DT or CRM 197, preferably DT. A more complete list of protein carriers that may be used in the conjugates of the invention is presented below If the protein carrier is the same for 2 or more saccharides in the composition, the saccharides could be conjugated to the same molecule of the protein carrier (carrier molecules having 2 more different saccharides conjugated to it) [see for instance WO 04/083251]. Alternatively the saccharides may each be separately conjugated to different molecules of the protein carrier (each molecule of protein carrier only having one type of saccharide conjugated to it).

The carrier protein conjugated to one or more of the *S. pneumoniae* capsular saccharides in the conjugates present in the immunogenic compositions of the invention is optionally a member of the polyhistidine triad family (Pht) proteins, fragments or fusion proteins thereof. The PhtA, PhtB, PhtD or PhtE proteins may have an amino acid sequence sharing 80%, 85%, 90%, 95%, 98%, 99% or 100% identity with a sequence disclosed in WO 00/37105 or WO 00/39299 (e.g. with amino acid sequence 1-838 or 21-838 of SEQ ID NO: 4 of WO 00/37105 for PhtD). For example, fusion proteins are composed of full length or fragments of 2, 3 or 4 of PhtA, PhtB, PhtD, PhtE. Examples of fusion proteins are PhtA/B, PhtA/D, PhtA/E, PhtB/A, PhtB/D, PhtB/E. PhtD/A. PhtD/B, PhtD/E, PhtE/A, PhtE/B and PhtE/D, wherein the proteins are linked with the first mentioned at the N-terminus (see for example WO01/98334).

Where fragments of Pht proteins are used (separately or as part of a fusion protein), each fragment optionally contains one or more histidine triad motif(s) and/or coiled coil regions of such polypeptides. A histidine triad motif is the portion of polypeptide that has the sequence HxxHxH (SEQ ID NO: 7) where H is histidine and x is an amino acid other than histidine. A coiled coil region is a region predicted by "Coils" algorithm Lupus, A et al (1991) Science 252; 1162-1164. In an embodiment the or each fragment includes one or more histidine triad motif as well as at least one coiled coil region. In an embodiment, the or each fragment contains exactly or at least 2, 3, 4 or 5 histidine triad motifs (optionally, with native Pht sequence between the 2 or more triads, or intra-triad sequence that is more than 50, 60, 70, 80, 90 or 100% identical to a native pneumococcal intra-triad Pht sequence—e.g. the intra-triad sequence shown in SEQ ID NO: 4 of WO 00/37105 for PhtD). In an embodiment, the or each fragment contains exactly or at least 2, 3 or 4 coiled coil regions. In an embodiment a Pht protein disclosed herein includes the full length protein with the signal sequence attached, the mature full length protein with the signal peptide (for example 20 amino acids at N-terminus) removed, naturally occurring variants of Pht protein and immunogenic fragments of Pht protein (e.g. fragments as described above or polypeptides comprising at least 15 or 20 contiguous amino acids from an amino acid sequence in WO00/37105 (SEQ ID NOs 4, 6, 8 or 10) or WO00/39299 (SEQ ID NOs 2, 4, 6, 8, 10 or 14) wherein said polypeptide is capable of eliciting an immune response specific for said amino acid sequence in WO00/37105 or WO00/39299).

In particular, the term "PhtD" as used herein includes the full length protein with the signal sequence attached, the mature full length protein with the signal peptide (for example 20 amino acids at N-terminus) removed, naturally occurring variants of PhtD and immunogenic fragments of PhtD (e.g. fragments as described above or polypeptides comprising at least 15 or 20 contiguous amino acids from a PhtD amino acid sequence in WO00/37105 or WO00/39299 wherein said polypeptide is capable of eliciting an immune response specific for said PhtD amino acid sequence in WO00/37105 or WO00/39299 (e.g. SEQ ID NO: 4 of WO 00/37105 or SEQ ID NO: 14 of WO 00/39299 for PhtD). All forms of PhtD mentioned above can be used in the present invention.

If the protein carrier is the same for 2 or more saccharides in the composition, the saccharides could be conjugated to the same molecule of the protein carrier (carrier molecules having 2 more different saccharides conjugated to it) [see for instance WO 04/083251]. Alternatively the saccharides may each be separately conjugated to different molecules of the protein carrier (each molecule of protein carrier only having one type of saccharide conjugated to it).

Examples of carrier proteins which may be used in the present invention are DT (Diphtheria toxoid), TT (tetanus toxoid) or fragment C of TT, DT CRM197 (a DT mutant) other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711, pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE and fusions of Pht proteins for example PhtDE fusions, PhtBE fusions (WO 01/98334 and WO 03/54007), (Pht A-E are described in more detail below) OMPC (meningococcal outer membrane protein—usually extracted from *N. meningitidis* serogroup B—EP0372501), PorB (from *N. meningitidis*), PD (*Haemophilus influenzae* protein D—see, e.g., EP 0 594 610 B), or immunologically functional equivalents thereof, synthetic peptides (EP0378881, EPO427347), heat shock proteins (WO 93/17712, WO 94/03208), pertussis proteins (WO 98/58668, EPO471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761).

Nurkka et al *Pediatric Infectious Disease Journal.* 23(11): 1008-14, 2004 November described an 11 valent pneumococcal vaccine with all serotypes conjugated to PD. However, the present inventors have shown that opsonophagocytic activity was improved for antibodies induced with conjugates having 19F conjugated to DT compared with 19F conjugated to PD. In addition, the present inventors have shown that a greater cross reactivity to 19A is seen with 19F conjugated to DT. It is therefore a feature of the composition of the present invention that serotype 19F is conjugated to DT or CRM 197. In one aspect, serotype 19F is conjugated to DT. The remaining saccharide serotypes of the immunogenic composition may all be conjugated to one or more carrier proteins that are not DT (i.e. only 19F is conjugated to DT), or may be split between one or more carrier proteins that are not DT and DT itself. In one embodiment, 19F is conjugated to DT or CRM 197 and all of the remaining serotypes are conjugated to PD. In a further embodiment, 19F is conjugated to DT or CRM 197, and the remaining serotypes are split between PD, and TT or DT or CRM 197. In a further embodiment, 19F is conjugated to DT or CRM 197 and no more than one saccharide is conjugated to TT. In one aspect of this embodiment, said one saccharide is 18C or 12F. In a further embodiment, 19F is conjugated to DT or CRM 197 and no more than two saccharides are conjugated to TT. In a further embodiment, 19F is conjugated to DT or CRM 197, and the remaining serotypes are split between PD, TT and DT or CRM 197. In a further embodiment, 19F is conjugated to DT or CRM 197, and the remaining serotypes are split between PD, TT and pneumolysin. In a further embodiment, 19F is conjugated to DT or CRM 197, and the remaining serotypes are split between PD, TT and CRM 197. In a further embodiment, 19F is conjugated to DT or CRM197 and the remaining serotypes are split between PD, TT, pneumolysin and optionally PhtD or PhtD/E fusion protein. In a further embodiment, 19F is conjugated to DT or CRM197, 19A is conjugated to pneumolysin or TT, one (two or three) further saccharide(s) is conjugated to TT, one further saccharide is conjugated to PhtD or PhtD/E and all further saccharides are conjugated to PD. In a further embodiment 19F is conjugated to DT or CRM197, 19A is conjugated to pneumolysin, one (two or three) further saccharide(s) is conjugated to TT, one further saccharide is conjugated to pneumolysin, 2 further saccharides are conjugated to PhtD or PhtD/E and all further saccharides are conjugated to PD.

The term "saccharide" throughout this specification may indicate polysaccharide or oligosaccharide and includes both. Polysaccharides are isolated from bacteria and may be sized to some degree by known methods (see for example EP497524 and EP497525) and preferably by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides Capsular polysaccharides of *Streptococcus pneumoniae* comprise repeating oligosaccharide units which may contain up to 8 sugar residues. For a review of the oligosaccharide units for the key *Streptococcus pneumoniae* serotypes see JONES, Christopher. Vaccines based on the cell surface carbohydrates of pathogenic bacteria. *An. Acad. Bras. Ciênc., June* 2005, vol. 77, no. 2, p. 293-324. Table II ISSN 0001-3765. In one embodiment, a capsular saccharide antigen may be a full length polysaccharide, however in others it may be one oligosaccharide unit, or a shorter than native length saccharide chain of repeating oligosaccharide units. In one embodiment, all of the saccharides present in the vaccine are polysaccharides. Full length polysaccharides may be "sized" i.e. their size may be reduced by various methods such as acid hydrolysis treatment, hydrogen peroxide treatment, sizing by EMULSIFLEX® followed by a hydrogen peroxide treatment to generate oligosaccharide fragments or microfluidization.

The inventors have also noted that the focus of the art has been to use oligosaccharides for ease of conjugate production. The inventors have found that by using native or slightly sized polysaccharide conjugates, one or more of the following advantages may be realised: 1) a conjugate having high immunogenicity which is filterable, 2) the ratio of polysaccharide to protein in the conjugate can be altered such that the ratio of polysaccharide to protein (w/w) in the conjugate may be increased (which can have an effect on the carrier suppression effect), 3) immunogenic conjugates prone to hydrolysis may be stabilised by the use of larger saccharides for conjugation. The use of larger polysaccharides can result in more cross-linking with the conjugate carrier and may lessen the liberation of free saccharide from the conjugate. The conjugate vaccines described in the prior art tend to depolymerise the polysaccharides prior to conjugation in order to improve conjugation. The present inventors have found that saccharide conjugate vaccines retaining a larger size of saccharide can provide a good immune response against pneumococcal disease.

The immunogenic composition of the invention may thus comprise one or more saccharide conjugates wherein the average size (e.g. weight-average molecular weight; $M_w$) of each saccharide before conjugation is above 80 kDa, 100 kDa, 200 kDa, 300 kDa, 400 kDa, 500 kDa or 1000 kDa. In one embodiment one or more saccharide conjugates of the invention should have an average size of saccharide pre-conjugation of 50-1600, 80-1400, 100-1000, 150-500, or 200-400 kDa (note that where average size is $M_w$, 'kDa' units should be replaced herein with '$\times 10^3$'). In one embodiment the conjugate post conjugation should be readily filterable through a 0.2 micron filter such that a yield of more than 50, 60, 70, 80, 90 or 95% is obtained post filtration compared with the pre filtration sample.

For the purposes of the invention, "native polysaccharide" refers to a saccharide that has not been subjected to a process (e.g. post-purification), the purpose of which is to reduce the size of the saccharide. A polysaccharide can become slightly reduced in size during normal purification procedures. Such a saccharide is still native. Only if the polysaccharide has been subjected to sizing techniques would the polysaccharide not be considered native. The size of a native polysaccharide is for example between 250 kDa-2,000 kDa, 400-1,500 kDa, 750 kDa-1,250 kDa, 300 kDa-600 kDa, 500-1,000 kDa, or 1,000-1,500 kDa with different serotypes having different sizes of native polysaccharide as will be appreciated by the skilled person.

For the purposes of the invention, "sized by a factor up to ×2" means that the saccharide is subject to a process intended to reduce the size of the saccharide but to retain a size more than half the size of the native polysaccharide. ×3, ×4 etc. are to be interpreted in the same way i.e. the saccharide is subject to a process intended to reduce the size of the polysaccharide but to retain a size more than a third, a quarter etc. the size of the native polysaccharide.

In an aspect of the invention, the immunogenic composition comprises *Streptococcus pneumoniae* saccharides from at least 10 serotypes conjugated to a carrier protein, wherein at least 1, 2, 3, 4, 5, 6, 7, 8, 9 or each *S. pneumoniae* saccharide is native polysaccharide.

In an aspect of the invention, the immunogenic composition comprises *Streptococcus pneumoniae* saccharides from at least 10 serotypes conjugated to a carrier protein, wherein at least 1, 2, 3, 4, 5, 6, 7, 8, 9 or each *S. pneumoniae* saccharide is sized by a factor up to ×2, ×3, ×4, ×5, ×6, ×7, ×8, ×9 or ×10. In one embodiment of this aspect, the majority of the saccharides, for example 6, 7, 8 or more of the saccharides are sized by a factor up to ×2, ×3, ×4, ×5, ×6, ×7, ×8, ×9 or ×10.

The molecular weight or average molecular weight (or size) of a saccharide herein refers to the weight-average molecular weight ($M_w$) of the saccharide measured prior to conjugation and is measured by MALLS.

The MALLS technique is well known in the art and is typically carried out as described in example 2. For MALLS analysis of pneumococcal saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm).

In an embodiment the *S. pneumoniae* saccharides are native polysaccharides or native polysaccharides which have been reduced in size during a normal extraction process.

In an embodiment, the *S. pneumoniae* saccharides are sized by mechanical cleavage, for instance by microfluidisation or sonication. Microfluidisation and sonication have the advantage of decreasing the size of the larger native polysaccharides sufficiently to provide a filterable conjugate. Sizing is by a factor of no more than ×20, ×10, ×8, ×6, ×5, ×4, ×3 or ×2.

In an embodiment, the immunogenic composition comprises S. pneumoniae conjugates that are made from a mixture of native polysaccharides and saccharides that are sized by a factor of no more than ×20. In one aspect of this embodiment, the majority of the saccharides, for example 6, 7, 8 or more of the saccharides are sized by a factor of up to ×2, ×3, ×4, ×5 or ×6.

In an embodiment, the *Streptococcus pneumoniae* saccharide is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH. Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. No. 4,673,574, U.S. Pat. No. 4,808,700), hexane diamine and 6-aminocaproic acid (U.S. Pat. No. 4,459,286). In an embodiment, ADH is used as a linker for conjugating saccharide from serotype 18C. In an embodiment, ADH is used as a linker for conjugating saccharide from serotype 22F.

The saccharide conjugates present in the immunogenic compositions of the invention may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or STAB, or SIA, or SBAP). Preferably, the cyanate ester (optionally made by CDAP chemistry) is coupled with hexane diamine or ADH and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094

Other suitable techniques use carbodiimides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction of with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid dihydrazide (ADH) to the protein carrier by Carbodiimide condensation (Chu C. et al Infect. Immunity, 1983 245 256), for example using EDAC.

In an embodiment, a hydroxyl group (preferably an activated hydroxyl group for example a hydroxyl group activated to make a cyanate ester [e.g. with CDAP]) on a saccharide is linked to an amino or carboxylic group on a protein either directly or indirectly (through a linker). Where a linker is present, a hydroxyl group on a saccharide is preferably linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the pneumococcal capsular saccharide(s) is conjugated to the linker first before the linker is conjugated to the carrier protein. Alternatively the linker may be conjugated to the carrier before conjugation to the saccharide.

A combination of techniques may also be used, with some saccharide-protein conjugates being prepared by CDAP, and some by reductive amination.

In general the following types of chemical groups on a protein carrier can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:

Saccharide-OH+CNBr or CDAP----->cyanate ester+NH2-Prot---->conjugate

Saccharide-aldehyde+NH2-Prot---->Schiff base+NaCNBH3---->conjugate

Saccharide-COOH+NH2-Prot+EDAC---->conjugate

Saccharide-NH2+COOH-Prot+EDAC---->conjugate

Indirect Coupling Via Spacer (Linker) Approaches:

Saccharide-OH+CNBr or CDAP--->cyanate ester+NH2----NH2---->saccharide----NH2+COOH-Prot+EDAC----->conjugate Saccharide-OH+CNBr or CDAP---->cyanate ester+NH2-----SH----->saccharide----SH+SH-Prot (native Protein with an exposed cysteine or obtained after modification of amino groups of the protein by SPDP for instance)-----> saccharide-S—S-Prot Saccharide-OH+CNBr or CDAP--->cyanate ester+NH2----SH------->saccharide----SH+maleimide-Prot (modification of amino groups)---->conjugate Saccharide-OH+CNBr or CDAP--->cyanate ester+NH2-----SH--->Saccharide-SH+haloacetylated-Prot----> Conjugate Saccharide-COOH+EDAC+NH2-----NH2--->saccharide------NH2+EDAC+COOH-Prot---->conjugate Saccharide-COOH+EDAC+NH2----SH----->saccharide----SH+SH-Prot (native Protein with an exposed cysteine or obtained after modification of amino groups of the protein by SPDP for instance)----->saccharide-S—S-Prot Saccharide-COOH+EDAC+NH2----SH----->saccharide----SH+maleimide-Prot (modification of amino groups)---->conjugate Saccharide-COOH+EDAC+NH2----SH--->Saccharide-SH+haloacetylated-Prot---->Conjugate Saccharide-Aldehyde+NH2-----NH2---->saccharide---NH2+EDAC+COOH-Prot---->conjugate Note: instead of EDAC above, any suitable carbodiimide may be used.

In summary, the types of protein carrier chemical group that may be generally used for coupling with a saccharide are amino groups (for instance on lysine residues), COOH groups (for instance on aspartic and glutamic acid residues) and SH groups (if accessible) (for instance on cysteine residues.

Preferably the ratio of carrier protein to *S. pneumoniae* saccharide is between 1:5 and 5:1; e.g. between 1:0.5-4:1, 1:1-3.5:1, 1.2:1-3:1, 1.5:1-2.5:1; e.g. between 1:2 and 2.5:1; 1:1 and 2:1 (w/w). In an embodiment, the majority of the conjugates, for example 6, 7, 8, 9 or more of the conjugates have a ratio of carrier protein to saccharide that is greater than 1:1, for example 1.1:1, 1.2:1, 1.3:1, 1.4:1, 1.5:1 or 1.6:1.

In an embodiment, at least one *S. pneumoniae* saccharide is conjugated to a carrier protein via a linker using CDAP and EDAC. For example, 18C or 22F may be conjugated to a protein via a linker (for example those with two hydrazino groups at its ends such as ADH) using CDAP and EDAC as described above. When a linker is used, CDAP may be used to conjugate the saccharide to a linker and EDAC may then be used to conjugate the linker to a protein or, alternatively EDAC may be used first to conjugate the linker to the protein, after which CDAP may be used to conjugate the linker to the saccharide.

In general, the immunogenic composition of the invention may comprise a dose of each saccharide conjugate between 0.1 and 20 µg, 1 and 10 µg or 1 and 3 µg of saccharide.

In an embodiment, the immunogenic composition of the invention contains each *S. pneumoniae* capsular saccharide at a dose of between 0.1-20 µg; 0.5-10 µg; 0.5-5 µg or 1-3 µg of saccharide. In an embodiment, capsular saccharides may be present at different dosages, for example some capsular saccharides may be present at a dose of around or exactly 1 µg or some capsular saccharides may be present at a dose of around or exactly 3 µg. In an embodiment, saccharides from serotypes 3, 18C and 19F (or 4, 18C and 19F) are present at a higher dose than other saccharides. In one aspect of this embodiment, serotypes 3, 18C and 19F (or 4, 18C and 19F) are present at a dose of around or exactly 3 µg whilst other saccharides in the immunogenic composition are present at a dose of around or exactly 1 µg.

"Around" or "approximately" are defined as within 10% more or less of the given figure for the purposes of the invention.

In an embodiment, at least one of the *S. pneumoniae* capsular saccharides is directly conjugated to a carrier protein (e.g. using one of the chemistries described above). Preferably the at least one of the *S. pneumoniae* capsular saccharides is directly conjugated by CDAP. In an embodiment, the majority of the capsular saccharides for example 5, 6, 7, 8, 9 or more are directly linked to the carrier protein by CDAP (see WO 95/08348 and WO 96/29094)

The immunogenic composition may comprise *Streptococcus pneumoniae* proteins, herein termed *Streptococcus pneumoniae* proteins of the invention. Such proteins may be used as carrier proteins, or may be present as free proteins, or may be present both as carrier proteins and as free proteins. The *Streptococcus pneumoniae* proteins of the invention are either surface exposed, at least during part of the life cycle of the pneumococcus, or are proteins which are secreted or released by the pneumococcus. Preferably the proteins of the invention are selected from the following categories, such as proteins having a Type II Signal sequence motif of LXXC (SEQ ID NO: 8—where X is any amino acid, e.g., the polyhistidine triad family (PhtX)), choline binding proteins (CbpX), proteins having a Type I Signal sequence motif (e.g., Sp101), proteins having a LPXTG motif (SEQ ID NO: 9—where X is any amino acid, e.g., Sp128, Sp130), and toxins (e.g., Ply). Preferred examples within these categories (or motifs) are the following proteins, or immunologically functional equivalents thereof.

In one embodiment, the immunogenic composition of the invention comprises at least 1 protein selected from the group consisting of the Poly Histidine Triad family (PhtX), Choline Binding Protein family (CbpX), CbpX truncates, LytX family, LytX truncates, CbpX truncate-LytX truncate chimeric proteins (or fusions), pneumolysin (Ply), PspA, PsaA, Sp128, Sp101, Sp130, Sp125 and Sp133. In a further embodiment, the immunogenic composition comprises 2 or more proteins selected from the group consisting of the Poly Histidine Triad family (PhtX), Choline Binding Protein family (CbpX), CbpX truncates, LytX family, LytX truncates, CbpX truncate-LytX truncate chimeric proteins (or fusions), pneumolysin (Ply), PspA, PsaA, and Sp128. In one more embodiment, the immunogenic composition comprises 2 or more proteins selected from the group consisting of the Poly Histidine Triad family (PhtX), Choline Binding Protein family (CbpX), CbpX truncates, LytX family, LytX truncates, CbpX truncate-LytX truncate chimeric proteins (or fusions), pneumolysin (Ply), and Sp128.

The Pht (Poly Histidine Triad) family comprises proteins PhtA, PhtB, PhtD, and PhtE. The family is characterized by a lipidation sequence, two domains separated by a proline-rich region and several histidine triads, possibly involved in metal or nucleoside binding or enzymatic activity, (3-5) coiled-coil regions, a conserved N-terminus and a heterogeneous C terminus. It is present in all strains of pneumococci tested. Homologous proteins have also been found in other Streptococci and *Neisseria*. In one embodiment of the invention, the Pht protein of the invention is PhtD. It is understood, however, that the terms Pht A, B, D, and E refer to proteins having sequences disclosed in the citations below as well as naturally-occurring (and man-made) variants thereof that have a sequence homology that is at least 90% identical to the referenced proteins. Preferably it is at least 95% identical and most preferably it is 97% identical.

With regards to the PhtX proteins, PhtA is disclosed in WO 98/18930, and is also referred to Sp36. As noted above, it is a protein from the polyhistidine triad family and has the type II signal motif of LXXC (SEQ ID NO: 8). PhtD is disclosed in WO 00/37105, and is also referred to Sp036D. As noted above, it also is a protein from the polyhistidine triad family and has the type II LXXC signal motif (SEQ ID NO: 8). PhtB is disclosed in WO 00/37105, and is also referred to Sp036B. Another member of the PhtB family is the C3-Degrading Polypeptide, as disclosed in WO 00/17370. This protein also is from the polyhistidine triad family and has the type II LXXC signal motif (SEQ ID NO: 8). A preferred immunologically functional equivalent is the protein Sp42 disclosed in WO 98/18930. A PhtB truncate (approximately 79 kD) is disclosed in WO99/15675 which is also considered a member of the PhtX family. PhtE is disclosed in WO00/30299 and is referred to as BVH-3. Where any Pht protein is referred to herein, it is meant that immunogenic fragments or fusions thereof of the Pht protein can be used. For example, a reference to PhtX includes immunogenic fragments or fusions thereof from any Pht protein. A reference to PhtD or PhtB is also a reference to PhtDE or PhtBE fusions as found, for example, in WO0198334.

Pneumolysin is a multifunctional toxin with a distinct cytolytic (hemolytic) and complement activation activities (Rubins et al., Am. Respi. Cit Care Med, 153:1339-1346 (1996)). The toxin is not secreted by pneumococci, but it is released upon lysis of pneumococci under the influence of autolysin. Its effects include e.g., the stimulation of the production of inflammatory cytokines by human monocytes, the inhibition of the beating of cilia on human respiratory epithelial, and the decrease of bactericidal activity and migration of neutrophils. The most obvious effect of pneumolysin is in the lysis of red blood cells, which involves binding to cholesterol. Because it is a toxin, it needs to be detoxified (i.e., non-toxic to a human when provided at a dosage suitable for protection) before it can be administered in vivo. Expression and cloning of wild-type or native pneumolysin is known in the art. See, for example, Walker et al. (Infect Immun, 55:1184-1189 (1987)), Mitchell et al. (Biochim Biophys Acta, 1007:67-72 (1989) and Mitchell et al (NAR, 18:4010 (1990)). Detoxification of ply can be conducted by chemical means, e.g., subject to formalin or glutaraldehyde treatment or a combination of both (WO 04081515, PCT/EP2005/010258). Such methods are well known in the art for various toxins. Alternatively, ply can be genetically detoxified. Thus, the invention encompasses derivatives of pneumococcal proteins which may be, for example, mutated proteins. The term "mutated" is used herein to mean a molecule which has undergone deletion, addition or substitution of one or more amino acids using well known techniques for site directed mutagenesis or any other conventional method. For example, as described above, a mutant ply protein may be altered so that it is biologically inactive whilst still maintaining its immunogenic epitopes, see, for example, WO90/06951, Berry et al. (Infect Immun, 67:981-985 (1999)) and WO99/03884.

As used herein, it is understood that the term "Ply" refers to mutated or detoxified pneumolysin suitable for medical use (i.e., non toxic).

Concerning the Choline Binding Protein family (CbpX), members of that family were originally identified as pneumococcal proteins that could be purified by choline-affininty chromatography. All of the choline-binding proteins are non-covalently bound to phosphorylcholine moieties of cell wall teichoic acid and membrane-associated lipoteichoic acid. Structurally, they have several regions in common over the entire family, although the exact nature of the proteins (amino acid sequence, length, etc.) can vary. In general, choline binding proteins comprise an N terminal region (N), conserved repeat regions (R1 and/or R2), a proline rich region (P) and a conserved choline binding region (C), made up of multiple repeats, that comprises approximately one half of the protein. As used in this application, the term "Choline Binding Protein family (CbpX)" is selected from the group consisting of Choline Binding Proteins as identified in WO97/41151, PbcA, SpsA, PspC, CbpA, CbpD, and CbpG. CbpA is disclosed in WO97/41151. CbpD and CbpG are disclosed in WO00/29434. PspC is disclosed in WO97/09994. PbcA is disclosed in WO98/21337.SpsA is a Choline binding protein disclosed in WO 98/39450. Preferably the Choline Binding Proteins are selected from the group consisting of CbpA, PbcA, SpsA and PspC.

Another preferred embodiment is CbpX truncates wherein "CbpX" is defined above and "truncates" refers to CbpX proteins lacking 50% or more of the Choline binding region (C). Preferably such proteins lack the entire choline binding region. More preferably, the such protein truncates lack (i) the choline binding region and (ii) a portion of the N-terminal half of the protein as well, yet retain at least one repeat region (R1 or R2). More preferably still, the truncate has 2 repeat regions (R1 and R2). Examples of such preferred embodiments are NR1xR2 and R1xR2 as illustrated in WO99/51266 or WO99/51188, however, other choline binding proteins lacking a similar choline binding region are also contemplated within the scope of this invention.

The LytX family is membrane associated proteins associated with cell lysis. The N-terminal domain comprises choline binding domain(s), however the LytX family does not have all the features found in the CbpA family noted above and thus for the present invention, the LytX family is considered distinct from the CbpX family. In contrast with the CbpX family, the C-terminal domain contains the catalytic domain of the LytX protein family. The family comprises LytA, B and C. With regards to the LytX family, LytA is disclosed in Ronda et al., Eur J Biochem, 164:621-624 (1987). LytB is disclosed in WO 98/18930, and is also referred to Sp46. LytC is also disclosed in WO 98/18930, and is also referred to Sp91. A preferred member of that family is LytC.

Another preferred embodiment are LytX truncates wherein "LytX" is defined above and "truncates" refers to LytX proteins lacking 50% or more of the Choline binding region. Preferably such proteins lack the entire choline binding region. Yet another preferred embodiment of this invention are CbpX truncate-LytX truncate chimeric proteins (or fusions). Preferably this comprises NR1xR2 (or R1xR2) of CbpX and the C-terminal portion (Cterm, i.e., lacking the choline binding domains) of LytX (e.g., LytC-Cterm or Sp91Cterm). More preferably CbpX is selected from the group consisting of CbpA, PbcA, SpsA and PspC. More preferably still, it is CbpA. Preferably, LytX is LytC (also referred to as Sp91). Another embodiment of the present invention is a PspA or PsaA truncates lacking the choline binding domain (C) and expressed as a fusion protein with LytX. Preferably, LytX is LytC.

With regards to PsaA and PspA, both are know in the art. For example, PsaA and transmembrane deletion variants thereof have been described by Berry & Paton, Infect Immun 1996 December; 64(12):5255-62. PspA and transmembrane deletion variants thereof have been disclosed in, for example, U.S. Pat. No. 5,804,193, WO 92/14488, and WO 99/53940.

Sp128 and Sp130 are disclosed in WO00/76540. Sp125 is an example of a pneumococcal surface protein with the Cell Wall Anchored motif of LPXTG (SEQ ID NO: 9—where X is any amino acid). Any protein within this class of pneumococcal surface protein with this motif has been found to be useful within the context of this invention, and is therefore considered a further protein of the invention. Sp125 itself is disclosed in WO 98/18930, and is also known as ZmpB—a zinc metalloproteinase. Sp101 is disclosed in WO 98/06734 (where it has the reference # y85993). It is characterized by a Type I signal sequence. Sp133 is disclosed in WO 98/06734 (where it has the reference # y85992). It is also characterized by a Type I signal sequence.

Examples of preferred *Moraxella catarrhalis* protein antigens which can be included in a combination vaccine (especially for the prevention of otitis media) are: OMP106 [WO 97/41731 (Antex) & WO 96/34960 (PMC)]; OMP21 or fragments thereof (WO 0018910); LbpA &/or LbpB [WO 98/55606 (PMC)]; TbpA &/or TbpB [WO 97/13785 & WO 97/32980 (PMC)]; CopB [Helminen M E, et al. (1993) Infect. Immun. 61:2003-2010]; UspA1 and/or UspA2 [WO 93/03761 (University of Texas)]; OmpCD; HasR (PCT/EP99/03824); PilQ (PCT/EP99/03823); OMP85 (PCT/EP00/01468); lipo06 (GB 9917977.2); lipo10 (GB 9918208.1); lipo11 (GB 9918302.2); lipo18 (GB 9918038.2); P6 (PCT/EP99/03038); D15 (PCT/EP99/03822); OmplA1 (PCT/EP99/06781); Hly3 (PCT/EP99/03257); and OmpE. Examples of non-typeable *Haemophilus influenzae* antigens or fragments thereof which can be included in a combination vaccine (especially for the prevention of otitis media) include: Fimbrin protein [(U.S. Pat. No. 5,766,608—Ohio State Research Foundation)] and fusions comprising peptides therefrom [eg LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and/or TbpB; Hia; Hsf; Hin47; Hif; Hmw1; Hmw2; Hmw3; Hmw4; Hap; D15 (WO 94/12641); P2; and P5 (WO 94/26304).

The proteins of the invention may also be beneficially combined. By combined is meant that the immunogenic composition comprises all of the proteins from within the following combinations, either as carrier proteins or as free proteins or a mixture of the two. For example, in a combination of two proteins as set out hereinafter, both proteins may be used as carrier proteins, or both proteins may be present as free proteins, or both may be present as carrier and as free protein, or one may be present as a carrier protein and a free protein whilst the other is present only as a carrier protein or only as a free protein, or one may be present as a carrier protein and the other as a free protein. Where a combination of three proteins is given, similar possibilities exist. Preferred combinations include, but are not limited to, PhtD+NR1×R2, PhtD+NR1×R2-Sp91Cterm chimeric or fusion proteins, PhtD+Ply, PhtD+Sp128, PhtD+PsaA, PhtD+PspA, PhtA+NR1×R2, PhtA+NR1×R2-Sp91Cterm chimeric or fusion proteins, PhtA+Ply, PhtA+Sp128, PhtA+PsaA, PhtA+PspA, NR1×R2+LytC, NR1×R2+PspA, NR1×R2+PsaA, NR1×R2+Sp128, R1×R2+LytC, R1×R2+PspA, R1×R2+PsaA, R1×R2+Sp128, R1×R2+PhtD, R1×R2+PhtA. Preferably, NR1×R2 (or R1×R2) is from CbpA or PspC. More preferably it is from CbpA. Other combinations include 3 protein combinations such as PhtD+NR1×R2+Ply, and PhtA+NR1×R2+PhtD. In one embodiment, the vaccine composition comprises detoxified pneumolysin and PhtD or PhtDE as carrier proteins. In a further embodiment, the vaccine composition comprises detoxified pneumolysin and PhtD or PhtDE as free proteins.

The present invention further provides a vaccine containing the immunogenic compositions of the invention and a pharmaceutically acceptable excipient.

The vaccines of the present invention may be adjuvanted, particularly when intended for use in an elderly population but also for use in infant populations. Suitable adjuvants include an aluminum salt such as aluminum hydroxide gel or aluminum phosphate or alum, but may also be a salt of calcium, magnesium, iron or zinc, or may be an insoluble suspension of acylated tyrosine, or acylated sugars, cationically or anionically derivatized saccharides, or polyphosphazenes.

It is preferred that the adjuvant be selected to be a preferential inducer of a TH1 type of response. Such high levels of Th1-type cytokines tend to favour the induction of cell mediated immune responses to a given antigen, whilst high levels of Th2-type cytokines tend to favour the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. (Annual Review of Immunology, 7, p145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1].

An enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO0226757 and WO03507822) are also preferential inducers of a TH1 response and are suitable for use in the present invention.

Particular adjuvants are those selected from the group of metal Salts, oil in water emulsions, Toll like receptors agonist, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof.

An adjuvant that can be used with the vaccine compositions of the invention are bleb or outer membrane vesicle preparations from Gram negative bacterial strains such as those taught by WO02/09746—particularly *N. meningitidis* blebs. Adjuvant properties of blebs can be improved by retaining LOS (lipooligosacccharide) on its surface (e.g. through extraction with low concentrations of detergent [for instanct 0-0.1% deoxycholate]). LOS can be detoxified through the msbB(-) or htrB(-) mutations discussed in WO02/09746. Adjuvant properties can also be improved by retaining PorB (and optionally removing PorA) from meningococcal blebs. Adjuvant properties can also be improved by truncating the outer core saccharide structure of LOS on meningococcal blebs—for instance via the IgtB(-) mutation discussed in WO2004/014417. Alternatively, the aforementioned LOS (e.g. isolated from a msbB(-) and/or IgtB(-) strain) can be purified and used as an adjuvant in the compositions of the invention.

A further adjuvant which may be used with the compositions of the invention may be selected from the group: a saponin, lipid A or a derivative thereof, an immunostimulatory oligonucleotide, an alkyl glucosaminide phosphate, an oil in water emulsion or combinations thereof. A further preferred adjuvant is a metal salt in combination with another adjuvant. It is preferred that the adjuvant is a Toll like receptor agonist in particular an agonist of a Toll like receptor 2, 3, 4, 7, 8 or 9, or a saponin, in particular Qs21. It is further preferred that the adjuvant system comprises two or more adjuvants from the above list. In particular the combinations preferably contain a saponin (in particular Qs21) adjuvant and/or a Toll like receptor 9 agonist such as a CpG containing immunostimulatory oligonucleotide. Other preferred combinations comprise a saponin (in particular QS21) and a Toll like receptor 4 agonist such as monophosphoryl lipid A or its 3 deacylated derivative, 3 D—MPL, or a saponin (in particular QS21) and a Toll like receptor 4 ligand such as an alkyl glucosaminide phosphate.

Particularly preferred adjuvants are combinations of 3D-MPL and QS21 (EP 0 671 948 B1), oil in water emulsions comprising 3D-MPL and QS21 (WO 95/17210, WO 98/56414), or 3D-MPL formulated with other carriers (EP 0 689 454 B1). Other preferred adjuvant systems comprise a combination of 3 D MPL, QS21 and a CpG oligonucleotide as described in U.S. Pat. No. 6,558,670, U.S. Pat. No. 6,544,518.

In an embodiment the adjuvant is (or comprises) a Toll like receptor (TLR) 4 ligand, preferably an agonist such as a lipid A derivative particularly monophosphoryl lipid A or more particularly 3 Deacylated monophoshoryl lipid A (3 D—MPL).

3 D—MPL is available from GlaxoSmithKline Biologicals North America and primarily promotes CD4+ T cell responses with an IFN-g (Th1) phenotype. It can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3 D-MPL is used. Small particle 3 D-MPL has a particle size such that it may be sterile-filtered through a 0.22 µm filter. Such preparations are described in International Patent Application No. WO 94/21292. Synthetic derivatives of lipid A are known and thought to be TLR 4 agonists including, but not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3--[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-,9R)-3-[(R)-dodecanoyloxytradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

Another preferred immunostimulant for use in the present invention is Quil A and its derivatives. Quil A is a saponin preparation isolated from the South American tree *Quilaja Saponaria* Molina and was first described as having adjuvant activity by Dalsgaard et al. in 1974 ("Saponin adjuvants", Archiv. für die gesamte Virusforschung, Vol. 44, Springer Verlag, Berlin, p243-254). Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina which induces CD8+ cytotoxic T cells (CTLs), Th1 cells and a predominant IgG2a antibody response and is a preferred saponin in the context of the present invention.

Particular formulations of QS21 have been described which are particularly preferred, these formulations further comprise a sterol (WO96/33739). The saponins forming part of the present invention may be separate in the form of micelles, mixed micelles (preferentially, but not exclusively with bile salts) or may be in the form of ISCOM matrices (EP 0 109 942 B1), liposomes or related colloidal structures such as worm-like or ring-like multimeric complexes or lipidic/layered structures and lamellae when formulated with cholesterol and lipid, or in the form of an oil in water emulsion (for example as in WO 95/17210). The saponins may preferably be associated with a metallic salt, such as aluminium hydroxide or aluminium phosphate (WO 98/15287).

Preferably, the saponin is presented in the form of a liposome, ISCOM or an oil in water emulsion.

An enhanced system involves the combination of a monophosphoryl lipid A (or detoxified lipid A) and a saponin derivative, particularly the combination of QS21 and 3D-MPL as disclosed in WO 94/00153, or a less reactogenic composition where the QS21 is quenched with cholesterol as disclosed in WO 96/33739. A particularly potent adjuvant formulation involving tocopherol with or without QS21 and/or 3D-MPL in an oil in water emulsion is described in WO 95/17210. In one embodiment the immunogenic composition additionally comprises a saponin, which may be QS21.

Immunostimulatory oligonucleotides or any other Toll-like receptor (TLR) 9 agonist may also be used. The preferred oligonucleotides for use in adjuvants or vaccines of the present invention are CpG containing oligonucleotides, preferably containing two or more dinucleotide CpG motifs separated by at least three, more preferably at least six or more nucleotides. A CpG motif is a Cytosine nucleotide followed by a Guanine nucleotide. The CpG oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. No. 5,666,153, U.S. Pat. No. 5,278,302 and WO95/26204.

Examples of preferred oligonucleotides have the following sequences. The sequences preferably contain phosphorothioate modified internucleotide linkages.

```
OLIGO 1 (SEQ ID NO: 1):
TCC ATG ACG TTC CTG ACG TT (CpG 1826)

OLIGO 2 (SEQ ID NO: 2):
TCT CCC AGC GTG CGC CAT (CpG 1758)

OLIGO 3 (SEQ ID NO: 3):
ACC GAT GAC GTC GCC GGT GAC GGC ACC ACG

OLIGO 4 (SEQ ID NO: 4):
TCG TCG TTT TGT CGT TTT GTC GTT (CpG 2006)

OLIGO 5 (SEQ ID NO: 5):
TCC ATG ACG TTC CTG ATG CT (CpG 1668)

OLIGO 6 (SEQ ID NO: 6):
TCG ACG TTT TCG GCG CGC GCC G (CpG 5456)
```

Alternative CpG oligonucleotides may comprise the preferred sequences above in that they have inconsequential deletions or additions thereto.

The CpG oligonucleotides utilised in the present invention may be synthesized by any method known in the art (for example see EP 468520). Conveniently, such oligonucleotides may be synthesized utilising an automated synthesizer.

The adjuvant may be an oil in water emulsion or may comprise an oil in water emulsion in combination with other adjuvants. The oil phase of the emulsion system preferably comprises a metabolisable oil. The meaning of the term metabolisable oil is well known in the art. Metabolisable can be defined as "being capable of being transformed by metabolism" (Dorland's Illustrated Medical Dictionary, W.B. Sanders Company, 25$^{th}$ edition (1974)). The oil may be any vegetable oil, fish, oil, animal or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10$^{th}$ Edition, entry no. 8619).

Tocols (e.g. vitamin E) are also often used in oil emulsions adjuvants (EP 0 382 271 B1; U.S. Pat. No. 5,667,784; WO 95/17210). Tocols used in the oil emulsions (preferably oil in water emulsions) of the invention may be formulated as described in EP 0 382 271 B1, in that the tocols may be dispersions of tocol droplets, optionally comprising an emulsifier, of preferably less than 1 micron in diameter. Alternatively, the tocols may be used in combination with another oil, to form the oil phase of an oil emulsion. Examples of oil emulsions which may be used in combination with the tocol are described herein, such as the metabolisable oils described above.

Oil in water emulsion adjuvants per se have been suggested to be useful as adjuvant compositions (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B). All of which form preferred oil emulsion systems (in particular when incorporating tocols) to form adjuvants and compositions of the present invention.

Most preferably the oil emulsion (for instance oil in water emulsions) further comprises an emulsifier such as TWEEN® 80 and/or a sterol such as cholesterol.

A preferred oil emulsion (preferably oil-in-water emulsion) comprises a metabolisable, non-toxic oil, such as squalane, squalene or a tocopherol such as alpha tocopherol (and preferably both squalene and alpha tocopherol) and optionally an emulsifier (or surfactant) such as TWEEN® 80. A sterol (preferably cholesterol) may also be included.

The method of producing oil in water emulsions is well known to the man skilled in the art. Commonly, the method comprises mixing the tocol-containing oil phase with a surfactant such as a PBS/TWEEN® 80 solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil in water emulsion, the oil and emulsifier should be in an aqueous carrier. The aqueous carrier may be, for example, phosphate buffered saline.

The size of the oil droplets found within the stable oil in water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges. The amounts of the components present in the oil emulsions of the present invention are conventionally in the range of from 0.5-20% or 2 to 10% oil (of the total dose volume), such as squalene; and when present, from 2 to 10% alpha tocopherol; and from 0.3 to 3% surfactant, such as polyoxyethylene sorbitan monooleate. Preferably the ratio of oil (preferably squalene): tocol (preferably α-tocopherol) is equal or less than 1 as this provides a more stable emulsion. An emulsifier, such as TWEEN® 80 or SPAN® 85 may also be present at a level of about 1%. In some cases it may be advantageous that the vaccines of the present invention will further contain a stabiliser.

Examples of preferred emulsion systems are described in WO 95/17210, WO 99/11241 and WO 99/12565 which disclose emulsion adjuvants based on squalene, α-tocopherol, and TWEEN® 80, optionally formulated with the immunostimulants QS21 and/or 3D-MPL. Thus in a particularly, preferred embodiment of the present invention, the adjuvant of the invention may additionally comprise further immunostimulants, such as LPS or derivatives thereof, and/or saponins. Examples of further immunostimulants are described herein and in "Vaccine Design—The Subunit and Adjuvant Approach" 1995, Pharmaceutical Biotechnology, Volume 6, Eds. Powell, M. F., and Newman, M. J., Plenum Press, New York and London, ISBN 0-306-44867-X.

In a preferred aspect the adjuvant and immunogenic compositions according to the invention comprise a saponin (preferably QS21) and/or an LPS derivative (preferably 3D-MPL) in an oil emulsion described above, optionally with a sterol (preferably cholesterol). Additionally the oil emulsion (preferably oil in water emulsion) may contain SPAN® 85 and/or lecithin and/or tricaprylin. Adjuvants comprising an oil-in-water emulsion, a sterol and a saponin are described in WO 99/12565.

Typically for human administration the saponin (preferably QS21) and/or LPS derivative (preferably 3D-MPL) will be present in a human dose of immunogenic composition in the range of 1 µg-200 µg, such as 10-100 µg, preferably 10 µg-54 µg per dose. Typically the oil emulsion (preferably oil in water emulsion) will comprise from 2 to 10% metabolisible oil. Preferably it will comprise from 2 to 10% squalene, from 2 to 10% alpha tocopherol and from 0.3 to 3% (preferably 0.4-2%) emulsifier (preferably TWEEN® 80 [polyoxyethylene sorbitan monooleate]). Where both squalene and alpha tocopherol are present, preferably the ratio of squalene: alpha tocopherol is equal to or less than 1 as this provides a more stable emulsion. SPAN® 85 (Sorbitan trioleate) may also be present at a level of 0.5 to 1% in the emulsions used in the invention. In some cases it may be advantageous that the immunogenic compositions and vaccines of the present invention will further contain a stabiliser, for example other emulsifiers/surfactants, including caprylic acid (merck index $10^{th}$ Edition, entry no. 1739), of which Tricaprylin is particularly preferred.

Where squalene and a saponin (preferably QS21) are included, it is of benefit to also include a sterol (preferably cholesterol) to the formulation as this allows a reduction in the total level of oil in the emulsion. This leads to a reduced cost of manufacture, improvement of the overall comfort of the vaccination, and also qualitative and quantitative improvements of the resultant immune responses, such as improved IFN-γ production. Accordingly, the adjuvant system of the present invention typically comprises a ratio of metabolisable oil:saponin (w/w) in the range of 200:1 to 300:1, also the present invention can be used in a "low oil" form the preferred range of which is 1:1 to 200:1, preferably 20:1 to 100:1, and most preferably substantially 48:1, this vaccine retains the beneficial adjuvant properties of all of the components, with a much reduced reactogenicity profile. Accordingly, the particularly preferred embodiments have a ratio of squalene:QS21 (w/w) in the range of 1:1 to 250:1, also a preferred range is 20:1 to 200:1, preferably 20:1 to 100:1, and most preferably substantially 48:1. Preferably a sterol (most preferably cholesterol) is also included present at a ratio of saponin:sterol as described herein.

The emulsion systems of the present invention preferably have a small oil droplet size in the sub-micron range. Most preferably the oil droplet sizes will be in the range 120 to 750 nm, and most preferably from 120-600 nm in diameter.

A particularly potent adjuvant formulation (for ultimate combination with AlPO4 in the immunogenic compositions of the invention) involves a saponin (preferably QS21), an LPS derivative (preferably 3D-MPL) and an oil emulsion (preferably squalene and alpha tocopherol in an oil in water emulsion) as described in WO 95/17210 or in WO 99/12565 (in particular adjuvant formulation 11 in Example 2, Table 1).

Examples of a TLR 2 agonist include peptidoglycan or lipoprotein. Imidazoquinolines, such as Imiquimod and Resiquimod are known TLR7 agonists. Single stranded RNA is also a known TLR agonist (TLR8 in humans and TLR7 in mice), whereas double stranded RNA and poly IC (polyinosinic-polycytidylic acid—a commercial synthetic mimetic of viral RNA). are exemplary of TLR 3 agonists. 3D-MPL is an example of a TLR4 agonist whilst CPG is an example of a TLR9 agonist.

The immunogenic composition may comprise an antigen and an immunostimulant adsorbed onto a metal salt. Aluminium based vaccine formulations wherein the antigen and the immunostimulant 3-de-O-acylated monophosphoryl lipid A (3D-MPL), are adsorbed onto the same particle are described in EP 0 576 478 B1, EP 0 689 454 B1, and EP 0 633 784 B1. In these cases then antigen is first adsorbed onto the aluminium salt followed by the adsorption of the immunostimulant 3D-MPL onto the same aluminium salt particles. Such processes first involve the suspension of 3D-MPL by sonication in a water bath until the particles reach a size of between 80 and 500 nm. The antigen is typically adsorbed onto aluminium salt for one hour at room temperature under agitation. The 3D-MPL suspension is then added to the adsorbed antigen and the formulation is incubated at room temperature for 1 hour, and then kept at 4oC until use.

In another process, the immunostimulant and the antigen are on separate metal particles, as described in EP 1126876. The improved process comprises the adsorption of immunostimulant, onto a metallic salt particle, followed by the adsorption of the antigen onto another metallic salt particle, followed by the mixing of the discrete metallic particles to form a vaccine. The adjuvant for use in the present invention may be an adjuvant composition comprising an immunostimulant, adsorbed onto a metallic salt particle, characterised in that the metallic salt particle is substantially free of other antigen.

Furthermore, vaccines are provided by the present invention and are characterised in that the immunostimulant is adsorbed onto particles of metallic salt which are substantially free from other antigen, and in that the particles of metallic salt which are adsorbed to the antigen are substantially free of other immunostimulant.

Accordingly, the present invention provides an adjuvant formulation comprising immunostimulant which has been adsorbed onto a particle of a metallic salt, characterised in the composition is substantially free of other antigen. Moreover, this adjuvant formulation can be an intermediate which, if such an adjuvant is used, is required for the manufacture of a vaccine. Accordingly there is provided a process for the manufacture of a vaccine comprising admixing an adjuvant composition which is one or more immunostimulants adsorbed onto a metal particle with an antigen.

Preferably, the antigen has been pre-adsorbed onto a metallic salt. Said metallic salt may be identical or similar to the metallic salt which is adsorbed onto the immunostimulant. Preferably the metal salt is an aluminium salt, for example Aluminium phosphate or Aluminium hydroxide.

The present invention further provides for a vaccine composition comprising immunostimulant adsorbed onto a first particle of a metallic salt, and antigen adsorbed onto a metallic salt, characterised in that first and second particles of metallic salt are separate particles.

LPS or LOS derivatives or mutations or lipid A derivatives described herein are designed to be less toxic (e.g. 3D-MPL) than native lipopolysaccharides and are interchangeable equivalents with respect to any uses of these moieties described herein. They may be TLR4 ligands as described above. Other such derivatives are described in WO020786737, WO9850399, WO0134617, WO0212258, WO03065806.

In one embodiment the adjuvant used for the compositions of the invention comprises a liposome carrier (made by known techniques from a phospholipids (such as dioleoyl phosphatidyl choline [DOPC]) and optionally a sterol [such as cholesterol]). Such liposome carriers may carry lipid A derivatives [such as 3D-MPL—see above] and/or saponins (such as QS21—see above). In one embodiment the adjuvant comprises (per 0.5 mL dose) 0.1-10 mg, 0.2-7, 0.3-5, 0.4-2, or 0.5-1 mg (e.g. 0.4-0.6, 0.9-1.1, 0.5 or 1 mg) phospholipid (for instance DOPC), 0.025-2.5, 0.05-1.5, 0.075-0.75, 0.1-0.3, or 0.125-0.25 mg (e.g. 0.2-0.3, 0.1-0.15, 0.25 or 0.125 mg) sterol (for instance cholesterol), 5-60, 10-50, or 20-30 µg (e.g. 5-15, 40-50, 10, 20, 30, 40 or 50 µg) lipid A derivative (for instance 3D-MPL), and 5-60, 10-50, or 20-30 µg (e.g. 5-15, 40-50, 10, 20, 30, 40 or 50 µg) saponin (for instance QS21).

This adjuvant is particularly suitable for elderly vaccine formulations. In one embodiment the vaccine composition comprising this adjuvant comprises saccharide conjugates derived from at least all the following serotypes: 4, 6B, 9V, 14, 18C, 19F, 23F, 1, 5, 7F (and may also comprise one or more from serotypes 3, 6A, 19A, and 22F), wherein the GMC antibody titre induced against one or more (or all) the vaccine components 4, 6B, 9V, 14, 18C, 19F and 23F is not significantly inferior to that induced by the PREVNAR® vaccine in human vaccinees.

In one embodiment the adjuvant used for the compositions of the invention comprises an oil in water emulsion made from a metabolisable oil (such as squalene), an emulsifier (such as TWEEN® 80) and optionally a tocol (such as alpha tocopherol). In one embodiment the adjuvant comprises (per 0.5 mL dose) 0.5-15, 1-13, 2-11, 4-8, or 5-6 mg (e.g. 2-3, 5-6, or 10-11 mg) metabolisable oil (such as squalene), 0.1-10, 0.3-8, 0.6-6, 0.9-5, 1-4, or 2-3 mg (e.g. 0.9-1.1, 2-3 or 4-5 mg) emulsifier (such as TWEEN® 80) and optionally 0.5-20, 1-15, 2-12, 4-10, 5-7 mg (e.g. 11-13, 5-6, or 2-3 mg) tocol (such as alpha tocopherol).

This adjuvant may optionally further comprise 5-60, 10-50, or 20-30 µg (e.g. 5-15, 40-50, 10, 20, 30, 40 or 50 µg) lipid A derivative (for instance 3D-MPL).

These adjuvants are particularly suitable for infant or elderly vaccine formulations. In one embodiment the vaccine composition comprising this adjuvant comprises saccharide conjugates derived from at least all the following serotypes: 4, 6B, 9V, 14, 18C, 19F, 23F, 1, 5, 7F (and may also comprise one or more from serotypes 3, 6A, 19A, and 22F), wherein the GMC antibody titre induced against one or more (or all) the vaccine components 4, 6B, 9V, 14, 18C, 19F and 23F is not significantly inferior to that induced by the PREVNAR® vaccine in human vaccinees.

This adjuvant may optionally contain 0.025-2.5, 0.05-1.5, 0.075-0.75, 0.1-0.3, or 0.125-0.25 mg (e.g. 0.2-0.3, 0.1-0.15, 0.25 or 0.125 mg) sterol (for instance cholesterol), 5-60, 10-50, or 20-30 µg (e.g. 5-15, 40-50, 10, 20, 30, 40 or 50 µg) lipid A derivative (for instance 3D-MPL), and 5-60, 10-50, or 20-30 µg (e.g. 5-15, 40-50, 10, 20, 30, 40 or 50 µg) saponin (for instance QS21).

This adjuvant is particularly suitable for elderly vaccine formulations. In one embodiment the vaccine composition comprising this adjuvant comprises saccharide conjugates derived from at least all the following serotypes: 4, 6B, 9V, 14, 18C, 19F, 23F, 1, 5, 7F (and may also comprise one or more from serotypes 3, 6A, 19A, and 22F), wherein the GMC antibody titre induced against one or more (or all) the vaccine components 4, 6B, 9V, 14, 18C, 19F and 23F is not significantly inferior to that induced by the PREVNAR® vaccine in human vaccinees.

In one embodiment the adjuvant used for the compositions of the invention comprises aluminium phosphate and a lipid A derivative (such as 3D-MPL). This adjuvant may comprise (per 0.5 mL dose) 100-750, 200-500, or 300-400 µg Al as aluminium phosphate, and 5-60, 10-50, or 20-30 µg (e.g. 5-15, 40-50, 10, 20, 30, 40 or 50 µg) lipid A derivative (for instance 3D-MPL).

This adjuvant is particularly suitable for elderly or infant vaccine formulations. In one embodiment the vaccine composition comprising this adjuvant comprises saccharide conjugates derived from at least all the following serotypes: 4, 6B, 9V, 14, 18C, 19F, 23F, 1, 5, 7F (and may also comprise one or more from serotypes 3, 6A, 19A, and 22F), wherein the GMC antibody titre induced against one or more (or all) the vaccine components 4, 6B, 9V, 14, 18C, 19F and 23F is not significantly inferior to that induced by the PREVNAR® vaccine in human vaccinees.

The vaccine preparations containing immunogenic compositions of the present invention may be used to protect or treat a mammal susceptible to infection, by means of administering said vaccine via systemic or mucosal route. These administrations may include injection via the intramuscular (IM), intraperitoneal (IP), intradermal (ID) or subcutaneous (SC) routes; or via mucosal administration to the oral/alimentary, respiratory, genitourinary tracts. Intranasal (IN) administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). For co-administration, the optional Th1 adjuvant may be present in any or all of the different administrations. In addition to a single route of administration, 2 different routes of administration may be used. For example, saccharides or saccharide conjugates may be administered IM (or ID) and bacterial proteins may be administered IN (or ID). In addition, the vaccines of the invention may be administered IM for priming doses and IN for booster doses.

The content of protein antigens in the vaccine will typically be in the range 1-100 µg, preferably 5-50 µg, e.g. in the range 5-25 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

The vaccines of the present invention may be stored in solution or lyophilized. Preferably the solution is lyophilized in the presence of a sugar such as sucrose or lactose. It is still further preferable that they are lyophilized and extemporaneously reconstituted prior to use. Lyophilizing may result in a more stable composition (vaccine) and may possibly lead to higher antibody titers in the presence of 3D-MPL and in the absence of an aluminum based adjuvant.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms a preferred feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of antigens in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are preferably present in as little as 0.1 to 10 µg, preferably 0.1 to 5 µg per dose; and the saccharide (preferably conjugated) antigens may be present in the range of 0.01-1 µg, and preferably between 0.01 to 0.5 µg of saccharide per dose.

As used herein, the term "intradermal delivery" means delivery of the vaccine to the region of the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

The present invention further provides an improved vaccine for the prevention or amelioration of Otitis media caused by *Haemophilus influenzae* by the addition of *Haemophilus influenzae* proteins, for example protein D in conjugated form. In addition, the present invention further provides an improved vaccine for the prevention or amelioration of pneumococcal infection in infants (e.g., Otitis media), by relying on the addition of one or two pneumococcal proteins as free or conjugated protein to the *S. pneumoniae* conjugate compositions of the invention. Said pneumococcal free proteins may be the same or different to any *S. pneumoniae* proteins used as carrier proteins. One or more *Moraxella catarrhalis* protein antigens can also be included in the combination vaccine in a free or conjugated form. Thus, the present invention is an improved method to elicit a (protective) immune response against Otitis media in infants.

In another embodiment, the present invention is an improved method to elicit a (protective) immune response in infants (defined as 0-2 years old in the context of the present invention) by administering a safe and effective amount of the vaccine of the invention [a paediatric vaccine]. Further embodiments of the present invention include the provision of the antigenic *S. pneumoniae* conjugate compositions of the invention for use in medicine and the use of the *S. pneumoniae* conjugates of the invention in the manufacture of a medicament for the prevention (or treatment) of pneumococcal disease.

In another embodiment, the present invention is an improved method to elicit a (protective) immune response in the elderly population (in the context of the present invention a patient is considered elderly if they are 50 years or over in age, typically over 55 years and more generally over 60 years) by administering a safe and effective amount of the vaccine of the invention, preferably in conjunction with one or two *S. pneumoniae* proteins present as free or conjugated protein, which free *S. pneumoniae* proteins may be the same or different as any *S. pneumoniae* proteins used as carrier proteins.

A further aspect of the invention is a method of immunising a human host against disease caused by *S. pneumoniae* and optionally *Haemophilus influenzae* infection comprising administering to the host an immunoprotective dose of the immunogenic composition or vaccine or kit of the invention.

A further aspect of the invention is an immunogenic composition of the invention for use in the treatment or prevention of disease caused by *S. pneumoniae* and optionally *Haemophilus influenzae* infection.

A further aspect of the invention is use of the immunogenic composition or vaccine or kit of the invention in the manufacture of a medicament for the treatment or prevention of diseases caused by *S. pneumoniae* and optionally *Haemophilus influenzae* infection.

The terms "comprising", "comprise" and "comprises" herein are intended by the inventors to be optionally substitutable with the terms "consisting of", "consist of" and "consists of", respectively, in every instance.

Embodiments herein relating to "vaccine compositions" of the invention are also applicable to embodiments relating to "immunogenic compositions" of the invention, and vice versa.

All references or patent applications cited within this patent specification are incorporated by reference herein.

In order that this invention may be better understood, the following examples are set forth.

These examples are for purposes of illustration only, and are not to be construed as limiting the scope of the invention in any manner.

EXAMPLES

Example 1

Expression of Protein D

*Haemophilus influenzae* Protein D
Genetic construction for protein D expression
Starting Materials
The Protein D encoding DNA Protein D is highly conserved among *H. influenzae* of all serotypes and non-typeable strains. The vector pHIC348 containing the DNA sequence encoding the entire protein D gene has been obtained from Dr. A. Forsgren, Department of Medical Microbiology, University of Lund, Malmo General Hospital, Malmo, Sweden. The DNA sequence of protein D has been published by Janson et al. (1991) Infect. Immun. 59: 119-125.

The Expression Vector pMG1

The expression vector pMG1 is a derivative of pBR322 (Gross et al., 1985) in which bacteriophage λ derived control elements for transcription and translation of foreign inserted genes were introduced (Shatzman et al., 1983). In addition, the Ampicillin resistance gene was exchanged with the Kanamycin resistance gene.

The *E. coli* Strain AR58

The *E. coli* strain AR58 was generated by transduction of N99 with a P1 phage stock previously grown on an SA500 derivative (galE::TN10, lambdaKil⁻ cI857 ΔH1). N99 and SA500 are *E. coli* K12 strains derived from Dr. Martin Rosenberg's laboratory at the National Institute of Health.

The Expression Vector pMG 1

For the production of protein D, the DNA encoding the protein has been cloned into the expression vector pMG 1. This plasmid utilises signals from lambdaphage DNA to drive the transcription and translation of inserted foreign genes. The vector contains the promoter PL, operator OL and two utilisation sites (NutL and NutR) to relieve transcriptional polarity effects when N protein is provided (Gross et al., 1985). Vectors containing the PL promoter are introduced into an *E. coli* lysogenic host to stabilise the plasmid DNA. Lysogenic host strains contain replication-defective lambdaphage DNA integrated into the genome (Shatzman et al., 1983). The chromosomal lambdaphage DNA directs the synthesis of the cI repressor protein which binds to the OL repressor of the vector and prevents binding of RNA polymerase to the PL promoter and thereby transcription of the inserted gene. The cI gene of the expression strain AR58 contains a temperature sensitive mutant so that PL directed transcription can be regulated by temperature shift, i.e. an increase in culture temperature inactivates the repressor and synthesis of the foreign protein is initiated. This expression system allows controlled synthesis of foreign proteins especially of those that may be toxic to the cell (Shimataka & Rosenberg, 1981).

The *E. coli* Strain AR58

The AR58 lysogenic *E. coli* strain used for the production of the protein D carrier is a derivative of the standard NIH *E. coli* K12 strain N99 (F⁻ su⁻ galK2, lacZ⁻ thr⁻). It contains a defective lysogenic lambdaphage (galE::TN10, lambdaKil⁻ cI857 ΔH1). The Kil⁻ phenotype prevents the shut off of host macromolecular synthesis. The cI857 mutation confers a temperature sensitive lesion to the cI repressor. The ΔH1 deletion removes the lambdaphage right operon and the hosts bio, uvr3, and chlA loci. The AR58 strain was generated by transduction of N99 with a P1 phage stock previously grown on an SA500 derivative (galE::TN10, lambdaKil⁻ cI857 ΔH1). The introduction of the defective lysogen into N99 was selected with tetracycline by virtue of the presence of a TN10 transposon coding for tetracyclin resistance in the adjacent galE gene.

Construction of Vector pMGMDPPrD

The pMG 1 vector which contains the gene encoding the non-structural S1 protein of *Influenzae* virus (pMGNSI) was used to construct pMGMDPPrD. The protein D gene was amplified by PCR from the pHIC348 vector (Janson et al. 1991 Infect. Immun. 59:119-125) with PCR primers containing NcoI and XbaI restriction sites at the 5' and 3' ends, respectively. The NcoI/XbaI fragment was then introduced into pMGNS1 between NcoI and XbaI thus creating a fusion protein containing the N-terminal 81 amino acids of the NS1 protein followed by the PD protein. This vector was labelled pMGNS1PrD.

Based on the construct described above the final construct for protein D expression was generated. A BamHI/BamHI fragment was removed from pMGNS1PrD. This DNA hydrolysis removes the NS1 coding region, except for the first three N-terminal residues. Upon religation of the vector a gene encoding a fusion protein with the sequence shown in WO 07/71711, example 1, page 44 is generated.

The protein D does not contain a leader peptide or the N-terminal cysteine to which lipid chains are normally attached. The protein is therefore neither excreted into the periplasm nor lipidated and remains in the cytoplasm in a soluble form.

The final construct pMG-MDPPrD was introduced into the AR58 host strain by heat shock at 37° C. Plasmid containing bacteria were selected in the presence of Kanamycin. Presence of the protein D encoding DNA insert was demonstrated by digestion of isolated plasmid DNA with selected endonucleases. The recombinant *E. coli* strain is referred to as ECD4.

Expression of protein D is under the control of the lambda $P_L$ promoter/$O_L$ Operator. The host strain AR58 contains a temperature-sensitive cI gene in the genome which blocks expression from lambda $P_L$ at low temperature by binding to $O_L$. Once the temperature is elevated cI is released from $O_L$ and protein D is expressed.

Small-Scale Preparation

At the end of the fermentation the cells are concentrated and frozen.

The extraction from harvested cells and the purification of protein D was performed as follows. The frozen cell culture pellet is thawed and resuspended in a cell disruption solution (Citrate buffer pH 6.0) to a final $OD_{650}=60$. The suspension is passed twice through a high pressure homogenizer at P=1000 bar. The cell culture homogenate is clarified by centrifugation and cell debris is removed by filtration. In the first purification step the filtered lysate is applied to a cation exchange chromatography column (SP SEPHAROSE® Fast Flow). PD binds to the gel matrix by ionic interaction and is eluted by a step increase of the ionic strength of the elution buffer.

In a second purification step impurities are retained on an anionic exchange matrix (Q SEPHAROSE® Fast Flow). PD does not bind onto the gel and can be collected in the flow through.

In both column chromatography steps fraction collection is monitored by OD. The flow through of the anionic exchange column chromatography containing the purified protein D is concentrated by ultrafiltration.

The protein D containing ultrafiltration retentate is finally passed through a 0.2 µm membrane.

Large Scale Preparation

The extraction from harvested cells and the purification of protein D was performed as follows. The harvested broth is cooled and directly passed twice through a high pressure homogenizer at a Pressure of around 800 bars.

In the first purification step the cell culture homogenate is diluted and applied to a cation exchange chromatography column (SP SEPHAROSE® Big beads). PD binds to the gel matrix by ionic interaction and is eluted by a step increase of the ionic strength of the elution buffer and filtrated.

In a second purification step impurities are retained on an anionic exchange matrix (Q SEPHAROSE® Fast Flow). PD does not bind onto the gel and can be collected in the flow through.

In both column chromatography steps fraction collection is monitored by OD. The flow through of the anionic exchange column chromatography containing the purified protein D is concentrated and diafiltrated by ultrafiltration.

The protein D containing ultrafiltration retentate is finally passed through a 0.2 µm membrane.

Example 1 b

Expression OF PhtD

The PhtD protein is a member of the pneumococcal histidine-triad (Pht) protein family characterized by the presence of histidine-triads (HXXHXH motif—SEQ ID NO: 7). PhtD is a 838 aa-molecule and carries 5 histidine triads (see MedImmune WO00/37105 SEQ ID NO: 4 for amino acid sequence and SEQ ID NO: 5 for DNA sequence). PhtD also contains a proline-rich region in the middle (amino acid position 348-380). PhtD has a 20 aa-N-terminal signal sequence with a LXXC motif (SEQ ID NO: 8).

Genetic Construct

The gene sequence of the mature MedImmune PhtD protein (from aa 21 to aa 838) was transferred recombinantly to *E. coli* using the in-house pTCMP14 vector carrying the pλ promoter. The *E. coli* host strain is AR58, which carries the cI857 thermosensitive repressor, allowing heat-induction of the promotor.

Polymerase chain reaction was realized to amplify the phtD gene from a MedImmune plasmid (carrying the phtD gene from *Streptococcus pneumoniae* strain Norway 4 (serotype 4)—SEQ ID NO: 5 as described in WO 00/37105). Primers, specific for the phtD gene only, were used to amplify the phtD gene in two fragments. Primers carry either the NdeI and KpnI or the KpnI and XbaI restriction sites. These primers do not hybridize with any nucleotide from the vector but only with phtD specific gene sequences. An artificial ATG start codon was inserted using the first primer carrying the NdeI restriction site. The generated PCR products were then inserted into the pGEM-T cloning vector (Promega), and the DNA sequence was confirmed. Subcloning of the fragments in the TCMP14 expression vector was then realized using standard techniques and the vector was transformed into AR58 *E. coli*.

PhtD Purification

PhtD purification is achieved as follows:
 Growth of *E. coli* cells in the presence of Kanamycin: growth 30 hours at 30° C. then induction for 18 hours at 39.5° C.
 Breakage of the *E. coli* cells from whole culture at OD ±115 in presence of EDTA 5 mM and PMSF 2 mM as protease inhibitors: Rannie, 2 passages, 1000 bars.
 Antigen capture and cells debris removal on expanded bed mode Streamline Q XL chromatography at room temperature (20° C.); the column is washed with NaCl 150 mM+EMPIGEN® 0.25% pH 6.5 and eluted with NaCl 400 mM+EMPIGEN® 0.25% in 25 mM potassium phosphate buffer pH 7.4.
 Filtration on Sartobran 150 cartridge (0.45+0.2 µm)
 Antigen binding on $Zn^{++}$ Chelating SEPHAROSE® FF IMAC chromatography at pH 7.4 in presence of 5 mM imidazole at 4° C.; the column is washed with Imidazole 5 mM and EMPIGEN® 1% and eluted with 50 mM imidazole, both in 25 mM potassium phosphate buffer pH 8.0.
 Weak anion exchange chromatography in positive mode on FRACTOGEL® EMD DEAE at pH 8.0 (25 mM potassium phosphate) at 4° C.; the column is washed with 140 mM NaCl and eluted at 200 mM NaCl while contaminants (proteins and DNA) remain adsorbed on the exchanger.
 Concentration and ultrafiltration with 2 mM Na/K phosphate pH 7.15 on 50 kDa membrane.
 Sterilising filtration of the purified bulk on a MILLI-PAK®-20 0.2 µm filter cartridge.

Example 1c

Expression of Pneumolysin

Pneumococcal pneumolysin was prepared and detoxified as described in WO2004/081515 and WO2006/032499.

Example 2

Preparation of Conjugates

It is well known in the art how to make purified pneumococcal polysaccharides. For the purposes of these examples the polysaccharides were made essentially as described in EP072513 or by closely-related methods. Before conjugation the polysaccharides may be sized by microfluidisation as described below.

The activation and coupling conditions are specific for each polysaccharide. These are given in Table 1. Sized polysaccharide (except for PS5, 6B and 23F) was dissolved in NaCl 2M, NaCl 0.2M or in water for injection (WFI). The optimal polysaccharide concentration was evaluated for all the serotypes. All serotypes except serotype 18C were conjugated directly to the carrier protein as detailed below. Two alternative serotype 22F conjugates were made; one conjugated directly, one through an ADH linker.

From a 100 mg/ml stock solution in acetonitrile or acetonitrile/water 50%/50% solution, CDAP (CDAP/PS ratio 0.5-1.5 mg/mg PS) was added to the polysaccharide solution. 1.5 minute later, 0.2M-0.3M NaOH was added to obtain the specific activation pH. The activation of the polysaccharide was performed at this pH during 3 minutes at 25° C. Purified protein (protein D, PhtD, pneumolysin or DT) (the quantity depends on the initial PS/carrier protein ratio) was added to the activated polysaccharide and the coupling reaction was performed at the specific pH for up to 2 hour (depending upon serotype) under pH regulation. In order to quench un-reacted cyanate ester groups, a 2M glycine solution was then added to the mixture. The pH was adjusted to the quenching pH (pH 9.0). The solution was stirred for 30 minutes at 25° C. and then overnight at 2-8° C. with continuous slow stirring.

Preparation of 18C:

18C was linked to the carrier protein via a linker—Adipic acid dihydrazide (ADH) Polysaccharide serotype 18C was microfluidized before conjugation.

Derivatization of Tetanus Toxoid with EDAC

For derivatization of the tetanus toxoid, purified TT was diluted at 25 mg/ml in 0.2M NaCl and the ADH spacer was added in order to reach a final concentration of 0.2M. When the dissolution of the spacer was complete, the pH was adjusted to 6.2. EDAC (1-ethyl-3-(3-dimethyl-aminopropyl) carbodiimide) was then added to reach a final concentration of 0.02M and the mixture was stirred for 1 hour under pH regulation. The reaction of condensation was stopped by increasing pH up to 9.0 for at least 30 minutes at 25° C. Derivatized TT was then diafiltrated (10 kDa CO membrane) in order to remove residual ADH and EDAC reagent.

$TT_{AH}$ bulk was finally sterile filtered until coupling step and stored at −70° C.

Chemical Coupling of $TT_{AH}$ to PS 18C

Details of the conjugation parameters can be found in Table 1.

2 grams of microfluidized PS were diluted at the defined concentration in water and adjusted to 2M NaCl by NaCl powder addition.

CDAP solution (100 mg/ml freshly prepared in 50/50 v/v acetonitrile/WFI) was added to reach the appropriate CDAP/PS ratio.

The pH was raised up to the activation pH 9.0 by the addition of 0.3M NaOH and was stabilised at this pH until addition of $TT_{AH}$.

After 3 minutes, derivatized $TT_{AH}$ (20 mg/ml in 0.2 M NaCl) was added to reach a ratio $TT_{AH}$/PS of 2; the pH was regulated to the coupling pH 9.0. The solution was left one hour under pH regulation.

For quenching, a 2M glycine solution was added to the mixture PS/$TT_{AH}$/CDAP.

The pH was adjusted to the quenching pH (pH 9.0).

The solution was stirred for 30 min at 25° C., and then left overnight at 2-8° C. with continuous slow stirring.

PS22FF$_{AH}$-PhtD Conjugate

In a second conjugation method for this saccharide (the first being the direct PS22-PhtD conjugation method shown in Table 1), 22F was linked to the carrier protein via a linker—Adipic acid dihydrazide (ADH). Polysaccharide serotype 22F was microfluidized before conjugation.

PS 22F Derivatization

Activation and coupling are performed at 25° C. under continuous stirring in a temperature-controlled waterbath.

Microfluidized PS22F was diluted to obtain a final PS concentration of 6 mg/ml in 0.2M NaCl and the solution was adjusted at pH 6.05±0.2 with 0.1N HCl.

CDAP solution (100 mg/ml freshly prepared in acetonitrile/WFI, 50/50) was added to reach the appropriate CDAP/PS ratio (1.5/1 ww).

The pH was raised up to the activation pH 9.00±0.05 by the addition of 0.5M NaOH and was stabilised at this pH until addition of ADH.

After 3 minutes, ADH was added to reach the appropriate ADH/PS ratio (8.9/1 w/w); the pH was regulated to coupling pH 9.0. The solution was left for 1 hour under pH regulation.

The PS$_{AH}$ derivative was concentrated and diafiltrated.

Coupling

PhtD at 10 mg/ml in 0.2M NaCl was added to the PS22F$_{AH}$ derivative in order to reach a PhtD/PS22F$_{AH}$ ratio of 4/1 (w/w). The pH was adjusted to 5.0±0.05 with HCl. The EDAC solution (20 mg/ml in 0.1M Tris-HCl pH 7.5) was added manually in 10 min (250 µl/min) to reach 1 mg EDAC/mg PS22F$_{AH}$. The resulting solution was incubated for 150 min (though 60 mins was also used) at 25° C. under stirring and pH regulation. The solution was neutralized by addition of 1M Tris-HCl pH 7.5 (1/10 of the final volume) and let 30 min at 25° C.

Prior to the elution on SEPHACRYL® S400HR, the conjugate was clarified using a 5 µm Minisart filter.

The resulting conjugate has a final PhtD/PS ratio of 4.1 (w/w), a free PS content below 1% and an antigenicity (α-PS/α-PS) of 36.3% and anti-PhtD antigenicity of 7.4%. The ratio of protein and polysaccharide was measured using Lowry and Resorcinol methods and the antigenicity was determined using sandwich ELISA.

Purification of the Conjugates:

The conjugates were purified by gel filtration using a SEPHACRYL® S400HR gel filtration column equilibrated with 0.15M NaCl (S500HR for 18C) to remove small molecules (including DMAP) and unconjugated PS and protein. Based on the different molecular sizes of the reaction components, PS-PD, PS-TT, PS-PhtD, PS-pneumolysin or PS-DT conjugates are eluted first, followed by free PS, then by free PD or free DT and finally DMAP and other salts (NaCl, glycine).

Fractions containing conjugates are detected by $UV_{280\ nm}$. Fractions are pooled according to their Kd, sterile filtered (0.2 µm) and stored at +2-8° C. The PS/Protein ratios in the conjugate preparations were determined.

Specific Activation/Coupling/Quenching Conditions
of PS *S. pneumoniae*-Protein
D/TT/DT/PhtD/Plyconjugates Where "µfluid" appears in a row header, it indicates that the saccharide was sized by microfluidisation before conjugation. Sizes of saccharides following microfluidisation are given in table 2.

TABLE 1

Specific activation/coupling/quenching conditions of PS S. pneumoniae-
Protein D/TT/DT/PhtD/Plyconjugates

| Serotype | 1 μfluid | 4 μfluid | 5 | 6A | 6B | 7F μfluid |
|---|---|---|---|---|---|---|
| PS conc.(mg/ml) | 2.5 | 2.5 | 7.1 | 5.0 | 5.0 | 5.0 |
| PS dissolution | WFI | WFI | WFI | NaCl 2M | NaCl 2M | NaCl 2M |
| PD conc.(mg/ml) | 10.0 | 10.0 | 5.0 | 5.0 | 5.0 | 10.0 |
| Initial PD/PS Ratio (w/w) | 1.5/1 | 1.5/1 | 1/1 | 1/1 | 1.1/1 | 1.2/1 |
| CDAP conc. (mg/mg PS) | 0.50 | 0.50 | 0.79 | 0.83 | 0.83 | 0.75 |
| $pH_a = pH_c = pH_q$ | 9.0/9.0/9.0 | 9.5/9.5/9.0 | 9.0/9.0/9.0 | 9.5/9.5/9.0 | 9.5/9.5/9.0 | 9.5/9.5/9.0 |

| Serotype | 9V μfluid | 14 μfluid | 18C μfluid | 19A μfluid | 19F μfluid | 22F μfluid | 23F |
|---|---|---|---|---|---|---|---|
| PS conc.(mg/ml) | 5.0 | 5.0 | 4.5 | 15.0 | 9.0 | 6.0 | 2.38 |
| PS dissolution | NaCl 2M | NaCl 2M | NaCl 2M | NaCl 2M | NaCl 2M | NaCl 0.2M | NaCl 2M |
| Carrier protein conc.(mg/ml) | 10.0 | 10.0 | 20.0 (TT) | 10.0 (Ply) | 20.0 (DT) | 10.0 (PhtD) | 5.0 |
| Initial carrier protein/PS Ratio (w/w) | 1.2/1 | 1.2/1 | 2/1 | 2.5/1 | 1.5/1 | 3/1 | 1/1 |
| CDAP conc. (mg/mg PS) | 0.50 | 0.75 | 0.75 | 1.5 | 1.5 | 1.5 | 0.79 |
| $pH_a = pH_c = pH_q$ | 9.5/9.5/9.0 | 9.5/9.5/9.0 | 9.0/9.0/9.0 | 9.0/9.0/9.0 | 9.0/9.0/9.0 | 9.0/9.0/9.0 | 9.5/9.5/9.0 |

Note:
pHa, c, q corresponds to the pH for activation, coupling and quenching, respectively Characterisation:

Each conjugate was characterised and met the specifications described in Table 2. The polysaccharide content (μg/ml) was measured by the Resorcinol test and the protein content (μg/ml) by the Lowry test. The final PS/PD ratio (w/w) is determined by the ratio of the concentrations.

Free Polysaccharide Content (%):

The free polysaccharide content of conjugates kept at 4° C. or stored 7 days at 37° C. was determined on the supernatant obtained after incubation with α-carrier protein antibodies and saturated ammonium sulfate, followed by a centrifugation.

An α-PS/α-PS ELISA was used for the quantification of free polysaccharide in the supernatant. The absence of conjugate was also controlled by an α-carrier protein/α-PS ELISA.

Antigenicity:

The antigenicity on the same conjugates was analyzed in a sandwich-type ELISA wherein the capture and the detection of antibodies were α-PS and α-Protein respectively.

Free Protein Content (%):

Unconjugated carrier protein can be separated from the conjugate during the purification step. The content of free residual protein was determined using size exclusion chromatography (TSK 5000-PWXL) followed by UV detection (214 nm). The elution conditions allowed separating the free carrier protein and the conjugate. Free protein content in conjugate bulks was then determined versus a calibration curve (from 0 to 50 μg/ml of carrier protein). Free carrier protein in % was obtained as follows: % free carrier=(free carrier (μg/ml)/(Total concentration of corresponding carrier protein measured by Lowry (μg/ml)*100%).

Stability:

Molecular weight distribution ($K_{av}$) and stability was measured on a HPLC-SEC gel filtration (TSK 5000-PWXL) for conjugates kept at 4° C. and stored for 7 days at 37° C.

The 10/11/13/14-valent characterization is given in Table 2 (see comment thereunder).

The protein conjugates can be adsorbed onto aluminium phosphate and pooled to form the final vaccine.

TABLE 2 characteristics of the conjugates

| Conjugates | PS size (Da × 10³) | Carrier/PS Ratio | Free PS (Elisa) | Free Carrier | PS Antigenicity (Elisa) | Conj. Size (kDa) |
|---|---|---|---|---|---|---|
| PS1-PD | 349-382* | 1.5-1.6 | 1.0%-1.2% | 3.9%-4.8% | 87%-95% | 1499-1715 |
| PS4-PD | 93-100* | 1.5-1.6 | 4.7-6.5% | 3.2%-4.0% | 90%-96% | 1303-1606 |
| PS5-PD*** | 367-443 | 0.80 | 8.7-11.2% | 2.2%-3.8% | 93%-108% | 1998-2352 |
| PS6A-PD | 1100-1540 | 0.61 | 4.5% | ND | 45.9% | ND |
| PS6B-PD*** | 1069-1391 | 0.7-0.8 | 1.3-1.6% | <2.0% | 68%-75% | 4778-5235 |

TABLE 2-continued characteristics of the conjugates

| Conjugates | PS size (Da × 10³) | Carrier/PS Ratio | Free PS (Elisa) | Free Carrier | PS Antigenicity (Elisa) | Conj. Size (kDa) |
|---|---|---|---|---|---|---|
| PS7F-PD | 255-264* | 1.1-1.2 | <1% | <1.4% | 58% | 3907-4452 |
| PS9V-PD | 258-280* | 1.3-1.5 | <1% | <1.3% | 67%-69% | 9073-9572 |
| PS14-PD | 232-241* | 1.4 | <1% | <1.5% | 70% | 3430-3779 |
| PS18C-TT | 89-97* | 2.2-2.4 | 1.5-2.2% | <4% | 46%-56% | 5464-6133 |
| PS19A-Ply* | 151 | 3.2 | <1% |  | 29% |  |
| PS19F-DT | 133-143* | 1.4-1.5 | 4.1%-5.9% | <1.2%-<1.3% | 82%-88% | 2059-2335 |
| PS22F-PhtD* | 159-167 | 2.17 | 5.8 | ND | 37% | ND |
| PS22F-AHPhtD* | 159-167 | 3.66-4.34 | <1% | ND | 28-31% | ND |
| PS23F-PD*** | 914-980 | 0.5 | 1.4-1.9% | 3.7%-4.9% | 137%-154% | 2933-3152 |

*PS size following microfluidization of the native PS
***unsized polysaccharide
ND—not determined A 10 valent vaccine was made by mixing serotype 1, 4, 5, 6B, 7F, 9V, 14, 18C, 19F and 23F conjugates (e.g. at a dose of 1, 3, 1, 1, 1, 1, 1, 3, 3, 1 μg of saccharide, respectively per human dose). An 11 valent vaccine was made by further adding the serotype 3 conjugate from Table 5 (e.g. at 1 μg of saccharide per human dose). A 13 valent vaccine was made by further adding the serotypes 19A and 22F conjugates above (with 22F either directly linked to PhtD, or alternatively through an ADH linker) [e.g. at a dose of 3 μg each of saccharide per human dose]. A 14 valent vaccine may be made by further adding the serotype 6A conjugate above [e.g. at a dose of 1 μg of saccharide per human dose.

Example 3

Evidence that Inclusion of Haemphilus Influenzae Protein D in an Immunogenic Composition of the Invention can Provide Improved Protection Against Acute Otitis Media (AOM)

Study Design.

The study used an 11Pn-PD vaccine—comprising serotypes 1, 3, 4, 5, 6B, 7F, 9V, 14, 18C, 19F and 23F each conjugated to protein D from *H. influenzae* (refer to Table 5 in Example 4). Subjects were randomized into two groups to receive four doses of either the 11Pn-PD vaccine or HAVRIX® at approximately 3, 4, 5 and 12-15 months of age. All subjects received GSK Biologicals' INFANRIX®—HEXA (DTPa-HBV-IPV/Hib) vaccine concomitantly at 3, 4 and 5 months of age. INFANRIX®—HEXA is a combination of PEDIARIX® and Hib mixed before administration. Efficacy follow-up for the "According-to-Protocol" analysis started 2 weeks after administration of the third vaccine dose and continued until 24-27 months of age. Nasopharyngeal carriage of *S. pneumoniae* and *H. influenzae* was evaluated in a selected subset of subjects.

Parents were advised to consult the investigator if their child was sick, had ear pain, spontaneous perforation of the tympanic membrane or spontaneous ear discharge. If the investigator suspected an episode of AOM, the child was immediately referred to an Ear, Nose and Throat (ENT) specialist for confirmation of the diagnosis.

A clinical diagnosis of AOM was based on either the visual appearance of the tympanic membrane (i.e. redness, bulging, loss of light reflex) or the presence of middle ear fluid effusion (as demonstrated by simple or pneumatic otoscopy or by microscopy). In addition, at least two of the following signs or symptoms had to be present: ear pain, ear discharge, hearing loss, fever, lethargy, irritability, anorexia, vomiting, or diarrhea. If the ENT specialist confirmed the clinical diagnosis, a specimen of middle ear fluid was collected by tympanocentesis for bacteriological testing.

For subjects with repeated sick visits, a new AOM episode was considered to have started if more than 30 days had elapsed since the beginning of the previous episode. In addition, an AOM episode was considered to be a new bacterial episode if the isolated bacterium/serotype differed from the previous isolate whatever the interval between the two consecutive episodes.

Trial Results

A total of 4968 infants were enrolled, 2489 in the 11Pn-PD group and 2479 in the control group. There were no major differences in the demographic characteristics or risk factors between the two groups.

Clinical Episodes and AOM Case Definition

During the per protocol follow-up period, a total of 333 episodes of clinical AOM were recorded in the 11Pn-PD group and 499 in the control group.

Table 3 presents the protective efficacy of the 11Pn-PD vaccine and both 7-valent vaccines previously tested in Finland (Eskola et al N Engl J Med 2001; 344: 403-409 and Kilpi et al Clin Infect Dis 2003 37:1155-64) against any episode of AOM and AOM caused by different pneumococcal serotypes, *H. influenzae*, NTHi and *M. catarrhalis*. Statistically significant and clinically relevant reduction by 33.6% of the overall AOM disease burden was achieved with 11Pn-PD, irrespective of the etiology (table 3). The overall efficacy against AOM episodes due to any of the 11 pneumococcal serotypes contained in the 11Pn-PD vaccine was 57.6% (table 3).

Another important finding in the current study is the 35.6% protection provided by the 11Pn-PD vaccine against AOM caused by *H. influenzae* (and specifically 35.3% protection provided by NTHi). This finding is of major clinical significance, given the increased importance of *H. influenzae* as a major cause of AOM in the pneumococcal conjugate vaccine era. In line with the protection provided against AOM, the 11Pn-PD vaccine also reduced nasopharyngeal carriage of *H. influenzae* following the booster dose in the second year of life. These findings are in contrast with previous observations in Finland where, for both 7-valent pneumococcal conjugate vaccines, an increase in AOM episodes due to *H. influenzae* was observed, (Eskola et al and Kilpi et al) as evidence of etiological replacement.

A clear correlation between protection against AOM episodes due to Hi and antibody levels against the carrier Protein D could not be established, as post-primary anti-PD IgG antibody concentrations in 11Pn-PD vaccinees, that remained Hi AOM episode-free, were essentially the same as post-primary anti-PD IgG antibody levels measured in 11Pn-PD vaccinees that developed at least one Hi AOM episode during the efficacy follow-up period. However, although no correlation could be established between the biological impact of the vaccine and the post-primary IgG anti-PD immunogenicity, it is reasonable to assume that the PD carrier protein, which is highly conserved among *H. influenzae* strains, has contributed to a large extent in the induction of the protection against Hi.

The effect on AOM disease was accompanied by an effect on nasopharyngeal carriage that was of similar magnitude for vaccine serotype pneumococci and *H. influenzae* (FIG. 1). This reduction of the nasopharyngeal carriage of *H. influenzae* in the PD-conjugate vaccinees supports the hypothesis of a direct protective effect of the PD-conjugate vaccine against *H. influenzae*, even if the protective efficacy could not be correlated to the anti-PD IgG immune responses as measured by ELISA.

In a following experiment a chinchilla otitis media model was used with serum pools from infants immunised with the 11 valent formulation of this example or with the 10 valent vaccine of Example 2 (see also Table 1 and 2 and comments thereunder). Both pools induce a significant reduction of the percentage of animals with otitis media versus the pre-immune serum pool. There is no significant difference between the 10 and 11 valent immune pools. This demonstrates that both vaccines have a similar potential to induce protection against otitis media caused by non typeable *H. influenzae* in this model.

Example 4

Selection of Carrier Protein for Serotype 19F

ELISA Assay Used

The 22F inhibition ELISA method was essentially based on an assay proposed in 2001 by Concepcion and Frasch and was reported by Henckaerts et al., 2006, Clinical and Vaccine Immunology 13:356-360. Briefly, purified pneumococcal polysaccharides were mixed with methylated human serum albumin and adsorbed onto Nunc Maxisorp™ (Roskilde, DK) high binding microtitre plates overnight at 4° C. The plates were blocked with 10% fetal bovine serum (FBS) in PBS for 1 hour at room temperature with agitation. Serum samples were diluted in PBS containing 10% FBS, 10 µg/mL cell-wall polysaccharide (SSI) and 2 µg/mL of pneumococcal polysaccharide of serotype 22F (ATCC), and further diluted on the microtitre plates with the same buffer. An internal reference calibrated against the standard serum 89-SF using the serotype-specific IgG concentrations in 89-SF was treated in the same way and included on every plate. After washing, the bound antibodies were detected using peroxidase-conjugated anti-human IgG monoclonal antibody (Stratech Scientific Ltd., Soham, UK) diluted in 10% FBS (in PBS), and incubated for 1 hour at room temperature with agitation. The color was developed using ready-to-use single component tetramethylbenzidine peroxidase enzyme immunoassay substrate kit (BioRad, Hercules, Calif., US) in the dark at room temperature. The reaction was stopped with H2SO4 0.18 M, and the optical density was read at 450 nm. Serotype-specific IgG concentrations (in µg/mL) in the samples were calculated by referencing optical density points within defined limits to the internal reference serum curve, which was modelized by a 4-parameter logistic log equation calculated with SoftMax Pro™ (Molecular Devices, Sunnyvale, Calif.) software. The cut-off for the ELISA was 0.05 µg/mL IgG for all serotypes taking into account the limit of detection and the limit of quantification.

Opsonophagocytosis Assay

At the WHO consultation meeting in June 2003, it was recommended to use an OPA assay as set out in Romero-

TABLE 3

| | 11Pn-PD | | | | | Prevnar in FinOM[Eskola et al] | | | | | 7v-OMP in FinOM[Kilip et al] | | | | |
|---|---|---|---|---|---|---|---|---|---|---|---|---|---|---|---|
| | n | | VE | | | n | | VE | | | n | | VE | | |
| | | | | 95% CI | | | | | 95% CI | | | | | 95% CI | |
| Type of AOM episode | 11Pn-PD | Control | % | LL | UL | 7v-CRM | Control | % | LL | UL | 7v-OMP | Control | % | LL | UL |
| N | 2455 | 2452 | | | | 786 | 794 | | | | 805 | 794 | | | |
| Any AOM | 333 | 499 | 33.6 | 20.8 | 44.3 | 1251 | 1345 | 6 | −4 | 16 | 1364 | 1345 | −1 | −12 | 10 |
| Any AOM with MEF | 322 | 474 | 32.4 | 19.0 | 43.6 | 1177 | 1267 | 7 | −5 | 17 | 1279 | 1267 | 0 | −12 | 10 |
| Culture confirmed pneumococcus | 92 | 189 | 51.5 | 36.8 | 62.9 | 271 | 414 | 34 | 21 | 45 | 314 | 414 | 25 | 11 | 37 |
| Vaccine pneumococcal serotypes[*] | 60 | 141 | 57.6 | 41.4 | 69.3 | 107 | 250 | 57 | 44 | 67 | 110 | 250 | 56 | 44 | 66 |
| Other bacterial pathogens | | | | | | | | | | | | | | | |
| *H. influenzae* | 44 | 68 | 35.6 | 3.8 | 57.0 | 315 | 287 | −11 | −34 | 8 | 315 | 287 | −9 | −32 | 10 |
| Non-typeable *H. influenzae* (NTHi) | 41 | 63 | 35.3 | 1.8 | 57.4 | NP | NP | NP | NP | NP | NP | NP | NC | NP | NP |
| *M. catarrhalis* | 31 | 34 | 9.4 | −52.5 | 46.1 | 379 | 381 | −1 | −19 | 15 | 444 | 381 | −16 | −36 | 2 |

NP = Not published;
N = number of subjects in ATP efficacy cohort;
n = number of episodes
*Vaccine pneumococcal serotypes: for 11Pn-PD = 11 serotypes, for Prevnar and 7v-OMP = 7 serotypes
MEF = Middle ear fluid Steiner et al Clin Diagn Lab Immunol 2003 10 (6): pp1019-1024. This protocol was used to test the OPA activity of the serotypes in the following tests.

Preparation of Conjugates

In studies 11Pn-PD&Di-001 and 11Pn-PD&Di-007, three 11-valent vaccine formulations (Table 4) were included in which 3 μg of the 19F polysaccharide was conjugated to diphtheria toxoid (19F-DT) instead of 1 μg polysaccharide conjugated to protein D (19F-PD). Conjugation parameters for the studies 11Pn-PD, 11Pn-PD&Di-001 and 11Pn-PD&Di-007 are disclosed in Tables 5, 6 and 7 respectively.

Anti-Pneumococcal Antibody Responses and OPA Activity Against Serotype 19F One Month Following Primary Vaccination with these 19F-DT Formulations are Shown in Table 8 and 9 Respectively.

Table 10 shows 22F-ELISA antibody concentrations and percentages of subjects reaching the 0.2 μg/mL threshold before and after 23-valent plain polysaccharide booster vaccination.

The opsonophagocytic activity was shown to be clearly improved for antibodies induced with these 19F-DT formulations as demonstrated by higher seropositivity rates (opsonophagocytic titers≥1:8) and OPA GMTs one month following primary vaccination (Table 9). One month after 23-valent plain polysaccharide booster vaccination, opsonophagocytic activity of 19F antibodies remained significantly better for children primed with 19F-DT formulations (Table 11).

Table 12 presents immunogenicity data following a 11Pn-PD booster dose in toddlers previously primed with 19F-DT or 19F-PD conjugates compared to a $4^{th}$ consecutive dose of PREVNAR®. Given the breakthrough cases reported after the introduction of PREVNAR® in the US, the improved opsonophagocytic activity against serotype 19F when conjugated to the DT carrier protein may be an advantage for the candidate vaccine.

Table 13 provides ELISA and OPA data for the 19F-DT conjugate with respect to the cross-reactive serotype 19A. It was found that 19F-DT induces low but significant OPA activity against 19A.

TABLE 4

Pneumococcal conjugate vaccine formulations used in clinical studies.

| Formulation | Pneumococcal serotype μg/carrier protein | | | | | | | | | | | $Al^{3+}$ |
|---|---|---|---|---|---|---|---|---|---|---|---|---|
| | 1 | 3 | 4 | 5 | 6B | 7F | 9V | 14 | 18C | 19F | 23F | mg |
| 11Pn-PD | 1/PD | 1/PD | 1/PD | 1/PD | 1/PD | 1/PD | 1/PD | 1/PD | 1/PD | 1/PD | 1/PD | <0.8 |
| 19F-DT Form 1 | 3/PD | 3/PD | 3/PD | 3/PD | 10/DT | 3/PD | 3/PD | 3/PD | 3/PD | 3/DT | 5/DT | ≤0.35 |
| 19F-DT Form 2 | 3/PD | 2/PD | 2/PD | 3/PD | 5/DT | 3/PD | 2/PD | 2/PD | 2/PD | 3/DT | 5/DT | ≤0.35 |
| 19F-DT Form 3 | 3/PD | 3/PD | 3/PD | 3/PD | 3/PD | 3/PD | 3/PD | 3/PD | 3/PD | 3/DT | 3/PD | =0.5 |

TABLE 5

Specific activation/coupling/quenching conditions of PS S. pneumoniae-Protein D/TT/DTconjugates

| Serotype | 1 Native | 3 μfluid | 4 Native | 5 Native | 6B Native | 7F Native |
|---|---|---|---|---|---|---|
| PS conc.(mg/ml) | 1.5 | 2 | 2.0 | 7.5 | 5.5 | 3.0 |
| PS dissolution | NaCl 150 mM | NaCl 2M | WFI | WFI | NaCl 2M | NaCl 2M |
| PD conc.(mg/ml) | 5.0 | 5.0 | 5.0 | 5.0 | 5.0 | 5.0 |
| Initial PS/PD Ratio (w/w) | 1/0.7 | 1/1 | 1/1 | 1/1 | 1/1 | 1/1 |
| CDAP conc. (mg/mg PS) | 0.75 | 0.75 | 0.75 | 0.75 | 0.75 | 0.75 |
| $pH_a = pH_c = pH_g$ | 9.0/9.0/9.0 | 9.5/9.5/9.0 | 8.8/8.8/9.0 | 9.0/9.0/9.0 | 9.5/9.5/9.0 | 9.0/9.0/9.0 |
| Coupling time | 60 mins | 60 mins | 45 mins | 40 mins | 60 mins | 60 mins |

| Serotype | 9V Native | 14 Native | 18O Native | 19F Native | 23F Native |
|---|---|---|---|---|---|
| PS conc.(mg/ml) | 1.75 | 2.5 | 1.75 | 4.0 | 2.5 |
| PS dissolution | NaCl 2M | NaCl 2M | WFI | NaCl 2M | NaCl 2M |
| PD conc.(mg/ml) | 5.0 | 5.0 | 5.0 | 5.0 | 5.0 |
| Initial PS/PD Ratio (w/w) | 1/0.75 | 1/0.75 | 1/1.2 | 1/1 | 1/1 |
| CDAP conc. (mg/mg PS) | 0.75 | 0.75 | 0.75 | 0.75 | 0.75 |
| $pH_a = pH_c = pH_g$ | 8.5/8.5/9.0 | 9.0/9.0/9.0 | 9.0/9.0/9.0 | 9.5/9.5/9.0 | 9.5/9.5/9.0 |
| Coupling time | 60 mins | 60 mins | 45 mins | 30 mins | 60 mins |

TABLE 6

Specific activation/coupling/quenching conditions of PS
S. pneumoniae-Protein D/DTconjugates for the 11 Pn-PD&Di-001 study

| Serotype | 1 µfluid | 3 µfluid | 4 µfluid | 5 µfluid | 6B µfluid | 7F Native |
|---|---|---|---|---|---|---|
| PS conc.(mg/ml) | 4 | 2.0 | 2.5 | 7.5 | 10 | 3.0 |
| PS dissolution | NaCl 2M | NaCl 2M | NaCl 2M | NaCl 2M | NaCl 2M | NaCl 2M |
| PD conc.(mg/ml) | 10.0 | 5.0 | 5.0 | 5.0 NaCl 2M | 20 (DT) NaCl 2M | 5.0 |
| Initial PD/PS Ratio (w/w) | 1.2/1 | 1/1 | 1/1 | 1/1 | 1.5/1 | 1/1 |
| CDAP conc. (mg/mg PS) | 1.50 | 0.75 | 1.5 | 2 | 1.5 | 0.75 |
| $pH_a = pH_c = pH_g$ | 9.0/9.0/9.0 | 9.5/9.5/9.0 | 9.5/9.5/9.0 | 9.0/9.0/9.0 | 9.5/9.5/9.0 | 9/9/9 |
| Coupling time | 60 mins | 60 mins | 60 mins | 60 mins | 60 mins | 60 mins |

| Serotype | 9V Native | 14 Native | 18C µfluid | 19F µfluid | 23F µfluid |
|---|---|---|---|---|---|
| PS conc.(mg/ml) | 1.75 | 2.5 | 5.0 | 9.0 | 10 |
| PS dissolution | NaCl 2M | NaCl 2M | NaCl 2M | NaCl 2M | NaCl 2M |
| Carrier protein conc.(mg/ml) | 5.0 | 5.0 | 5.0 | 20 (DT) | 10 (DT) |
| Initial carrier protein/PS Ratio (w/w) | 0.75/1 | 0.75/1 | 1.2/1 | 1.5/1 | 1.5/1 |
| CDAP conc. (mg/mg PS) | 0.75 | 0.75 | 1.5 | 1.5 | 0.75 |
| $pH_a = pH_c = pH_g$ | 8.5/8.5/9.0 | 9.0/9.0/9.0 | 9.0/9.0/9.0 | 9.0/9.0/9.0 | 9.5/9.5/9.0 |
| Coupling time | 60 mins | 60 mins | 30 mins | 60 mins | 60 mins |

TABLE 7

Specific activation/coupling/quenching conditions of PS
S. pneumoniae-Protein D/DTconjugates for the 11 Pn-PD&Di-007 study

| Serotype | 1 Native | 3 µfluid | 4 Native | 5 Native | 6B Native | 7F µfluid |
|---|---|---|---|---|---|---|
| PS conc. (mg/ml) | 1.5 | 2.0 | 2 | 7.5 | 5.5 | 5.0 |
| PS dissolution | NaCl 150 mM | NaCl 2M | WFI | WFI | NaCl 2M | NaCl 2M |
| PD conc. (mg/ml) | 5.0 | 5.0 | 5.0 | 5.0 | 5 | 10 |
| Initial PD/PS Ratio (w/w) | 0.7/1 | 1/1 | 1 | 1/1 | 1/1 | 1.2/1 |
| CDAP conc. (mg/mg PS) | 0.75 | 0.75 | 0.75 | 0.75 | 0.75 | 0.75 |
| $pH_a = pH_c = pH_q$ | 9.0/9.0/9.0 | 9.5/9.5/9.0 | 8.8/8.8/9.0 | 9.0/9.0/9.0 | 9.5/9.5/9.0 | 9.5./9.5/9 |
| Coupling time | 60 mins | 60 mins | 45 mins | 40 mins | 60 mins | 60 mins |

| Serotype | 9V µfluid | 14 µfluid | 18C Native | 19F µfluid | 19F µfluid | 23F µfluid |
|---|---|---|---|---|---|---|
| PS conc. (mg/ml) | 5.0 | 5.0 | 1.75 | 9.0 | 10.0 | 9.5 |
| PS dissolution | NaCl 2M | NaCl 2M | WFI | NaCl 2M | NaCl 2M | NaCl 2M |
| Carrier protein conc. (mg/ml) | 10 | 10.0 | 5.0 | 20 (DT) | 5.0 (PD) | 10 |
| Initial carrier protein/PS Ratio (w/w) | 1.2/1 | 1.2/1 | 1.2/1 | 1.5/1 | 1.2/1 | 1/1 |
| CDAP conc. (mg/mg PS) | 0.5 | 0.75 | 0.75 | 1.5 | 0.75 | 0.75 |
| $pH_a = pH_c = pH_q$ | 9.5/9.5/9.0 | 9.5/9.5/9.0 | 9.0/9.0/9.0 | 9.0/9.0/9.0 | 9.0/9.0/9.0 | 9.5/9.5/9.0 |
| Coupling time | 60 mins | 60 mins | 45 mins | 120 mins | 120 mins | 60 mins |

TABLE 8

Percentage of subjects with 19F antibody concentration ≥0.20 μg/mL and 19F antibody Geometric mean antibody concentrations (GMCs with 95% CI; μg/mL) one month following 1 μg 19F-PD, 3 μg 19F-DT or PREVNAR ® (2 μg 19F-CRM) primary vaccination (Total cohort)

| | 11Pn-PD&Di-001 (22F-ELISA) | | | 11Pn-PD&Di-007 (22F-ELISA) | | |
|---|---|---|---|---|---|---|
| Group | N | % ≥ 0.20 μg/mL (95% CI) | GMC (μg/mL) (95% CI) | N | % ≥ 0.20 μg/mL (95% CI) | GMC (μg/mL) (95% CI) |
| 11Pn-PD | 152 | 98.7 (95.3-99.8) | 1.93 (1.67-2.22) | 50 | 100 (92.9-100) | 2.78 (2.31-3.36) |
| 19F-DT Form 1[Γ] | 146 | 99.3 (96.2-100) | 2.88 (2.45-3.38) | — | — | — |
| 19F-DT Form 2[Γ] | 150 | 96.0 (91.5-98.5) | 2.43 (2.01-2.94) | — | — | — |
| 19F-DT Form 3[Γ] | — | — | — | 50 | 96.0 (86.3-99.5) | 3.70 (2.58-5.30) |
| PREVNAR ® | 148 | 98.6 (95.2-99.8) | 2.98 (2.60-3.41) | 41 | 97.6 (87.1-99.9) | 2.91 (2.15-3.94) |

[Γ]The composition of the different formulations is provided in table 4.

TABLE 9

Percentage of subjects with 19F OPA titer ≥ 1:8 and 19F OPA GMTs one month following primary vaccination with 1 μg 19F-PD, 3 μg 19F-DT or PREVNAR ® (2 μg 19F-CRM) (Total cohort)

| | 11Pn-PD&Di-001 | | | 11Pn-PD&Di-007 | | |
|---|---|---|---|---|---|---|
| Group | N | ≥1:8 (95% CI) | GMT (95% CI) | N | ≥1:8 (95% CI) | GMT (95% CI) |
| 11Pn-PD | 136 | 84.6 (77.4-90.2) | 77.8 (58.1-104.4) | 46 | 95.7 (85.2-99.5) | 167.8 (118.1-238.6) |
| 19F-DT Form 1[Γ] | 137 | 95.6 (90.7-98.4) | 263.2 (209.4-330.7) | — | — | — |
| 19F-DT Form 2[Γ] | 139 | 92.1 (86.3-96.0) | 218.9 (166.5-287.9) | — | — | — |
| 19F-DT Form 3[Γ] | — | — | — | 49 | 91.8 (80.4-97.7) | 403.1 (225.7-719.9) |
| PREVNAR ® | 131 | 86.3 (79.2-91.6) | 82.6 (61.1-111.6) | 38 | 81.6 (65.7-92.3) | 65.0 (37.7-112.2) |

[Γ]The composition of the different formulations is provided in Error! Reference source not found.4.

TABLE 10

Percentage of subjects with 19F antibody concentration ≥0.20 μg/mL and 19F antibody GMCs (μg/mL) prior to and one month following 23-valent plain polysaccharide booster in children primed with 1 μg 19F-PD, 3 μg 19F-DT or PREVNAR ® (2 μg 19F-CRM) (Total cohort)

| | 11Pn-PD&Di-002 (22F ELISA) | | | | | |
|---|---|---|---|---|---|---|
| | Prior to booster vaccination | | | One month post 23-valent PS booster | | |
| Primary group | N | % ≥ 0.20 μg/mL (95% CI) | GMC (μg/ml) (95% CI) | N | % ≥ 0.20 μg/mL (95% CI) | GMC (μg/ml) (95% CI) |
| 11Pn-PD | 70 | 77.1 (65.6-86.3) | 0.67 (0.45-0.98) | 67 | 94.0 (85.4-98.3) | 11.50 (7.76-17.03) |
| 19F-DT Form 1[Γ] | 68 | 91.2 (81.8-96.7) | 0.71 (0.54-0.94) | 69 | 98.6 (92.2-100) | 14.50 (10.47-20.07) |
| 19F-DT Form 2[Γ] | 74 | 81.1 (70.3-89.3) | 0.59 (0.43-0.80) | 72 | 95.8 (88.3-99.1) | 9.90 (6.74-14.54) |
| PREVNAR ® | 65 | 64.6 (51.8-76.1) | 0.40 (0.27-0.60) | 67 | 100 (94.6-100) | 9.40 (6.95-12.71) |

[Γ]The composition of the different formulations is provided in Error! Reference source not found.4.

TABLE 11

Percentage of subjects with 19F OPA titer ≥ 1:8 and 19F OPA GMTs prior to and one month following 23-valent plain polysaccharide booster in children primed with 1 μg 19F-PD, 3 μg 19F-DT or PREVNAR® (2 μg 19F-CRM) (Total cohort)

| | 11Pn-PD&Di-002 | | | | | |
|---|---|---|---|---|---|---|
| | Prior to booster vaccination | | | One month post 23-valent PS booster | | |
| Primary group | N | % ≥ 1:8 (95% CI) | GMT (95% CI) | N | % ≥ 1:8 (95% CI) | GMT (95% CI) |
| 11Pn-PD | 29 | 27.6 (12.7-47.2) | 10.9 (5.0-23.7) | 28 | 82.1 (63.1-93.9) | 408.0 (157.3-1058.3) |
| 19F-DT Form 1^Γ | 19 | 47.4 (24.4-71.1) | 18.1 (7.2-45.7) | 18 | 94.4 (72.7-99.9) | 1063.8 (386.6-2927.5) |
| 19F-DT Form 2^Γ | 27 | 33.3 (16.5-54.0) | 8.5 (4.7-15.3) | 28 | 100 (87.7-100) | 957.6 (552.8-1659.0) |
| PREVNAR® | 24 | 12.5 (2.7-32.4) | 8.1 (3.4-19.6) | 23 | 82.6 (61.2-95.0) | 380.9 (133.2-1089.5) |

^Γ The composition of the different formulations is provided in Table 4.

TABLE 12

Percentage of subjects with antibody concentrations ≥0.2 μg/mL, OPA ≥ 1:8 and GMCs/GMTs against 19F pneumococci one month following 11Pn-PD or PREVNAR® booster in children primed with 1 μg 19F-PD, 3 μg 19F-DT or PREVNAR® (2 μg 19F-CRM) (Total cohort)

| | 11Pn-PD&Di-002 | | | | | |
|---|---|---|---|---|---|---|
| | 22F-ELISA assay | | | OPA assay | | |
| Primary group | N | % ≥ 0.20 μg/mL (95% CI) | GMC (μg/ml) (95% CI) | N | % ≥ 1:8 (95% CI) | GMT (95% CI) |
| 11Pn-PD | 70 | 100 (94.9-100) | 4.52 (3.7-5.5) | 21 | 100 (83.9-100) | 255.6 (135.5-481.9) |
| 19F-DT Form 1^Γ | 66 | 98.5 (91.8-100) | 3.45 (2.8-4.3) | 23 | 95.7 (78.1-99.9) | 374.0 (192.6-726.2) |
| 19F-DT Form 2^Γ | 70 | 98.6 (92.3-100) | 3.80 (2.9-4.9) | 29 | 96.6 (82.2-99.9) | 249.1 (144.7-428.7) |
| PREVNAR® | 69 | 97.1 (89.9-99.6) | 2.56 (2.0-3.3) | 31 | 96.8 (83.3-99.9) | 528.7 (319.4-875.2) |

^Γ The composition of the different formulations is provided in Table 4.

TABLE 13

Percentage of subjects with antibody concentrations ≥0.2 μg/mL, OPA ≥ 1:8 and GMCs/GMTs against 19A pneumococci one month following primary vaccination with 1 μg 19F-PD, 3 μg 19F-DT or PREVNAR® (2 μg 19F-CRM) (Total cohort)

| | 11Pn-PD&Di-001 | | | | | |
|---|---|---|---|---|---|---|
| | 22F-ELISA assay | | | OPA assay | | |
| Group | N | % ≥ 0.20 μg/mL (95% CI) | GMC (μg/mL) (95% CI) | N | % ≥ 1:8 (95% CI) | GMT (95% CI) |
| 11Pn-PD | 45 | 28.9 (16.4-44.3) | 0.09 (0.07-0.11) | 52 | 7.7 (2.1-18.5) | 5.2 (4.0-6.8) |
| 19F-DT Form 2^Γ | 51 | 29.4 (17.5-43.8) | 0.11 (0.08-0.16) | 59 | 27.1 (16.4-40.3) | 12.4 (7.6-20.3) |
| PREVNAR® | 55 | 18.2 (9.1-30.9) | 0.10 (0.08-0.12) | 61 | 3.3 (0.4-11.3) | 4.6 (3.8-5.6) |

^Γ The composition of the different formulations is provided in Table 4

Example 5

Adjuvant Experiments in Preclinical Models: Impact on the Immunogenicty of Pneumococcal 11-Valent Polysaccharide Conjugates in Elderly Rhesus Monkeys To optimize the response elicited to conjugate pneumococcal vaccines in the elderly population, GSK formulated an 11-valent polysaccharide (PS) conjugate vaccine with a novel adjuvant Adjuvant C—see below.

Groups of 5 elderly Rhesus monkeys (14 to 28 years-old) were immunized intramuscularly (IM) at days 0 and 28 with 500 μl of either 11-valent PS conjugates adsorbed onto 315 μg of AlPO4 or 11-valent PS conjugates admixed with Adjuvant C.

In both vaccine formulations, the 11-valent PS conjugates were each composed of the following conjugates PS1-PD, PS3-PD, PS4-PD, PS5-PD, PS7F-PD, PS9V-PD, PS14-PD, PS18C-PD, PS19F-PD, PS23F-DT and PS6B-DT. The vaccine used was ⅕ dose of of the human dose of the vaccine (5 μg of each saccharide per human dose except for 6B [10 μg]) conjugated according to Table 6 conditions (Example 4), except 19F was made according to the following CDAP process conditions: sized saccharide at 9 mg/ml, PD at 5 mg/ml, an initial PD/PS ratio of 1.2/1, a CDAP concentration of 0.75 mg/mg PS, pHa=pHc=pHq 9.0/9.0/9.0 and a coupling time of 60 min.

Anti-PS ELISA IgG levels and opsono-phagocytosis titres were dosed in sera collected at day 42. Anti-PS3 memory B cell frequencies were measured by Elispot from peripheral blood cells collected at day 42.

Figure 2:
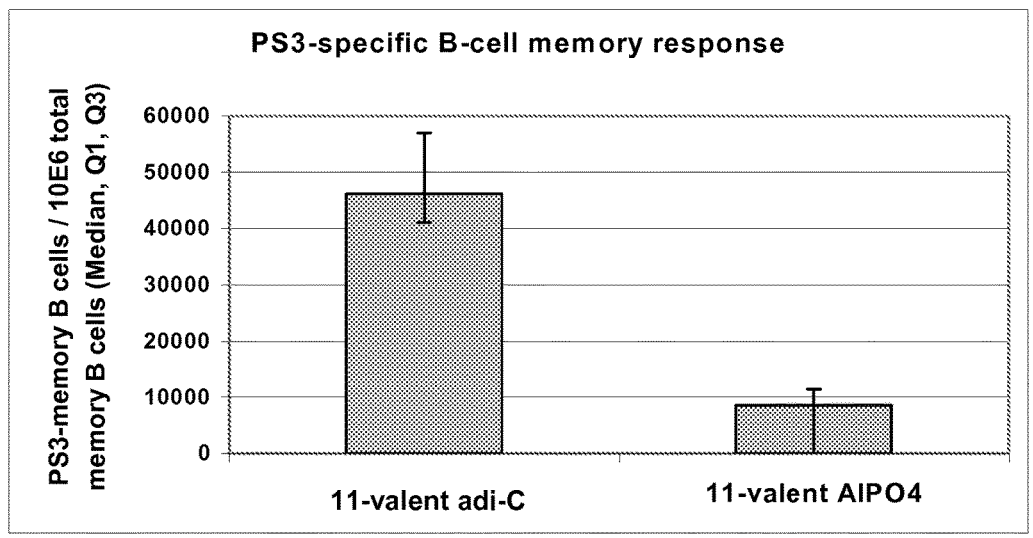
FIG. 2 Conjugate immunogenicity in elderly Rhesus monkeys (post-II anti-PS3 memory B cell frequencies) Bar chart showing memory B cells for PS3 after inoculation with the 11 valent conjugate in adjuvant C or aluminium phosphate adjuvant.

According to the results shown here below, Adjuvant C significantly improved the immunogenicity of 11-valent PS conjugates versus conjugates with AlPO4 in elderly monkeys. The novel adjuvant enhanced the IgG responses to PS (FIG. 1) and the opsono-phagocytosis antibody titres (Table 14). There was also supportive evidence that the frequency of PS3-specific memory B cells is increased by the use of Adjuvant C (FIG. 2).

B cells. Results are expressed as a frequency of PS specific memory B cells within a million of memory B cells.

The study shows that Adjuvant C may be able to alleviate the known problem of PS3 boostability (see 5th International Symposium on Pneumococci and Pneumococcal Diseases, Apr. 2-6 2006, Alice Springs, Central Australia. Specificities of immune responses against a serotype 3 pneumococcal conjugate. Schuerman L, Prymula R, Poolman J. Abstract book p 245, P010.06).

Example 6

Effectiveness of Detoxified Pneumolysin (dPly) as a Protein Carrier to Enhance the Immunogenicity of PS 19F in Young Balb/c Mice Groups of 40 female Balb/c mice (4-weeks old) were immunized IM at days 0, 14 and 28 with 50 μl of either 4-valent plain PS or 4-valent dPly-conjugated PS, both admixed with Adjuvant C.

Both vaccine formulations were composed of 0.1 μg (quantity of saccharide) of each of the following PS: PS8, PS12F, PS19F and PS22F.

Anti-PS ELISA IgG levels were dosed in sera collected at day 42.

Figure 3:
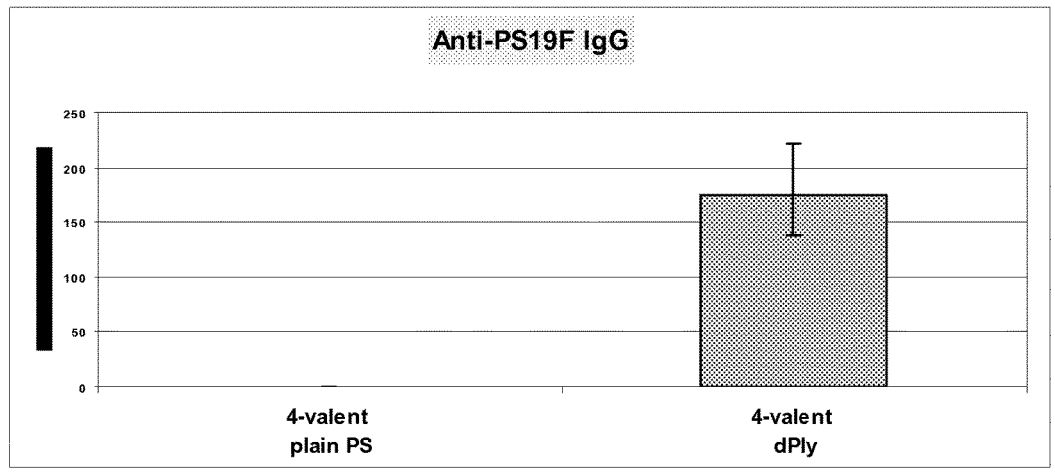
FIG. 3 Anti-PS19F IgG immunogenicity in Balb/c mice (post-III IgG levels) Bar chart showing anti polysaccharide 19F immunogenicity in Balb/C mice for the 4-valent plain polysaccharides and the 4-valent dPly conjugates.

The anti-PS19F response, shown as an example in FIG. 3, was strongly enhanced in mice given 4-valent dPly conjugates compared to mice immunized with the plain PS. The same improvement was observed for the anti-PS8, 12F and 22F IgG responses (data not shown).

Example 7

Effectiveness of Pneumococcal Histidine Triad Protein D (PhtD) as a Protein Carrier to Enhance the Immunogenicity of PS 22F in Young Balb/c Mice Groups of 40 female Balb/c mice (4-weeks old) were immunized IM at days 0, 14 and 28 with 50 μl of either 4-valent plain PS or 4-valent PhtD-conjugated PS, both admixed with Adjuvant C.

TABLE 14

Conjugate immunogenicity in elderly Rhesus monkeys (post-II opsono-phagocytosis titres)

| | | PS1 | PS3 | PS4 | PS5 | PS6B | PS7F | PS9V | PS14 | PS18C | PS19F | PS23F |
|---|---|---|---|---|---|---|---|---|---|---|---|---|
| 11-valent | Pre-immune | <8 | 5 | <8 | 5 | <8 | 16 | <8 | <8 | <8 | <8 | <8 |
| AlPO4 | day 14 post II | 8 | 181 | 64 | 49 | 64 | 4096 | 42 | 37 | 169 | 64 | <64 |
| 11 valent | Pre-immune | 5 | 9 | <8 | 5 | 8 | 37 | <8 | <8 | <8 | <8 | <8 |
| Adj-C | day 14 post II | 776 | 1351 | 891 | 676 | 6208 | 16384 | 111 | 161 | 7132 | 2048 | <64 |

B Cell Elispot

The principle of the assay relies on the fact that memory B cells mature into plasma cells in vitro following cultivation with CpG for 5 days. In vitro generated antigen-specific plasma cells can be easily detected and therefore be enumerated using the B-cell elispot assay. The number of specific plasma cells mirrors the frequency of memory B cells at the onset of the culture.

Briefly, in vitro generated plasma cells are incubated in culture plates coated with antigen. Antigen-specific plasma cells form antibody/antigen spots, which are detected by conventional immuno-enzymatic procedure and enumerated as memory B cells.

In the present study, Polysaccharides have been used to coat culture plates in order to enumerate respective memory Both vaccine formulations were composed of 0.1 μg (quantity of saccharide) of each of the following PS: PS8, PS12F, PS19F and PS22F.

Anti-PS ELISA IgG levels were dosed in sera collected at day 42.

Figure 4:
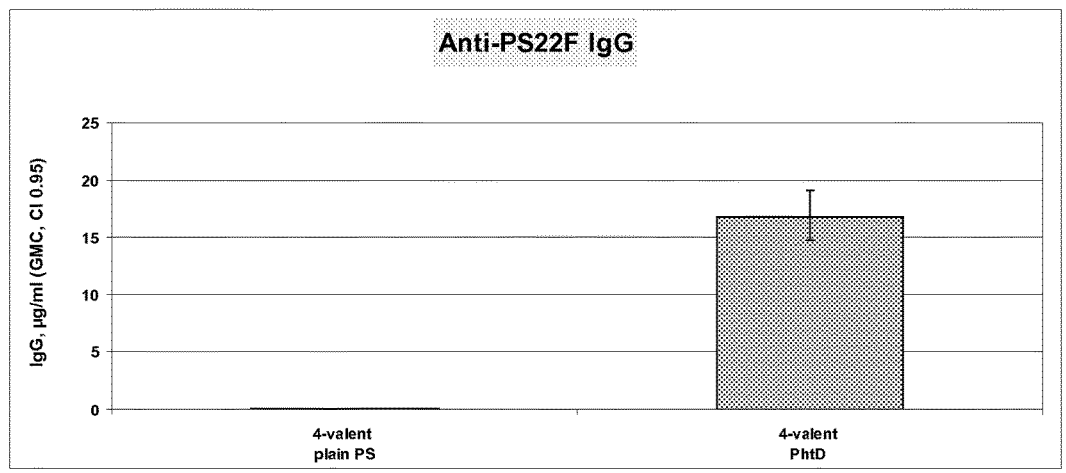
FIG. 4 PS22F immunogenicity in Balb/c mice (post-III IgG levels) Bar chart showing anti polysaccharide 22F immunogenicity in Balb/C mice for the 4-valent plain polysaccharides and the 4-valent PhtD conjugates.

The anti-PS22F response, shown as an example in FIG. 4, was strongly enhanced in mice given 4-valent PhtD conjugates compared to mice immunized with the plain PS. The same improvement was observed for the anti-PS8, 12F and 19F IgG responses (data not shown).

Example 8

Immunogenicity in Elderly C57Bl Mice of 13-Valent PS Conjugates Containing 19A-d Ply and 22F-PhtD Groups of 30 old C57B1 mice (>69-weeks old) were immunized IM at days 0, 14 and 28 with 50 μl of either 11-valent PS conjugates or 13-valent PS conjugates, both admixed with Adjuvant C (see below).

The 11-valent vaccine formulation was composed of 0.1 μg saccharide of each of the following conjugates: PS1-PD, PS3-PD, PS4-PD, PS5-PD, PS6B-PD, PS7F-PD, PS9V-PD, PS14-PD, PS18C-TT, PS19F-DT and PS23F-PD (see Table 1 and comment on 11 valent vaccine discussed under Table 2). The 13-valent vaccine formulation contained in addition 0.1 μg of PS19A-dPly and PS22F-PhtD conjugates (see Table 1 and comment on 13 valent vaccine discussed under Table 2 [using directly-conjugated 22F]). In group 2 and 4 the pneumolysin carrier was detoxified with GMBS treatment, in group 3 and 5 it was done with formaldehyde (methods described in WO 04/81515). In groups 2 and 3 PhtD was used to conjugate PS 22F, in Groups 4 and 5 a PhtD_E fusion (the construct VP147 from WO 03/054007) was used. In group 6 19A was conjugated to diphtheria toxoid and 22F to protein D.

Anti-PS19A and 22F ELISA IgG levels were assessed in individual sera collected at day 42 using the following procedure. The ELISA IgG response generated to the other PS was measured in pooled sera.

Mouse Serology Procedures:

The anti-PS19A ELISA IgG levels were assessed in sera collected at day 42 using the procedure described here below:

Microplates were coated for 2 hours at 37° C. with purified pneumococcal PS type 19A (10 μg/ml) in PBS buffer. Plates were washed four times with NaCl 0.9% mM-TWEEN® 20 0.05%. Sera were incubated for 1 hour at 37° C. with 50 μg/ml of CPS (V/V) in PBS 0.05% TWEEN® 20. Sera were added to the microwells and serially diluted (two-fold dilution step) in PBS-BSA 0.05% TWEEN® 0.05%. Plates were incubated under agitation for 30 minutes at room temperature. Plates were washed as above and an anti-mouse IgG-peroxidase conjugate (diluted 1/2500) was added and plates were incubated for 30 minutes at RT. After washing, the substrate (4 mg of OPDA in 10 ml of citrate 0.1M pH 4.5 and 5 μl of $H_2O_2$) was added to each well for 15 minutes. The reaction was stopped by addition of HCl 1 N. Absorbance was read at 490-620 nm using a spectrophotometer. The color developed is directly proportional to the amount of antibody present in the serum.

The level of the anti-PS19A IgG present in the sera samples is determined by comparison to the reference curve and expressed in μg/ml. A reference curve was generated for each plate from ELISA results for known amount of serum added.

The anti-PS22F ELISA IgG levels were assessed in sera collected at day 42 using the procedure described here below:

Microplates were coated for 2 hours at 37° C. with purified pneumococcal PS type 22F (10 μg/ml) in PBS buffer. Plates were washed four times with NaCl 0.9% mM-TWEEN® 20 0.05%. Sera were incubated for 1 hour at 37° C. with 50 μg/ml of CPS (V/V) in PBS 0.05% TWEEN® 20. Sera were added to the microwells and serially diluted (two-fold dilution step) in PBS-BSA 0.05% TWEEN® 0.05%. Plates were incubated under agitation for 30 minutes at room temperature. Plates were washed as above and an anti-mouse IgG antibodies peroxidase conjugate (diluted 1/2500) was added and plates were incubated for 30 minutes at RT. After washing, the substrate (4 mg of OPDA in 10 ml of citrate 0.1M pH 4.5 and 5 μl of $H_2O_2$) was added to each well for 15 minutes. The reaction was stopped by addition of HCl 1N. Absorbance was read at 490-620 nm using a spectrophotometer. The color developed is directly proportional to the amount of antibody present in the serum.

The level of the anti-PS22F IgG present in the unknown sera is determined by comparison to the reference curve serum added on each plate and expressed in μg/ml.

The immune responses directed against all other serotypes were realized according to the same procedures except that the sera of mice were pooled.

19A-dPly and 22F-PhtD administered within the 13-valent conjugate vaccine formulation were shown immunogenic in old C57B1 mice (Table 15). The immune response induced against other PS was not negatively impacted in mice given the 13-valent formulation compared to those immunized with the 11-valent formulation.

TABLE 15

PS immunogenicity in old C57Bl mice (post-III IgG levels)
Old C57 Black mice

| | ELISA | GROUP 1<br>11V<br>0.1 μg/50 μl<br>Adj C | GROUP 2<br>11V<br>19A-dPly<br>gmbs<br>22F-PhtD<br>0.1 μg/50 μl<br>Adj C | GROUP 3<br>11V<br>19A-dPly<br>formol<br>22F-PhtD<br>0.1 μg/50 μl<br>Adj C | GROUP 4<br>11V<br>19A-dPly<br>gmbs<br>22F-PhtD-E<br>0.1 μg/50 μl<br>Adj C | GROUP 5<br>11V<br>19A-dPly<br>formol<br>22F-PhtD-E<br>0.1 μg/50 μl<br>Adj C | GROUP 6<br>11V<br>19A-DT<br>22F-PD<br>0.1 μg/50 μl<br>Adj C |
|---|---|---|---|---|---|---|---|
| 1 | average Pool | 19.30 | 20.20 | 24.40 | 12.80 | 12.10 | 13.60 |
| 3 | average Pool | 6.32 | 4.84 | 5.21 | 6.74 | 2.38 | 2.54 |
| 4 | average Pool | 60.9 | 67.1 | 51.4 | 47.4 | 45.5 | 41.1 |
| 5 | average Pool | 1.34 | 3.81 | 3.06 | 2.75 | 1.26 | 1.23 |
| 6B | average Pool | 4.41 | 4.12 | 5.88 | 1.58 | 2.31 | 5.64 |
| 7F | average Pool | 0.83 | 0.81 | 1.65 | 1.98 | 0.89 | 0.99 |

TABLE 15-continued

PS immunogenicity in old C57Bl mice (post-III IgG levels)

Old C57 Black mice

| ELISA | | GROUP 1<br>11V<br>0.1 μg/50 μl<br>Adj C | GROUP 2<br>11V<br>19A-dPly gmbs<br>22F-PhtD<br>0.1 μg/50 μl<br>Adj C | GROUP 3<br>11V<br>19A-dPly formol<br>22F-PhtD<br>0.1 μg/50 μl<br>Adj C | GROUP 4<br>11V<br>19A-dPly gmbs<br>22F-PhtD-E<br>0.1 μg/50 μl<br>Adj C | GROUP 5<br>11V<br>19A-dPly formol<br>22F-PhtD-E<br>0.1 μg/50 μl<br>Adj C | GROUP 6<br>11V<br>19A-DT<br>22F-PD<br>0.1 μg/50 μl<br>Adj C |
|---|---|---|---|---|---|---|---|
| 9V | average Pool | 13.8 | 23.7 | 20.0 | 13.1 | 15.5 | 9.6 |
| 14 | average Pool | 25.73 | 42.96 | 34.12 | 32.53 | 23.97 | 15.60 |
| 18C | average Pool | 13.4 | 20.1 | 11.9 | 9.1 | 8.3 | 8.4 |
| 19F | average Pool | 57.5 | 90.0 | 63.8 | 36.5 | 47.0 | 69.1 |
| 23F | average Pool | NR | NR | NR | NR | NR | NR |
| 19A | GMC | 0.06 | 0.09 | 0.25 | 0.08 | 0.23 | 0.19 |
| | IC | 0.04-0.1 | 0.05-0.14 | 0.15-0.41 | 0.06-0.12 | 0.14-0.38 | 0.09-0.3 |
| | % sero | 33% | 47% | 83% | 53% | 80% | 73% |
| 22F | GMC | NR | 5.81 | 3.76 | 0.54 | 0.85 | 2.02 |
| | IC | | 3.2-10.6 | 1.8-7.9 | 0.3-1.1 | 0.4-1.7 | 1.2-3.4 |
| | % sero | 0% | 97% | 90% | 77% | 87% | 97% |

NR—no experimental result determined

Mouse OPA Procedure:

Serum samples were heated for 45 min at 56° C. to inactivate any remaining endogenous complement. Twenty-five microliters aliquots of each 1:2 diluted serum sample was two-fold serially diluted in 25 μl OPA buffer (HBSS—14.4% inactivated FBS) per well of a 96-well round bottom microtitre plate. Subsequently, 25 μl of a mixture of activated HL-60 cells (1×107 cells/ml), freshly thawed pneumococcal working seed and freshly thawed baby rabbit complement in an e.g. 4/2/1 ratio (v/v/v) were added to the diluted sera to yield a final volume of 50 μl. The assay plate was incubated for 2 h at 37° C. with orbital shaking (210 rpm) to promote the phagocytic process. The reaction was stopped by laying the microplate on ice for at least 1 min. A 20 μl aliquot of each well of the plate was then transferred into the corresponding well of a 96-well flat bottom microplate and 50 μl of Todd-Hewitt Broth-0.9% agar was added to each well. After overnight incubation at 37° C. and 5% CO2, pneumococcal colonies appearing in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis.

Figure 13:
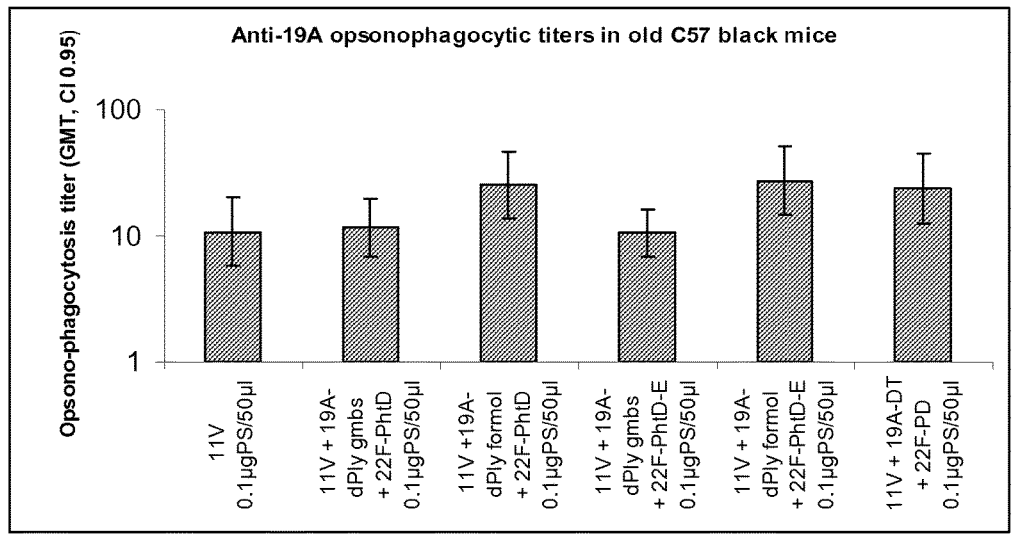
FIG. 13 Anti-19A opsonophagocytic titers in old C57 black mice.
Figure 14:
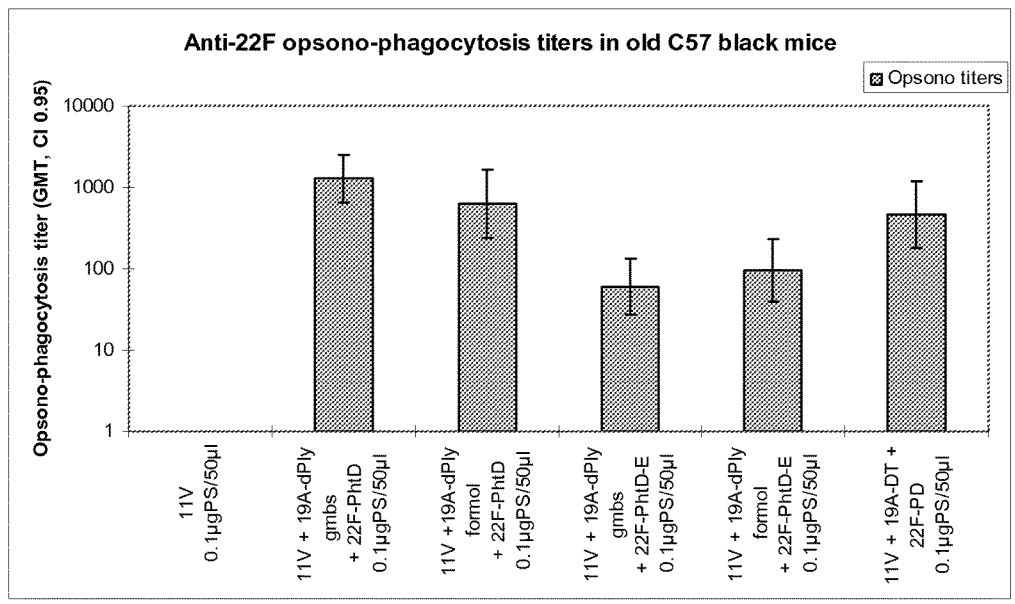
FIG. 14 Anti-22F opsono-phagocytosis titers in old C57 black mice.

The results of opsono-phagocytosis assays are shown in FIGS. 13 and 14.

Example 9

Immunogenicity in Young Balb/c Mice of 13-Valent PS Conjugates Containing 19A-d Ply and 22F-PhtD Groups of 30 young Balb/c mice (4-weeks old) were immunized IM at days 0, 14 and 28 with 50 μl of either 11-valent PS conjugates or 13-valent PS conjugates, both admixed with Adjuvant C (see below).

The 11-valent vaccine formulation was composed of 0.1 μg saccharide of each of the following conjugates: PS1-PD, PS3-PD, PS4-PD, PS5-PD, PS6B-PD, PS7F-PD, PS9V-PD, PS14-PD, PS18C-TT, PS19F-DT and PS23F-PD (see Table 1 and comment on 11 valent vaccine discussed under Table 2). The 13-valent vaccine formulation contained in addition 0.1 μg of PS19A-dPly and PS22F-PhtD conjugates (see Table 1 and comment on 13 valent vaccine discussed under Table 2 [using directly-conjugated 22F]). In group 2 and 4 the pneumolysin carrier was detoxified with GMBS treatment, in group 3 and 5 it was done with formaldehyde (methods described in WO 04/81515). In groups 2 and 3 PhtD was used to conjugate PS 22F, in Groups 4 and 5 a PhtD_E fusion (the construct VP147 from WO 03/054007) was used. In group 6 19A was conjugated to diphtheria toxoid and 22F to protein D.

Anti-PS19A and 22F ELISA IgG levels were dosed in individual sera collected at day 42. The ELISA IgG response generated to the other PS was measured in pooled sera.

19A-dPly and 22F-PhtD administered within the 13-valent conjugate vaccine formulation were shown immunogenic in young Balb/c mice (Table 16). The immune response induced against other PS was not negatively impacted in mice given the 13-valent formulation compared to those immunized with the 11-valent formulation.

ELISAa were carried out as described in example 8.

TABLE 16

PS immunogenicity in young Balb/c mice (post-III IgG levels)
BalbC mice

| | ELISA | GROUP 1<br>11V<br>0.1 µg/50 µl<br>Adj C | GROUP 2<br>11V<br>19A-dPly gmbs<br>22F-PhtD<br>0.1 µg/50 µl<br>Adj C | GROUP 3<br>11V<br>19A-dPly formol<br>22F-PhtD<br>0.1 µg/50 µl<br>Adj C | GROUP 4<br>11V<br>19A-dPly gmbs<br>22F-PhtD-E<br>0.1 µg/50 µl<br>Adj C | GROUP 5<br>11V<br>19A-dPly formol<br>22F-PhtD-E<br>0.1 µg/50 µl<br>Adj C | GROUP 6<br>11V<br>19A-DT<br>22F-PD<br>0.1 µg/50 µl<br>Adj C |
|---|---|---|---|---|---|---|---|
| 1 | average Pool | 131.70 | 101.20 | 83.00 | 82.40 | 67.90 | 85.50 |
| 3 | average Pool | 21.85 | 10.38 | 12.53 | 8.83 | 8.73 | 14.98 |
| 4 | average Pool | 147.4 | 127.0 | 104.4 | 95.0 | 113.6 | 114.2 |
| 5 | average Pool | 21.38 | 20.29 | 18.26 | 18.95 | 18.02 | 23.04 |
| 6B | average Pool | 1.97 | 4.76 | 3.72 | 2.35 | 1.43 | 1.05 |
| 7F | average Pool | 7.69 | 4.58 | 4.77 | 4.24 | 3.92 | 3.94 |
| 9V | average Pool | 30.1 | 30.7 | 26.5 | 21.4 | 23.4 | 28.3 |
| 14 | average Pool | 28.78 | 27.67 | 26.23 | 21.54 | 24.34 | 13.73 |
| 18C | average Pool | 53.4 | 52.37 | 46.5 | 57.8 | 47.8 | 75.8 |
| 19F | average Pool | 186.6 | 157.7 | 169.3 | 178.9 | 181.9 | 223.2 |
| 23F | average Pool | 4.98 | 3.9 | 5.11 | 0.57 | 3.13 | 4.57 |
| 19A | GMC | 0.4 | 32.8 | 25.1 | 21.6 | 18.9 | 23.5 |
| | IC | 0.2-0.6 | 26.4-40.7 | 20.6-30.6 | 17.5-26.7 | 15.1-23.5 | 19.5-28.5 |
| | % sero | 93% | 100% | 100% | 100% | 100% | 100% |
| 22F | GMC | NR | 3.99 | 3.76 | 6.27 | 8.70 | 18.76 |
| | IC | | 1.9-8.42 | 1.8-8 | 3.8-10.4 | 5.4-13.9 | 15.2-23.1 |
| | % sero | 0% | 93% | 100% | 100% | 100% | 100% |

NR—no experimental result determined

Mouse OPA Procedure:

Serum samples were heated for 45 min at 56° C. to inactivate any remaining endogenous complement. Twenty-five microliters aliquots of each 1:2 diluted serum sample was two-fold serially diluted in 25 µl OPA buffer (HBSS-14.4% inactivated FBS) per well of a 96-well round bottom microtitre plate. Subsequently, 25 µl of a mixture of activated HL-60 cells (1×107 cells/ml), freshly thawed pneumococcal working seed and freshly thawed baby rabbit complement in an e.g. 4/2/1 ratio (v/v/v) were added to the diluted sera to yield a final volume of 50 µl. The assay plate was incubated for 2 h at 37° C. with orbital shaking (210 rpm) to promote the phagocytic process. The reaction was stopped by laying the microplate on ice for at least 1 min. A 20 µl aliquot of each well of the plate was then transferred into the corresponding well of a 96-well flat bottom microplate and 50 µl of Todd-Hewitt Broth-0.9% agar was added to each well. After overnight incubation at 37° C. and 5% CO2, pneumococcal colonies appearing in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis.

Figure 15:
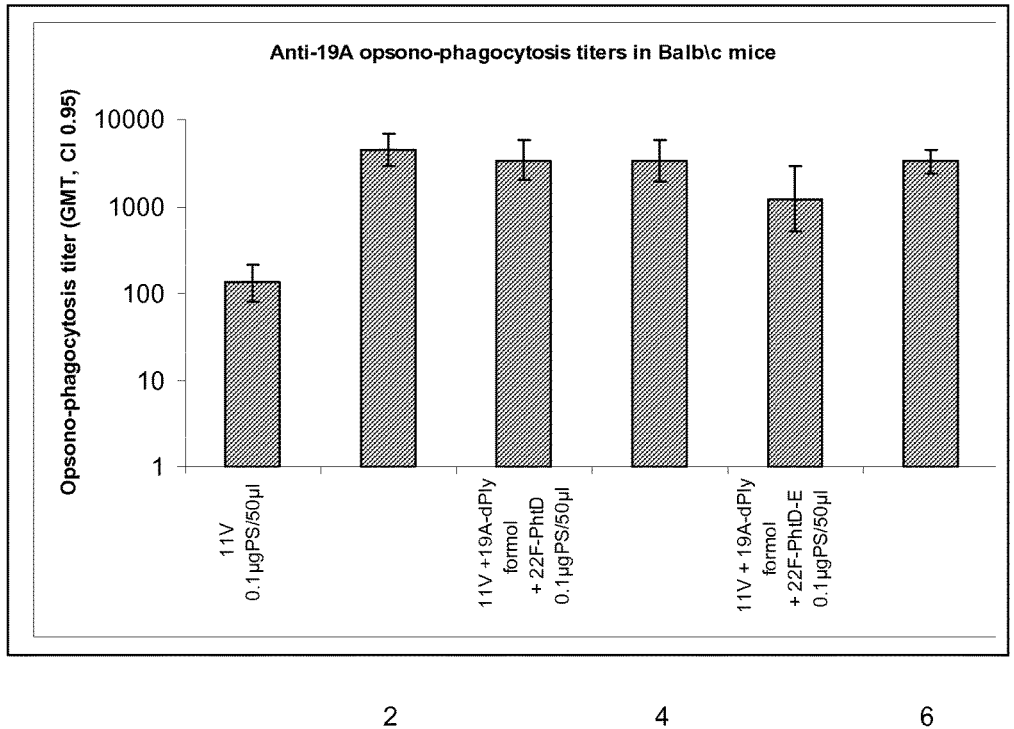
FIG. 15 Anti-19A opsono-phagocytosis titers in Balb/c mice.
Figure 16:
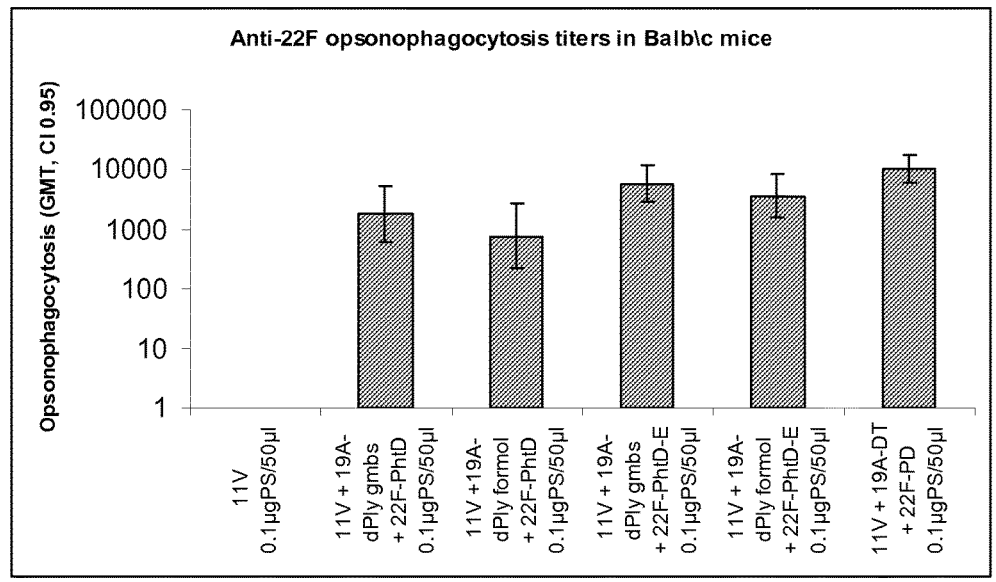
FIG. 16 Anti-22F opsonophagocytosis titers in Balb/c mice.

Results are shown in FIGS. 15 and 16.

Results in Alum Formulations:

Immunogenicity in Young Balb/c Mice of 13-Valent PS Conjugates Containing 19A-dPly and 22F-PhtD Groups of 40 young Balb/c mice (4-weeks old) were immunized IM at days 0, 14 and 28 with 50 µl of either 11-valent PS conjugates or 13-valent PS conjugates, both adsorbed onto AlPO4. INFANRIX® HEXA was co-administered.

The 11-valent vaccine formulation was composed of 0.1 µg saccharide of each of the following conjugates: PS1-PD, PS3-PD, PS4-PD, PS5-PD, PS6B-PD, PS7F-PD, PS9V-PD, PS14-PD, PS18C-TT, PS19F-DT and PS23F-PD (see Table 1 and comment on 11 valent vaccine discussed under Table 2). The 13-valent vaccine formulation contained in addition 0.1 µg of PS19A-dPly and PS22F-PhtD conjugates (see Table 1 and comment on 13 valent vaccine discussed under Table 2 [using directly-conjugated 22F]). In group 2 and 4 the pneumolysin carrier was detoxified with GMBS treatment, in group 3 and 5 it was done with formaldehyde. In groups 2 and 3 PhtD was used to conjugate PS 22F, in Groups 4 and 5 a PhtD_E fusion (the construct VP147 from WO 03/054007) was used. In group 6, 19A was conjugated to diphtheria toxoid and 22F to protein D.

Anti-PS19A and 22F ELISA IgG levels and opsonophagocytosis titers were measured in individual sera collected at day 42. The ELISA IgG response generated to the other PS was measured in pooled sera.

Figure 19:
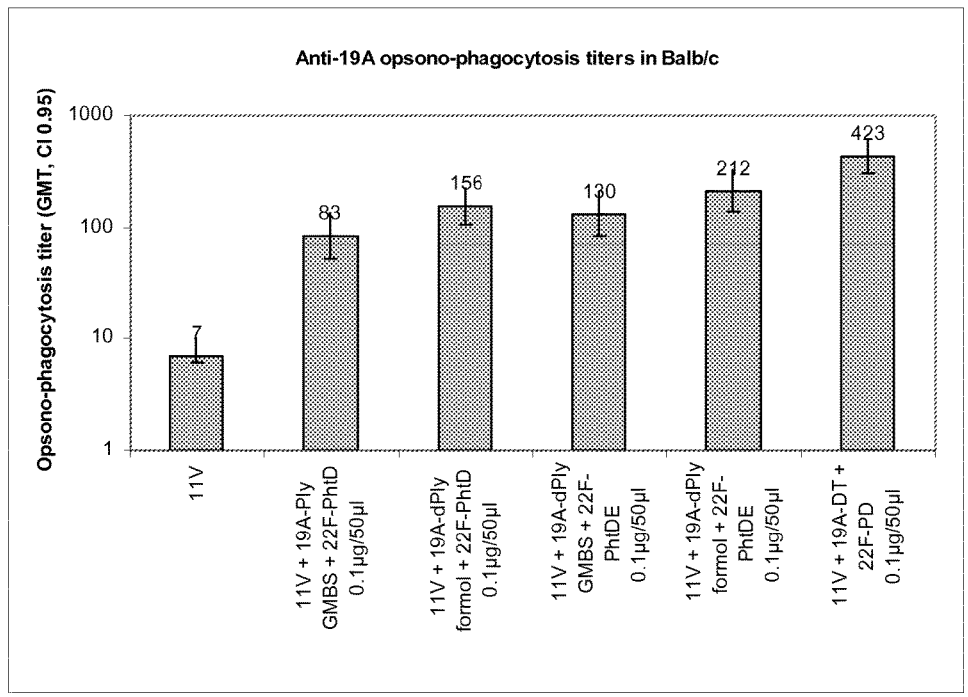
FIG. 19 Anti-19A opsono-phagocytosis titers in Balb/c mice.
Figure 20:
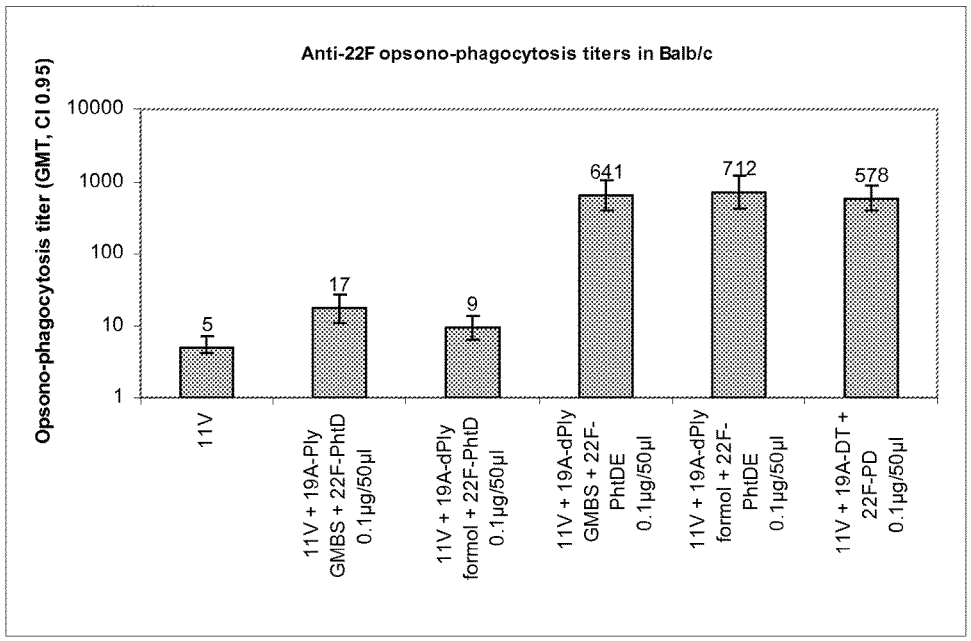
FIG. 20 Anti-22F opsono-phagocytosis titers in Balb/c mice.

19A-dPly and 22F-PhtD administered within the 13-valent conjugate vaccine formulation were shown immunogenic and induced opsono-phagocytic titers in young Balb/c mice (Table 17 and FIGS. 19-20). The immune response induced against the other PS was not negatively impacted in mice given the 13-valent formulation compared to those immunized with the 11-valent formulation.

Opsonophagocytosis assays were used to assess the sera and results are shown in FIGS. 19 and 20.

Table 2 [using directly-conjugated 22F]). In group 2 and 4 the pneumolysin carrier was detoxified with GMBS treatment, in group 3 and 5 it was done with formaldehyde (methods described in WO 04/81515). In groups 2 and 3 PhtD was used to conjugate PS 22F, in Groups 4 and 5 a PhtD_E fusion (the construct VP147 from WO 03/054007) was used. In group 6, 19A was conjugated to diphtheria toxoid and 22F to protein D.

Anti-PS19A and 22F ELISA IgG levels and opsonophagocytosis titers were measured in individual sera collected at day 42. The ELISA IgG response generated to the other PS was measured in pooled sera.

Figure 21:
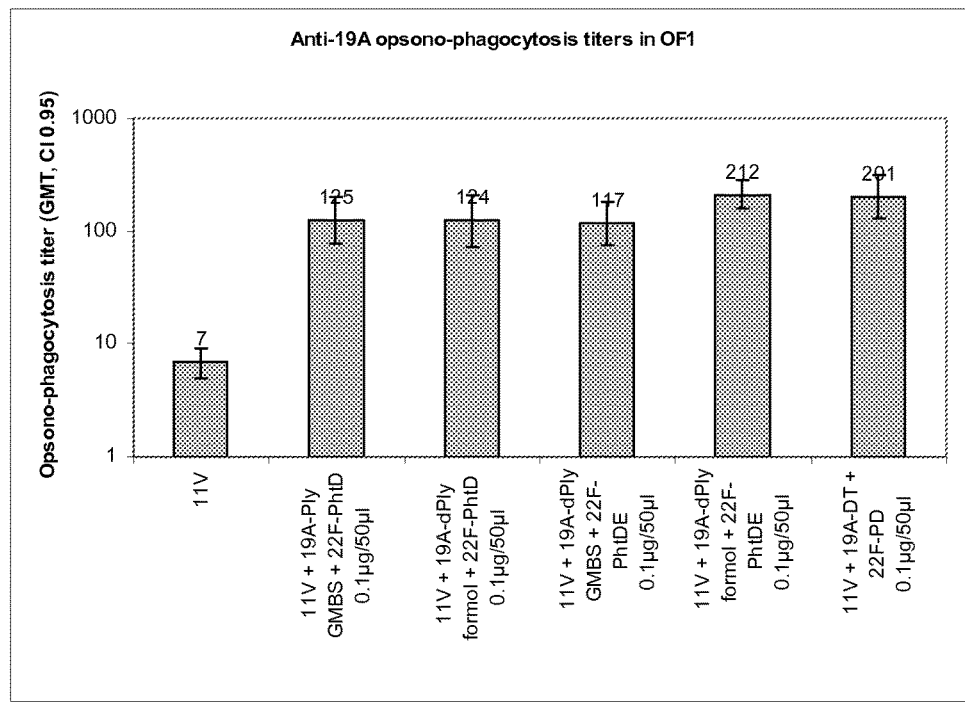
FIG. 21 Anti-19A opsono-phagocytosis titers in OF1.
Figure 22:
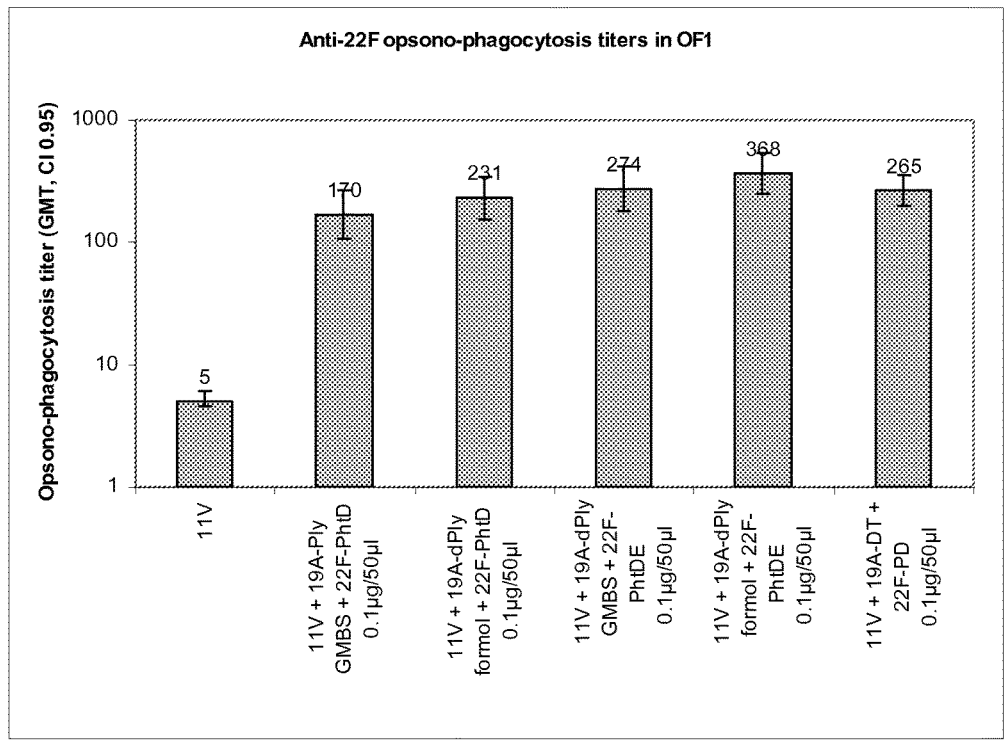
FIG. 22 Anti-22F opsono-phagocytosis titers in OF1.

19A-dPly and 22F-PhtD administered within the 13-valent conjugate vaccine formulation were shown immunogenic and induced opsono-phagocytic titers in young OF1 mice (Table 18 and FIGS. 21-22). The immune response induced against the other PS was not negatively impacted in mice given the 13-valent formulation compared to those immunized with the 11-valent formulation.

The sera were also assessed by opsono-phagocytosis assay and results are shown in FIGS. 21 and 22.

TABLE 17

PS immunogenicity in young Balb/c mice (Post-III IgG levels)

| ELISA POST III | | GROUP 1 11V 1/10 HD SC | GROUP 2 11V 19A-Ply GMBS 22F-PhtD 1/10 HD SC | GROUP 3 11V 19A-dPly formol 22F-PhtD 1/10 HD SC | GROUP 4 11V 19A-dPly GMBS 22F-PhtDE 1/10 HD SC | GROUP 5 11V 19A-dPly formol 22F-PhtDE 1/10 HD SC | GROUP 6 11V 19A-DT 22F-PD 1/10 HD SC |
|---|---|---|---|---|---|---|---|
| 1 | Average pool | 37.535 | 35.312 | 56.839 | 39.781 | 35.739 | 30.270 |
| 3 | Average pool | 9.093 | 9.874 | 7.991 | 10.548 | 7.502 | 8.217 |
| 4 | Average pool | 28.422 | 27.439 | 25.796 | 31.274 | 34.295 | 31.589 |
| 5 | Average pool | 9.256 | 8.668 | 9.6 | 7.551 | 8.869 | 8.309 |
| 6B | Average pool | 0.552 | 0.423 | 0.565 | 0.264 | 0.263 | 0.435 |
| 7F | Average pool | 3.771 | 2.541 | 5.394 | 2.618 | 2.754 | 3.048 |
| 9V | Average pool | 23.447 | 23.479 | 27.394 | 19.072 | 24.282 | 28.017 |
| 14 | Average pool | 25.921 | 26.103 | 24.927 | 16.487 | 20.517 | 24.795 |
| 18C | Average pool | 6.223 | 6.873 | 7.726 | 5.812 | 9.186 | 9.146 |
| 19F | Average pool | 61.271 | 70.498 | 88.336 | 73.879 | 96.521 | 66.484 |
| 23F | Average pool | 1.836 | 0.669 | 0.648 | 0.259 | 1.116 | 0.596 |
| 19A | GMC | 0.065 | 1.797 | 2.256 | 1.950 | 2.128 | 3.640 |
| | 95% CI | NT | 1.206-2.678 | 1.71-2977 | 1.368-2.778 | 1.478-3.064 | 2.793-4.744 |
| | % seropos | 65% | 100% | 100% | 100% | 100% | 100% |
| 22F | GMC | 0.05 | 0.171 | 0.097 | 9.924 | 8.837 | 11.993 |
| | 95% CI | 0.05-0.05 | 0.104-0.282 | 0.0690.141 | 7.19-13.695 | 5.692-13.719 | 9.079-15.842 |
| | % seropos | 0% | 53% | 41% | 100% | 100% | 100% |

Immunogenicity in Young OF1 Mice of 13-Valent PS Conjugates Containing 19A-dPly and 22F-PhtD Groups of 40 young OF1 mice (4-weeks old) were immunized IM at days 0, 14 and 28 with 50 µl of either 11-valent PS conjugates or 13-valent PS conjugates, both adsorbed onto AIPO4. INFANRIX® HEXA was co-administered.

The 11-valent vaccine formulation was composed of 0.1 µg saccharide of each of the following conjugates: PS1-PD, PS3-PD, PS4-PD, PS5-PD, PS6B-PD, PS7F-PD, PS9V-PD, PS14-PD, PS18C-TT, PS19F-DT and PS23F-PD (see Table 1 and comment on 11 valent vaccine discussed under Table 2). The 13-valent vaccine formulation contained in addition 0.1 µg of PS19A-dPly and PS22F-PhtD conjugates (see Table 1 and comment on 13 valent vaccine discussed under

TABLE 18

PS immunogenicity in young OF1 mice (Post-III IgG levels)

| ELISA POST III | | GROUP 1 11V 1/10 HD SC | GROUP 2 11V 19A-Ply GMBS 22F-PhtD 1/10 HD SC | GROUP 3 11V 19A-dPly formol 22F-PhtD 1/10 HD SC | GROUP 4 11V 19A-dPly GMBS 22F-PhtDE 1/10 HD SC | GROUP 5 11V 19A-dPly formol 22F-PhtDE 1/10 HD SC | GROUP 6 11V 19A-DT 22F-PD 1/10 HD SC |
|---|---|---|---|---|---|---|---|
| 1 | Average Pool | 39.668 | 50.854 | 40.384 | 30.108 | 34.753 | 34.487 |
| 3 | Average Pool | 5.562 | 6.266 | 7.243 | 4.665 | 5.510 | 5.188 |
| 4 | Average Pool | 21.979 | 30.567 | 27.65 | 26.646 | 23.159 | 23.296 |
| 5 | Average Pool | 8.884 | 7.986 | 9.495 | 9.303 | 11.318 | 8.984 |
| 6B | Average Pool | 3.158 | 4.139 | 3.48 | 2.44 | 3.784 | 3.137 |
| 7F | Average Pool | 7.134 | 8.843 | 12.471 | 6.497 | 7.607 | 6.607 |
| 9V | Average Pool | 24.052 | 37.153 | 36.348 | 35.168 | 29.746 | 26.592 |
| 14 | Average Pool | 29.027 | 46.057 | 36.605 | 40.883 | 35.026 | 39.186 |

TABLE 18-continued

PS immunogenicity in young OF1 mice (Post-III IgG levels)

|  | ELISA POST III | GROUP 1 11V 1/10 HD SC | GROUP 2 11V 19A-Ply GMBS 22F-PhtD 1/10 HD SC | GROUP 3 11V 19A-dPly formol 22F-PhtD 1/10 HD SC | GROUP 4 11V 19A-dPly GMBS 22F-PhtDE 1/10 HD SC | GROUP 5 11V 19A-dPly formol 22F-PhtDE 1/10 HD SC | GROUP 6 11V 19A-DT 22F-PD 1/10 HD SC |
|---|---|---|---|---|---|---|---|
| 18C | Average Pool | 4.961 | 6.508 | 4.587 | 5.148 | 6.783 | 4.915 |
| 19F | Average Pool | 48.667 | 74.366 | 45.561 | 63.845 | 68.155 | 47.703 |
| 23F | Average Pool | 0.664 | 1.093 | 0.996 | 0.212 | 0.764 | 1.579 |
| 19A | GMC | 0.057 | 1.849 | 2.266 | 1.864 | 3.751 | 2.434 |
|  | 95% CI | NT | 1.132-3.020 | 1.439-3.569 | 1.157-3.004 | 2.825-4.980 | 1.725-3.435 |
|  | % seropos | 48% | 100% | 98% | 95% | 100% | 100% |
| 22F | GMC | 0.064 | 11.190 | 16.196 | 12.431 | 17.319 | 27.490 |
|  | 95% CI | NT | 6.225-20.114 | 9.718-26.992 | 7.95-19.439 | 12.056-24.879 | 22.044-34.281 |
|  | % seropos | 22.5% | 96.9% | 97.5% | 97.5% | 100.0% | 100.0% |

Example 10

Immunogenicity in Guinea Pigs of 13-Valent PS Conjugates Containing 19A-dPly and 22F-PhtD Groups of 20 Young Guinea Pigs (Hartley Strain; 5 weeks old) were immunized IM at days 0, 14 and 28 with 125 µl of either 11-valent PS conjugates or 13-valent PS conjugates, both admixed with Adjuvant C (see below).

The 11-valent vaccine formulation was composed of 0.25 µg saccharide of each of the following conjugates: PS1-PD, PS3-PD, PS4-PD, PS5-PD, PS6B-PD, PS7F-PD, PS9V-PD, PS14-PD, PS18C-TT, PS19F-DT and PS23F-PD (see Table 1 and comment on 11 valent vaccine discussed under Table 2). The 13-valent vaccine formulation contained in addition 0.1 µg of PS19A-dPly and PS22F-PhtD conjugates (see Table 1 and comment on 13 valent vaccine discussed under Table 2 [using directly-conjugated 22F]). In group 2 and 4 the pneumolysin carrier was detoxified with GMBS treatment, in group 3 and 5 it was done with formaldehyde. In groups 2 and 3 PhtD was used to conjugate PS 22F, in Groups 4 and 5 a PhtD_E fusion (the construct VP147 from WO 03/054007) was used. In group 6 19A was conjugated to diphtheria toxoid and 22F to protein D.

Anti-PS19A and 22F ELISA IgG levels were assessed in individual sera collected at day 42 using the following protocol. The ELISA IgG response generated to the other PS was measured in pooled sera.

Guinea Pig Serology Procedures:

The anti-PS19A ELISA IgG levels were assessed in sera collected at day 42 using the procedure described here below:

Microplates were coated for 2 hours at 37° C. with purified pneumococcal PS type 19A (10 µg/ml) in PBS buffer. Plates were washed four times with NaCl 0.9% mM—TWEEN® 20 0.05%. Sera were incubated for 1 hour at 37° C. with 50 µg/ml of CPS (V/V) in PBS 0.05% TWEEN® 20. Sera were added to the microwells and serially diluted (two-fold dilution step) in PBS-BSA 0.05% TWEEN® 0.05%. Plates were incubated under agitation for 30 minutes at room temperature. Plates were washed as above and an anti-guinea pig IgG peroxidase conjugate (diluted 1/1000) was added and plates were incubated for 30 minutes at RT. After washing, the substrate (4 mg of OPDA in 10 ml of citrate 0.1M pH 4.5 and 5 µl of $H_2O_2$) was added to each well for 15 minutes. The reaction was stopped by addition of HCl 1N. Absorbance was read at 490-620 nm using a spectrophotometer. The color developed is directly proportional to the amount of antibody present in the serum.

The level of the anti-PS19A IgG present in the unknown sera is determined by comparison to the reference curve serum added on each plate and expressed in µg/ml.

The anti-PS22F ELISA IgG levels were dosed in sera collected at day 42 using the procedure described here below:

Microplates were coated for 2 hours at 37° C. with purified pneumococcal PS type 22F (10 µg/ml) in PBS buffer. Plates were washed four times with NaCl 0.9% mM-TWEEN® 20 0.05%. Sera were incubated 1 hour at 37° C. with 50 µg/ml of CPS (V/V) in PBS 0.05% TWEEN® 20. Sera were added to the microwells and serially diluted (two-fold dilution step) in PBS-BSA 0.05% TWEEN® 0.05%. Plates were incubated under agitation for 30 minutes at room temperature. Plates were washed as above and an anti-guinea pig IgG peroxidase conjugated (diluted 1/1000) was added and plates were incubated for 30 minutes at RT. After washing, the substrate (4 mg of OPDA in 10 ml of citrate 0.1M pH 4.5 and 5 µl of $H_2O_2$) was added to each well for 15 minutes. The reaction was stopped by addition of HCl 1N. Absorbance was read at 490-620 nm using a spectrophotometer. The color developed is directly proportional to the amount of antibody present in the serum.

The level of the anti-PS22F IgG present in the unknown sera is determined by comparison to the reference curve serum added on each plate and expressed in µg/ml.

The immune responses directed against all other serotypes were realized according to the same procedures except that the sera of guinea pigs were pooled.

TABLE 19

PS immunogenicity in Guinea pigs (post-III IgG levels)
Guinea pigs

| ELISA | | GROUP 1  11V  0.1 µg/50 µl  Adj C | GROUP 2  11V  19A-dPly gmbs  22F-PhtD  0.1 µg/50 µl  Adj C | GROUP 3  11V  19A-dPly formol  22F-PhtD  0.1 µg/50 µl  Adj C | GROUP 4  11V  19A-dPly gmbs  22F-PhtD-E  0.1 µg/50 µl  Adj C | GROUP 5  11V  19A-dPly formol  22F-PhtD-E  0.1 µg/50 µl  Adj C | GROUP 6  11V  19A-DT  22F-PD  0.1 µg/50 µl  Adj C |
|---|---|---|---|---|---|---|---|
| 1 | average Pool | 78.00 | 77.21 | 76.15 | 68.77 | 68.59 | 81.04 |
| 3 | average Pool | 7.75 | 9.31 | 12.73 | 7.94 | 4.75 | 9.59 |
| 4 | average Pool | 130.7 | 94.4 | 132.6 | 166.8 | 85.0 | 101.3 |
| 5 | average Pool | 109.10 | 117.10 | 110.70 | 158.40 | 74.10 | 100.40 |
| 6B | average Pool | 3.14 | 4.26 | 14.4 | 7.63 | 6.3 | 7.52 |
| 7F | average Pool | 154.2 | 216.0 | 240.0 | 181.0 | 142.0 | 179.1 |
| 9V | average Pool | 90.69 | 105.45 | 98.20 | 93.45 | 54.12 | 73.05 |
| 14 | average Pool | 71.19 | 77.18 | 46.53 | 59.67 | 38.47 | 53.69 |
| 18C | average Pool | 109.4 | 122.3 | 137.1 | 79.9 | 73.7 | 83.1 |
| 19F | average Pool | 73.9 | 102.5 | 112.2 | 75.5 | 62.3 | 72.1 |
| 23F | average Pool | 19.19 | 30.74 | 29.44 | 31.52 | 19.13 | 24.94 |
| 19A | GMC | 0.4 | 25.58 | 41.49 | 14.25 | 27.49 | 6.74 |
|  | IC | 0.24-0.68 | 12-54.5 | 24.4-70.5 | 5.9-34.6 | 16.6-45.4 | 4-11.3 |
|  | % sero | 75% | 100% | 100% | 100% | 100% | 100% |
| 22F | GMC | 0.12 | 2.51 | 3.67 | 45.74 | 30.68 | 96.38 |
|  | IC | 0.09-0.16 | 0.94-6.73 | 1.59-8.42 | 29.3-71.4 | 17-53.3 | 73.5-126.4 |
|  | % sero | 10% | 95% | 95% | 100% | 100% | 100% |

Figure 17:
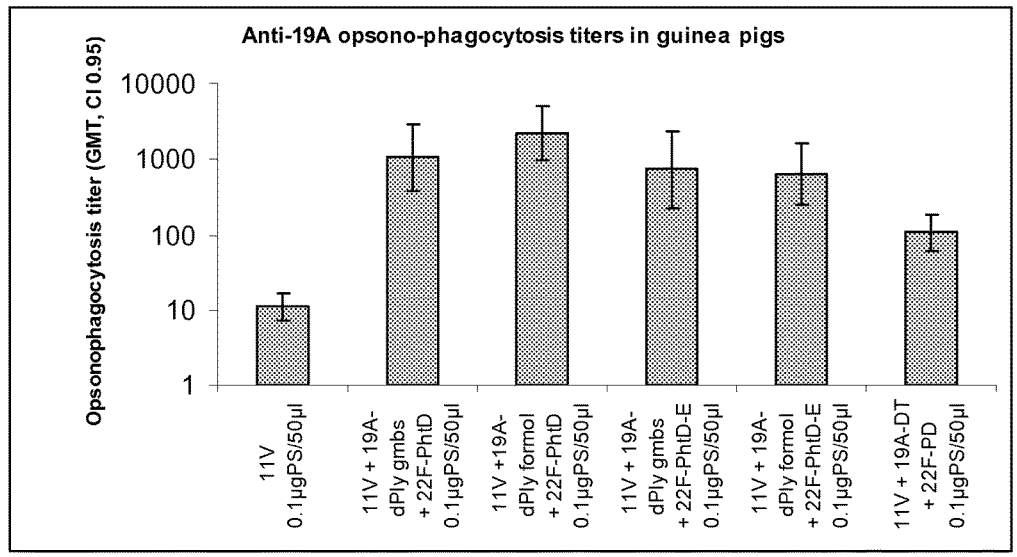
FIG. 17 Anti-19A opsono-phagocytosis titers in guinea pigs.
Figure 18:
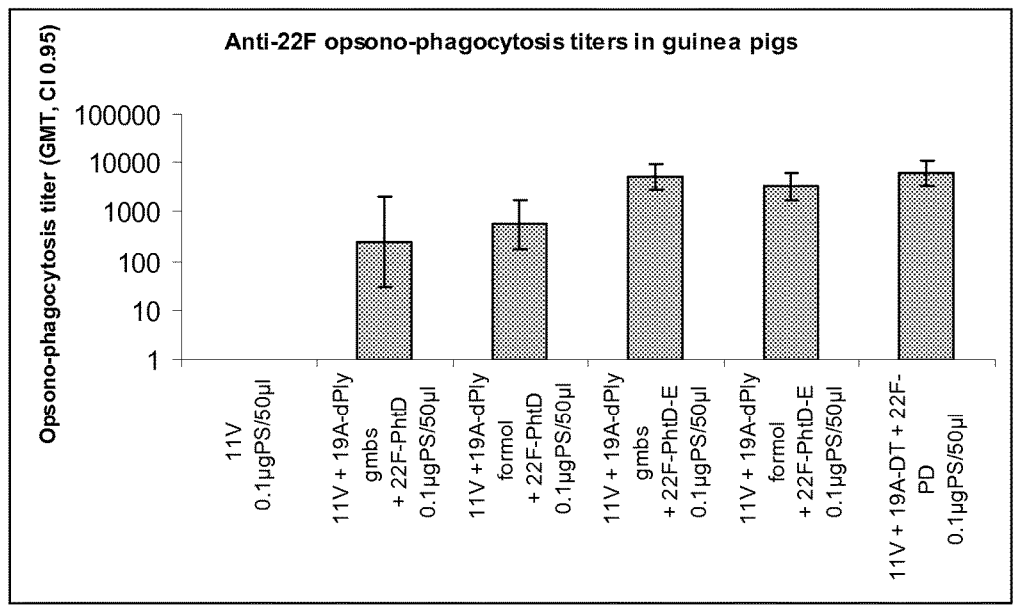
FIG. 18 Anti-22F opsono-phagocytosis titers in guinea pigs.

Opsonophagocytosis assays were also used to test the sera and results are shown in FIGS. 17 and 18.

Example 11

Formulations being Made and Tested a) The following formulations are made (using the 13 valent vaccine from table 1 and serotype 3 from table 5—see comment on 14 valent vaccine discussed under Table 2 [using directly-conjugated 22F or through an ADH linker]). The saccharides are formulated with aluminium phosphate and 3D-MPL as shown below.

| | | | | | | | | | | | |
|---|---|---|---|---|---|---|---|---|---|---|---|
| | | 14V 25 µg MPL  Sum of BAC Aluminium  content -> FF Per Dose: | | | | | 14V 10 µg MPL  Sum of BAC Aluminium  content -> FF Per Dose: | | | | |
| PS | carrier | µg PS | µg MPL | ratio PS/Al 1/x | µg Al | PS | carrier | µg PS | µg MPL | ratio PS/Al 1/x | µg Al |
| 1 | PD | 1 | | 10 | 10 | 1 | PD | 1 | | 10 | 10 |
| 3 | PD | 1 | | 10 | 10 | 3 | PD | 1 | | 10 | 10 |
| 4 | PD | 3 | | 10 | 30 | 4 | PD | 3 | | 10 | 30 |
| 5 | PD | 1 | | 10 | 10 | 5 | PD | 1 | | 10 | 10 |
| 6A | PD | 1 | | 10 | 10 | 6A | PD | 1 | | 10 | 10 |
| 6B | PD | 1 | | 10 | 10 | 6B | PD | 1 | | 10 | 10 |
| 7F | PD | 1 | | 10 | 10 | 7F | PD | 1 | | 10 | 10 |

| | 14V 25 µg MPL Sum of BAC Aluminium content -> FF Per Dose: | | | | | 14V 10 µg MPL Sum of BAC Aluminium content -> FF Per Dose: | | | | |
|---|---|---|---|---|---|---|---|---|---|---|
| PS | carrier | µg PS | µg MPL | ratio PS/AI 1/x | µg AI | PS | carrier | µg PS | µg MPL | ratio PS/AI 1/x | µg AI |
| 9V | PD | 1 | | 10 | 10 | 9V | PD | 1 | | 10 | 10 |
| 14 | PD | 1 | | 10 | 10 | 14 | PD | 1 | | 10 | 10 |
| 18C | $TT_{AH}$ | 3 | | 15 | 45 | 18C | $TT_{AH}$ | 3 | | 15 | 45 |
| 19A | dPly | 3 | | 10 | 30 | 19A | dPly | 3 | | 10 | 30 |
| 19F | DT | 3 | | 10 | 30 | 19F | DT | 3 | | 10 | 30 |
| 22F | PhtD | 3 | | 10 | 30 | 22F | PhtD | 3 | | 10 | 30 |
| 23F | PD | 1 | | 10 | 10 | 23F | PD | 1 | | 10 | 10 |
| | BAC MPL 50/200 | | 25 | 4 | 100 | | BAC MPL 50/200 | | 10 | 4 | 40 |
| | FF Aluminium content | | | Sum = | 355 | | FF Aluminium content | | | Sum = | 295 | b) The same saccharide formulation is adjuvanted with each of the following adjuvants:

In the table herebelow the concentration of the emulsion components per 500 µl dose is shown.

| Ingredients | Adjuvant A1 250 µl o/w emulsion | Adjuvant A2 125 µl o/w emulsion | Adjuvant A3 50 µl o/w emulsion |
|---|---|---|---|
| alpha Tocopherol | 11.88 mg | 5.94 mg | 2.38 mg |
| Squalene | 10.7 mg | 5.35 mg | 2.14 mg |
| TWEEN® 80 | 4.85 mg | 2.43 mg | 0.97 mg |

| Ingredients | Adjuvant A4 250 µl o/w emulsion | Adjuvant A5 250 µl o/w emulsion | Adjuvant A6 125 µl o/w emulsion | Adjuvant A7 50 µl o/w emulsion |
|---|---|---|---|---|
| alpha Tocopherol | 11.88 mg | 11.88 mg | 5.94 mg | 2.38 mg |
| Squalene | 10.7 mg | 10.7 mg | 5.35 mg | 2.14 mg |
| TWEEN® 80 | 4.85 mg | 4.85 mg | 2.43 mg | 0.97 mg |
| 3D-MPL | 50 µg | 25 µg | 25 µg | 10 µg | c) The saccharides are also formulated with two liposome based adjuvants:

Composition of Adjuvant B1
Qualitative Quantitative (per 0.5 mL dose)
Liposomes:
DOPC 1 mg
cholesterol 0.25 mg
3DMPL 50 µg
QS21 50 µg
$KH_2PO_{41}$ 3.124 mg Buffer
$Na_2HPO_{41}$ 0.290 mg Buffer
NaCl 2.922 mg
(100 mM)
WFI q.s. ad 0.5 ml Solvent
pH 6.1
1. Total $PO_4$ concentration=50 mM
Composition of Adjuvant B2
Qualitative Quantitative (per 0.5 mL dose)
Liposomes:
DOPC 0.5 mg
cholesterol 0.125 mg
3DMPL 25 µg
QS21 25 µg
$KH_2PO_{41}$ 3.124 mg Buffer
$Na_2HPO_{41}$ 0.290 mg Buffer
NaCl 2.922 mg
(100 mM)
WFI q.s. ad 0.5 ml Solvent
pH 6.1 d) The saccharides are also formulated with Adjuvant C (see above for other compositions where this adjuvant has been used):
Qualitative Quantitative (per 0.5 mL dose)
Oil in water emulsion: 50 µl
squalene 2.136 mg
α-tocopherol 2.372 mg
TWEEN® 80 0.97 mg
cholesterol 0.1 mg
3DMPL 50 µg
QS21 50 µg
$KH_2PO_{41}$ 0.470 mg Buffer
$Na_2HPO_{41}$ 0.219 mg Buffer
NaCl 4.003 mg
(137 mM)
KCl 0.101 mg
(2.7 mM)
WFI q.s. ad 0.5 ml Solvent
pH 6.8

Example 12

Impact of Conjugation Chemistry on 22F-PhtD Conjugate Immunogenicity in Balb/c Mice Groups of 30 female Balb/c mice were immunised by the intramuscular (IM) route at days 0, 14 and 28 with 13-valent PS formulations containing PS 1, 3, 4, 5, 6B, 7F, 9V, 14, 18C, 19A, 19F, 22F and 23F (dose: 0.3 µg saccharide/conjugate for PS 4, 18C, 19A, 19F and 22F and 0.1 µg saccharide/conjugate for the other PS).

PS 18C was conjugated to Tetanus Toxoid, 19F to Diphteria Toxoid, 19A to formol-detoxified Ply, 22F to PhtD and the other PS to PD.

Two formulations, constituted of either 22F-PhtD prepared by direct CDAP chemistry or 22F-AH-PhtD (ADH-derivitized PS), were compared. See Example 2, Table 1 and comment under Table 2 for characteristics of 13 valent vaccine made either with 22F directly conjugated or via an ADH spacer. The vaccine formulations were supplemented with adjuvant C.

Anti-PS22F ELISA IgG levels and opsono-phagocytosis titres were measured in sera collected at day 42.

Figure 5:
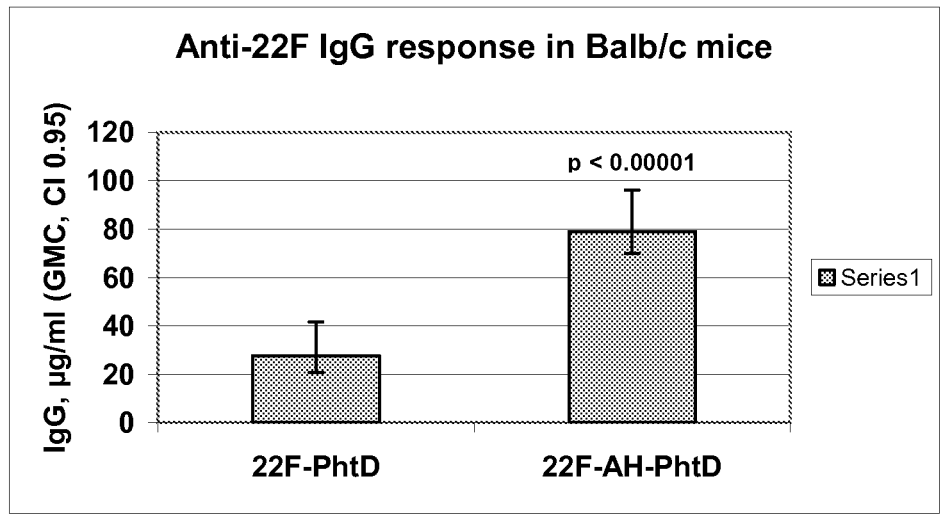
FIG. 5 Serum anti-PS IgG antibody levels Bar chart showing anti-22F IgG response in Balb/c mice FIG. 6 Anti-22F opsono-phagocytosis titres in Balb/c mice Bar chart showing anti-22F opsono-phagocytosis titres in Balb/c mice.
Figure 6:
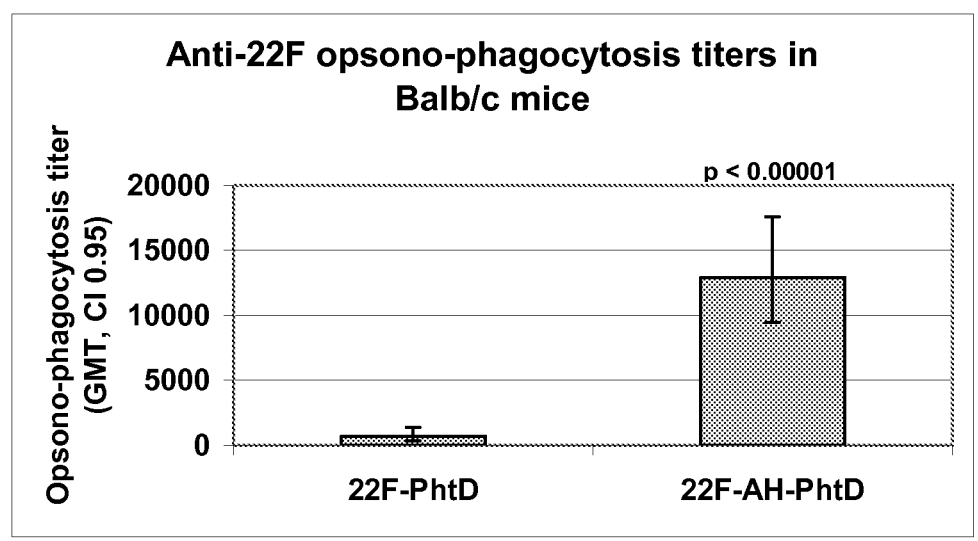

22F-AH-PhtD was shown much more immunogenic than 22F-PhtD in terms of both IgG levels (FIG. 5) and opsono-phagocytic titres (FIG. 6).

Example 13

Impact of New Adjuvants on Immunogenicity of Streptoccoccus *Pneumoniae* Capsule PS Conjugates Groups of 40 young C57B1 mice were immunised by the IM route at days 0, 14 and 28 with 13-valent PS formulations containing PS 1, 3, 4, 5, 6B, 7F, 9V, 14, 18C, 19A, 19F, 22F and 23F (dose: 0.3 μg/conjugate for PS 4, 18C, 19A, 19F and 22F and 0.1 μg/conjugate for the other PS).

PS 18C was conjugated to Tetanus Toxoid, 19F to Diphtheria Toxoid, 19A to formol-detoxified Ply, 22F to PhtD and the other PS to PD. See Example 2, Table 1 and comment under Table 2 for characteristics of 13 valent vaccine made with 22F directly conjugated.

Four formulations, supplemented with either $AlPO_4$, adjuvant A1, adjuvant A4 or adjuvant A5, were compared.

Anti-PS, Ply, PhtD and PD ELISA IgG levels were measured in sera collected at day 42 and pooled per group. The following ratio was calculated for each antigen: IgG level induced with the new adjuvant tested/IgG level induced with $AlPO_4$.

Figure 7:
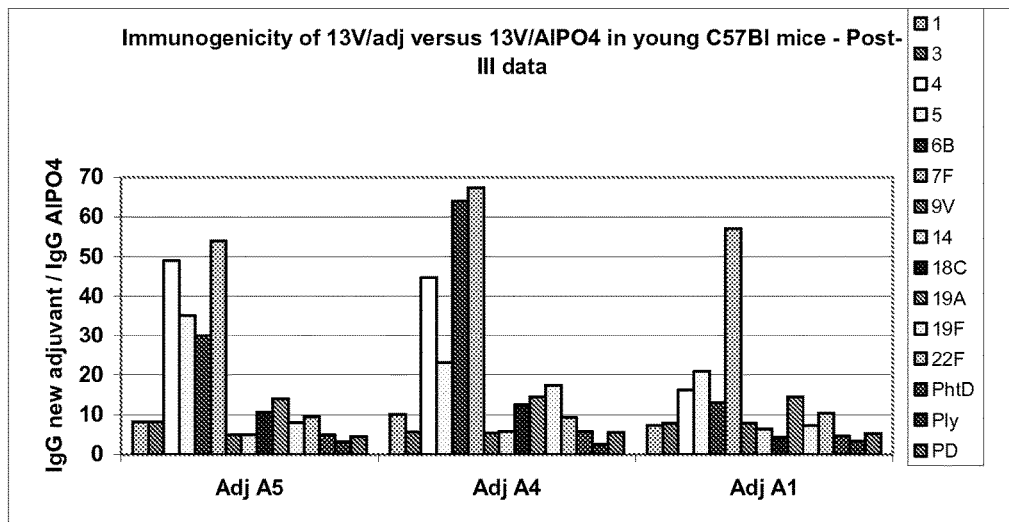
FIG. 7 Comparison of IgG responses induced in young C57BI mice-post III immunisations with new adjuvants or AIPO4 Bar chart comparing IgG responses induced in young C57B1 mice after immunisation with 13 Valent conjugate vaccine formulated in different adjuvants. The bars are in the same order indicated in the right hand column.

All the new adjuvants tested improved at least 2-fold the immune responses to serotype 1, 3, 4, 5, 6B, 7F, 9V, 14, 18C, 19A, 19F and 22F conjugates compared to the classical $AlPO_4$ formulation (FIG. 7). No reliable response was obtained for serotype 23F in this experiment.

Example 14

Protective Efficacy of a PhtD/Detoxified Phi Combo in a Pneumococcal Monkey Pneumonia Model Groups of 6 Rhesus monkeys (3 to 8 years-old), selected as those having the lowest pre-existing anti-19F antibody levels, were immunized intramuscularly at days 0 and 28 with either 11-valent PS conjugates (i.e. 1 μg of PS 1, 3, 5, 6B, 7F, 9V, 14 and 23F, and 3 μg of PS 4, 18C and 19F [of saccharide]) or PhtD (10 μg)+formol-detoxified Ply (10 μg) or PhtD/E fusion protein (10 μg) and formol-detoxified Ply (10 μg) or the adjuvant alone.

PS 18C was conjugated to Tetanus Toxoid, 19F to Diphtheria Toxoid and the other PS to PD. See Example 2, Table 1 and comment under Table 2 for characteristics of 11 valent vaccine. All formulations were supplemented with adjuvant C.

Type 19F pneumococci ($5.10^8$ cfu) were inoculated in the right lung at day 42. Colonies were counted in broncho-alveolar lavages collected at days 1, 3 and 7 post-challenge. The results were expressed as the number of animals per group either dead, lung colonized or cleared at day 7 after challenge.

Figure 8:
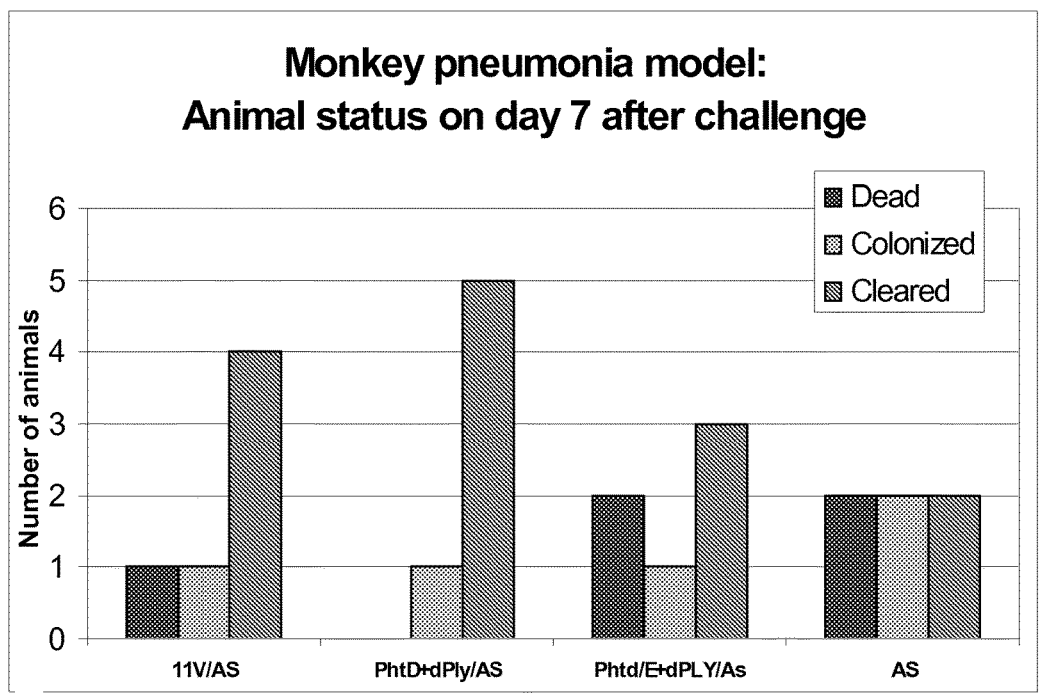
FIG. 8 Protective efficacy of PhtD and dPly protein combination against type 19F lung colonisation in Rhesus monkeys Bar chart showing the protective efficacy of different vaccine combinations in a monkey pneumonia model. The "dead" category includes monkeys that would have died but for the administration of antibiotic treatment.

As shown in FIG. 8, a good protection close to statistical significance (despite the low number of animals used) was obtained with 11-valent conjugates and the PhtD+dPly combo (p<0.12, Fisher Exact test) compared to the adjuvant alone group.

Example 15

Impact of Conjugation Chemistry on the Anti-PhtD Antibody Response and the Protective Efficacy Against a Type 4 Challenge Induced by 22F-PhtD Conjugates Groups of 20 female OF1 mice were immunised by the intramuscular route at days 0 and 14 with 3 μg of either 22F-PhtD (prepared by direct CDAP chemistry) or 22F-AH-PhtD (ADH-derivitized PS), or the adjuvant alone. Both monovalent 22F conjugates were made by the processes of Example 2 (see also Table 1 and Table 2). Each formulation was supplemented with adjuvant C.

Anti-PhtD ELISA IgG levels were measured in sera collected at day 28.

Mice were challenged intranasally with $5.10^6$ cfu of type 4 pneumococci at day 29 (i.e. a pneumococcal serotype not potentially covered by the PS present in the vaccine formulation tested). The mortality induced was monitored until day 10 post-challenge.

Figure 9:
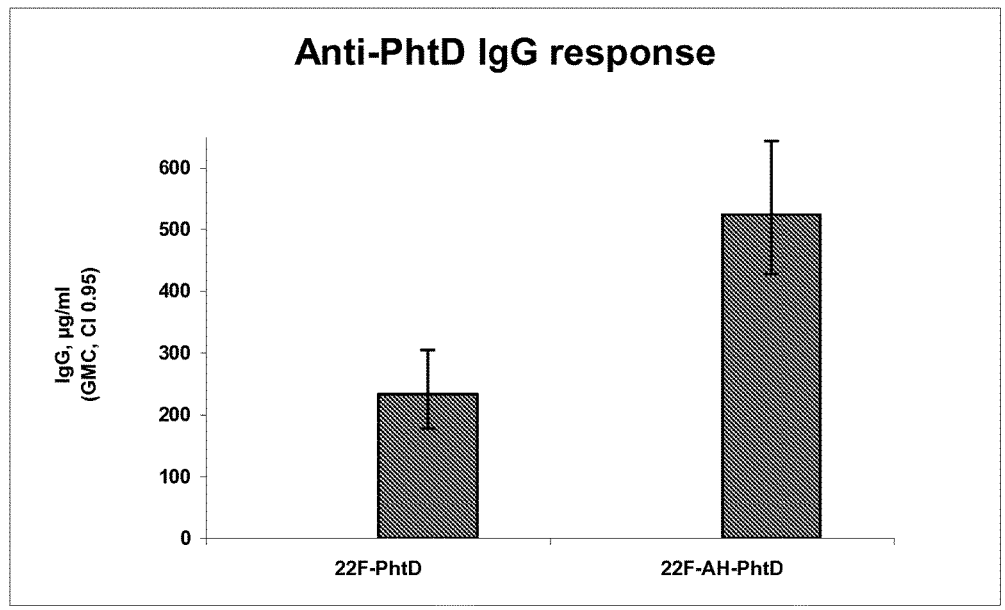
FIG. 9 Serum anti-PhtD IgG response Bar chart showing anti PhtD IgG response in Balb/c mice after immunisation with 22F-PhtD or 22F-AH-PhtD conjugates.
Figure 10:
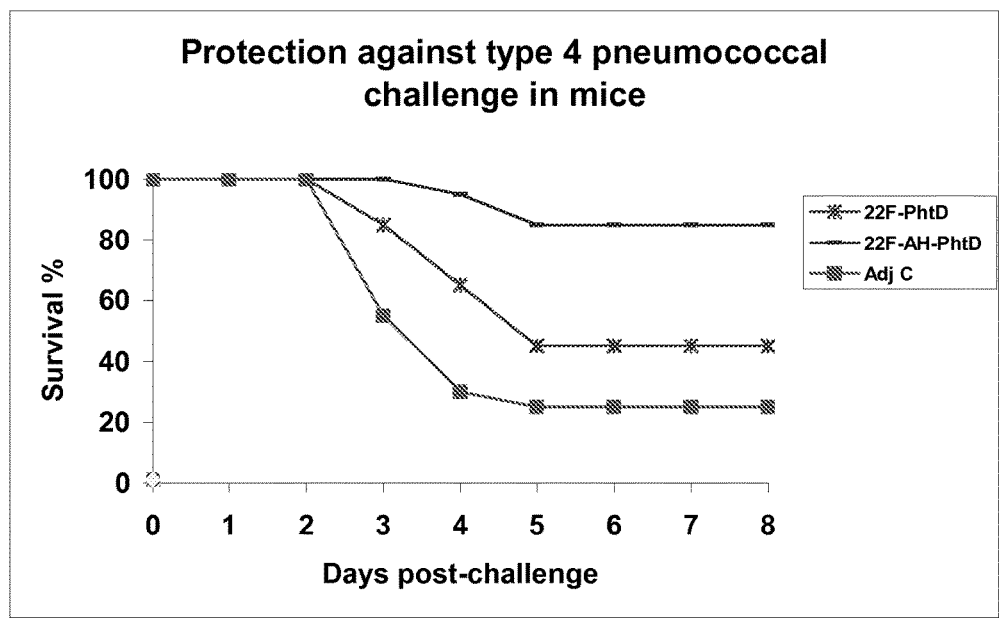
FIG. 10 Protection against type 4 pneumococcal challenge in mice Protection against type 4 pneumococcal challenge in mice after immunisation with 22F-PhtD or 22F-AH-PhtD.

Results shown in FIG. 9 demonstrate that 22F-AH-PhtD induced a significantly higher anti-PhtD IgG response compared to 22F-PhtD. This was reflected in better protection against type 4 challenge compared to 22F-PhtD as shown in FIG. 10.

Example 16

Benefit of Combining Polysaccharide and Protein in Generating a Protective Immune Response The potential synergy between immune responses directed against PhtD and capsular polysaccharides was evaluated in the mouse lethal *S. pneumoniae* challenge model. Mice were intramuscularly immunized three times (DO, 14 and 28) with PhtD. One hour before the bacterial challenge, anti-polysaccharides antibodies were passively transferred to mice (IP, 200 μl). Lethality induced by *S. pneumoniae* was followed up to 8 or 11 days after challenge. The synergy of protection is presented here for two *S. pneumoniae* strains (serotype 3 and serotype 1).

*S. pneumoniae* Strain 3/43 Challenge Model:

In this experiment, OF1 mice were immunized with PhtD adsorbed onto AIPO4 and 1.25 μg of anti-PS3 guinea pig antibodies were passively transferred 1 hour before challenge with *S. pneumoniae* serotype 3 (Spn 3/43).

Figure 11:
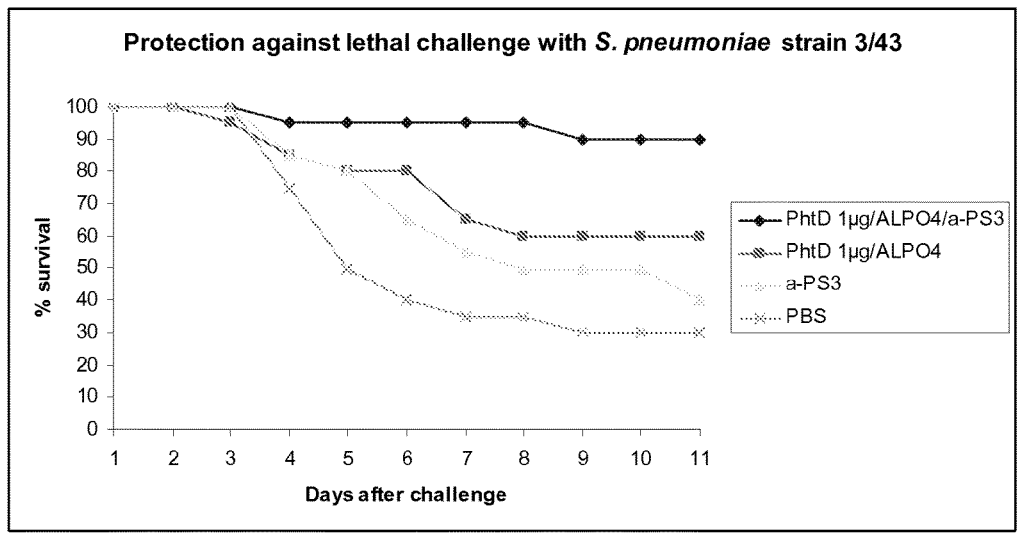
FIG. 11 Protection against lethal challenge with *S. pneumoniae* strain 3/43 following immunisation with PhtD and passive immunisation with antibodies against serotype 3 polysaccharide.

The results are shown in FIG. 11. 70% lethality was observed in mice having received PBS only. A moderate protection was observed in group of mice that received anti-PS3 antibodies or mice immunized with PhtD. A synergy, leading to an almost complete protection, was obtained in mice that combined active and passive immunization against PhtD and PS3, respectively.

*S. pneumoniae* Serotype 1/57 Challenge Model:

In this experiment, OF1 mice were immunized with PhtD adjuvanted with a TH1 adjuvant and anti-PS1 guinea pig antibodies were passively transferred one hour before challenge with *S. pneumoniae* serotype 1 (Spn 1/57).

Figure 12:
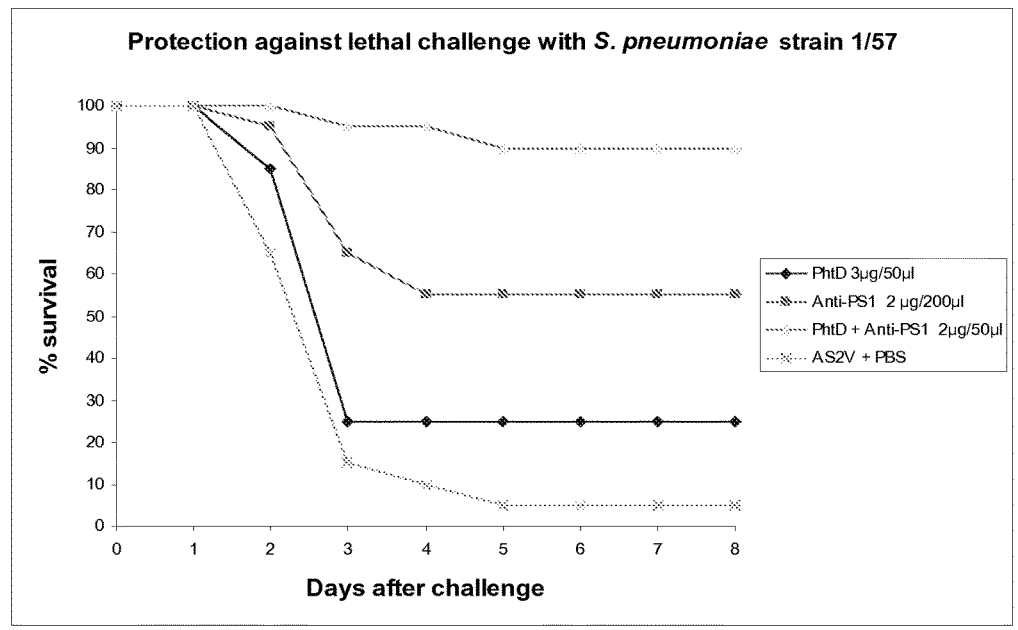
FIG. 12 Protection against lethal challenge with *S. pneumoniae* strain 1/57 following immunisation with PhtD and passive immunisation with antibodies against serotype 1 polysaccharide.

The results are shown in FIG. 12. A high lethality was observed in the control group in which mice received TH1 adjuvant (active immunization) and PBS only (passive immunization). A moderate protection was observed in group of mice that received anti-PS1 antibodies (55% survival) or mice immunized with PhtD (25% survival). A synergy, leading to an almost complete protection, was obtained in mice that combined active and passive immunization against PhtD and PS1, respectively.

Those data support the synergistic effect of the immune responses directed against a pneumococcal protein (i. e. PhtD) and capsular polysaccharides in the mechanism of protection against *S. pneumoniae* infection.

Example 17

Impact of Pneumococcal PS-TT and PS-DT Conjugates on the Immune Response Directed Against the Remaining Pneumococcal PS-PD Conjugates in a 11-Valent Formulation A formulation of containing 11 PS-PD conjugates was compared to a formulation containing 7 PS-PD, 2 PS-TT (PS 6B and 23F) and 2 PS-DT (PS 18C and 19F) conjugates in both mouse and guinea pig immunogenicity models.

Mice were intramuscularly immunized three times with ⅒ of a human dose of the vaccines (0.1 μg of PS). Blood samples were collected on day 42 and the immune response directed against each polysaccharide was measured by ELISA.

Guinea pigs were intramuscularly immunized three times with ¼ of a human dose of the vaccines (0.25 μg of PS). INFANRIX® HEXA was co-administered in order to mimic the human situation. Blood samples were collected on day 42 and the immune response directed against each polysaccharide was measured by ELISA.

| | | Experiment N° SPN115 (pims 20040304) Mouse | | | | Experiment N° SPN116 (pims 20040308) Guinea pig | |
|---|---|---|---|---|---|---|---|
| | ELISA | All on PD 1 μg | 6B-TTAH 1 μg<br>23F-TTAH 1 μg<br>18C-DTAH 1 μg<br>19F-DT 1 μg<br>¼-PD 1 μg<br>others on PD 1 μg | | ELISA | All on PD 1 μg | 6B-TTAH 1 μg<br>23F-TTAH 1 μg<br>18C-DTAH 1 μg<br>19F-DT 1 μg<br>¼-PD 1 μg<br>others on PD 1 μg |
| 1 | GMC | 6.148 | 19.961* | 1 | GMC | 8.244 | 33.479* |
| | 95% CI | 4.54-8.33 | 14.73-27.05 | | 95% CI | 4.745-14.324 | 21.507-52.114 |
| | % seropos | 100% | 100% | | % seropos | 100% | 100% |
| 3 | GMC | 1.763 | 2.483 | 3 | GMC | 2.348 | 1.619 |
| | 95% CI | 1.223-2.542 | 1.693-3.643 | | 95% CI | 1.42-3.89 | 0.84-3.13 |
| | % seropos | 100% | 100% | | % seropos | 100% | 100% |
| 4 | GMC | 3.643 | 11.849* | 4 | GMC | 9.211 | 19.033 |
| | 95% CI | 2.498-5.311 | 8.909-15.759 | | 95% CI | 5.535-15.238 | 10.816-33.494 |
| | % seropos | 100% | 100% | | % seropos | 100% | 100% |
| 5 | GMC | 2.291 | 5.154* | 5 | GMC | 14.04 | 14.791 |
| | 95% CI | 1.575-3.332 | 3.829-6.939 | | 95% CI | 9.967-19.776 | 10.227-21.392 |
| | % seropos | 100% | 100% | | % seropos | 100% | 100% |
| 6B | GMC | 0.048 | 0.537* | 6B | GMC | 0.491 | 1.667 |
| | 95% CI | 0.031-0.075 | 0.342-0.843 | | 95% CI | 0.292-0.825 | 0.746-3.726 |
| | % seropos | 44% | 100% | | % seropos | 100% | 100% |
| 7F | GMC | 0.297 | 0.774 | 7F | GMC | 10.467 | 37.49* |
| | 95% CI | 0.22-0.41 | 0.48-1.25 | | 95% CI | 5.979-18.324 | 21.944-64.051 |
| | % seropos | 100% | 100% | | % seropos | 100% | 100% |
| 9V | GMC | 2.098 | 8.098* | 9V | GMC | 5.459 | 10.309 |
| | 95% CI | 1.575-2.793 | 6.507-10.078 | | 95% CI | 3.106-9.589 | 6.183-17.187 |
| | % seropos | 100% | 100% | | % seropos | 100% | 100% |
| 14 | GMC | 4.983 | 9.327* | 14 | GMC | 1.235 | 4.358* |
| | 95% CI | 3.742-6.634 | 7.669-11.344 | | 95% CI | 0.686-2.224 | 2.073-9.161 |
| | % seropos | 100% | 100% | | % seropos | 100% | 100% |
| 18C | GMC | 0.469 | 3.274* | 19F | GMC | 7.769 | 15.933* |
| | 95% CI | 0.32-0.69 | 2.67-4.01 | | 95% CI | 5.617-10.745 | 12.036-21.092 |
| | % seropos | 100% | 100% | | % seropos | 100% | 100% |
| 19F | GMC | 3.052 | 21.274* | 18C | GMC | 2.373 | 8.744* |
| | 95% CI | 2.14-4.35 | 16.54-27.37 | | 95% CI | 1.297-4.341 | 5.128-14.908 |
| | % seropos | 100% | 100% | | % seropos | 100% | 100% |
| 23F | GMC | 0.072 | 1.209 | 23F | GMC | 5.621 | 33.791* |
| | 95% CI | 0.044-0.117 | 0.457-3.2 | | 95% CI | 3.289-9.608 | 20.838-54.797 |
| | % seropos | 38% | 71% | | % seropos | 100% | 100% |

An increased immune response directed against most of the polysaccharide conjugated to PD was observed both in mice and in guinea pigs in the formulation containing two polysaccharide conjugated to TT (PS 6B and 23F) and DT (PS 18C and 19F) when compared to the 11-V PD formulation. These differences were statistically significant against PS 1, 4, 5, 9V and 14 as well as against PS 1, 7F and 14 in mice and guinea pigs, respectively.

The invention claimed is:

1. A multivalent *Streptococcus pneumoniae* immunogenic composition comprising components including saccharide conjugate components, wherein the saccharide conjugate components consist of conjugates of capsular saccharides of 16 different serotypes of *Streptococcus pneumoniae* wherein the different *Streptococcus pneumoniae* serotypes are selected from the group consisting of 1, 2, 3, 4, 5, 6A, 6B, 7F, 8, 9N, 9V, 10A, 11A, 12F, 14, 15, 17F, 18C, 19A, 19F, 20, 22F, 23F, and 33F, wherein the capsular saccharides are separately conjugated to 2 or more different carrier proteins,
   wherein the serotype 22F capsular saccharide has an average saccharide size of between 50 and 800 kDa,
   wherein the serotype 19F capsular saccharide is conjugated to diphtheria toxoid,
   wherein the serotype 19F capsular saccharide is the only capsular saccharide conjugated to the diphtheria toxoid, wherein the capsular saccharides from half of the 16 different *Streptococcus pneumoniae* serotypes are conjugated to protein D from *Haemophilus influenzae*, and wherein the immunogenic composition comprises an adjuvant, wherein the adjuvant is selected from the group consisting of a metal salt, an oil in water emulsion, a Toll like receptor agonist, saponin, and a combination thereof.

2. The multivalent *Streptococcus pneumoniae* immunogenic composition according to claim 1, wherein the capsular saccharides of the *Streptococcus pneumoniae* serotypes are conjugated to 3 different carrier proteins.

3. The multivalent *Streptococcus pneumoniae* immunogenic composition according to claim 1, wherein the capsular saccharides of the *Streptococcus pneumoniae* serotypes are conjugated to 5 different carrier proteins.

4. The multivalent *Streptococcus pneumoniae* immunogenic composition according to claim 1 further comprising one or more unconjugated or conjugated *Streptococcus pneumoniae* proteins.

5. A method of inducing an immune response in a human against disease caused by *Streptococcus pneumoniae* infection comprising administering an immunoprotective dose of the multivalent *Streptococcus pneumoniae* immunogenic composition of claim 1.

6. A method of inducing an immune response in a human against disease caused by *Streptococcus pneumoniae* infection comprising administering an immunoprotective dose of the multivalent *Streptococcus pneumoniae* immunogenic composition of claim 2.

7. A method of inducing an immune response in a human against disease caused by *Streptococcus pneumoniae* infection comprising administering an immunoprotective dose of the multivalent *Streptococcus pneumoniae* immunogenic composition of claim 3.

8. A method of inducing an immune response in a human against disease caused by *Streptococcus pneumoniae* infection comprising administering an immunoprotective dose of the multivalent *Streptococcus pneumoniae* immunogenic composition of claim 4.

9. The multivalent *Streptococcus pneumoniae* immunogenic composition according to claim 1, wherein the capsular saccharides of the *Streptococcus pneumoniae* serotypes are conjugated to 4 different carrier proteins.

10. The multivalent *Streptococcus pneumoniae* immunogenic composition according to claim 1 wherein the serotype 19A capsular saccharide has an average saccharide size of between 50 and 800 kDa.

11. The multivalent *Streptococcus pneumoniae* immunogenic composition according to claim 1 wherein the serotype 18C capsular saccharide has an average saccharide size of between 70 and 300 kDa.

12. The multivalent *Streptococcus pneumoniae* immunogenic composition according to claim 1 wherein the capsular saccharides are sized by microfluidisation.

13. The multivalent *Streptococcus pneumoniae* immunogenic composition according to claim 1 wherein the serotype 18C capsular saccharide is sized by microfluidisation.

14. The multivalent *Streptococcus pneumoniae* immunogenic composition according to claim 1 wherein the adjuvant is selected from a metal salt and a Toll like receptor agonist and wherein the metal salt is an aluminum salt.

15. The multivalent *Streptococcus pneumoniae* immunogenic composition according to claim 1 wherein the adjuvant is selected from an aluminum salt and a Toll like receptor agonist and the aluminum salt is an aluminum phosphate salt and the Toll like receptor is a Toll like receptor 4 agonist.

16. The multivalent *Streptococcus pneumoniae* immunogenic composition according to claim 15 wherein the Toll like receptor 4 agonist is 3D-MPL.

* * * * *